US012060579B2

(12) United States Patent
Murry et al.

(10) Patent No.: US 12,060,579 B2
(45) Date of Patent: Aug. 13, 2024

(54) HUMAN PLURIPOTENT STEM CELL DERIVED ENDOCARDIAL ENDOTHELIUM

(71) Applicant: UNIVERSITY OF WASHINGTON, Seattle, WA (US)

(72) Inventors: Charles E. Murry, Seattle, WA (US); Lil Pabon, Seattle, WA (US); Nathan Palpant, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 445 days.

(21) Appl. No.: 16/801,559

(22) Filed: Feb. 26, 2020

(65) Prior Publication Data

US 2020/0231933 A1 Jul. 23, 2020

Related U.S. Application Data

(62) Division of application No. 15/437,786, filed on Feb. 21, 2017, now Pat. No. 10,612,002.

(60) Provisional application No. 62/297,241, filed on Feb. 19, 2016.

(51) Int. Cl.
  *C12N 5/077* (2010.01)
  *A61K 35/545* (2015.01)

(52) U.S. Cl.
  CPC .......... *C12N 5/0657* (2013.01); *A61K 35/545* (2013.01); *C12N 2501/115* (2013.01); *C12N 2501/155* (2013.01); *C12N 2501/16* (2013.01); *C12N 2501/165* (2013.01)

(58) Field of Classification Search
  CPC .............................. C12N 5/0657; A61K 35/545
  See application file for complete search history.

(56) References Cited

U.S. PATENT DOCUMENTS

| 8,815,593 B2 | 8/2014 | Laflamme |
| 2009/0269314 A1 | 10/2009 | Keller et al. |
| 2010/0261277 A1 | 10/2010 | Colton et al. |

OTHER PUBLICATIONS

Smiljic, 2017, Medicina, 53:295-302.*
Velnar, Cells 2021, 10, 2338, 15 pages.*
Brutsaert, 1992, American Journal of Physiology Heart and Circulatory Physiology, 263:H985-H1002.*
Misfeldt, Developmental Biology 333 (2009) 78-89).*
Zhang, Circulation Research, 20118, 122:774-789.*
Gurevich, Cells 2021, 10, 2338, 15 pages.*
Dye Cold Spring Harb Perspect Biol 2020;12:a036723. 17 pages.*
"Supplementary Materials and Methods", Development 142.
Aulehla et al., "Signaling gradients during Paraxial Mesoderm Development", Cold Spring Harbor Laboratory Press 2.2 (2010).
Barnes et al. "Analysis of the Hand1 cell lineage reveals novel contributions to cardiovascular, neural crest, extra-embryonic, and lateral mesoderm derivatives." Dev Dyn 239(11): 3086-3097 (2010).
Brand "Heart Development: Molecular insights into cardiac specification and early morphogenesis" Developmental Biology, 258 1-19 (2003).
Chan, et al. "Mesp1 Patterns Mesoderm into Cardiac, Hematopoeitic, or Skeletal Myogenic Progenitors in a Context-Dependent Manner" Cell Stem Cell 587-601 (2013).
Chen, et al. "Notch signaling respecifies the hemangioblast to a cardiac fate" Nature biotechnology 26.10, 1169 (2008).
Choi et al. "Identification of the hemogenic endothelial progenitor and its direct precursor in human pluripotent stem cell differentiation cultures." Cell Rep 2(3): 553-567 (2012).
Ciau_Uitz et al., "VEGFA-dependent and independent pathways synergie to drive Scl expression and initiate programming of the blood stem cell lineage in Xenopus", Development,. 2632 (2013).
Ciau-Uitz et al. "Tel1/ETV6 Specifies Blood Stem Cells through the Agency of VEGF Signaling", Developmental Cell 18.4, 569-578 (2010).
Davidson et al., "Wnt/b-catenin signaling promotes differentiation, not self-renewal, of human embryonic stem cells and is repressed by Oct4", Proceedings of the National Academy of Sciences, 109.12 4485-4490. (2012).
De La Pompa et al., "Role of the NF-Atc transcription factor in morphpgenesis of cardiac valves and septum", Nature, 392, 182 (1998).
Dubois, et al., "SIRPA is a specific cell-surface marker for isolating cardiomyocytes derived from human pluripotent stem cells" Nature Biotechnology, 29.11, 1011 (2011).
Elliot et al., "NKX2-5 eGFP/w hESCs for isolation of human cardiac progenitors and cardiomyocytes", Nature methods, 8.12: 1037 (2011).
Faial et al. "Brachyury and SMAD signalling collaboratively orchestrate distinct mesoderm and endoderm gene regulatory networks in differentiating human embryonic stem cells." Development 142(12): 2121-2135 (2015).
Ferdous et al., "Nkx2-5 transactivates the Ets-related protein 71 gene and specifies an endothelial/endocardial fate in the developing embryo", Proceedings of the National Academy of Sciences, 106:3, 814-819 (2009).
Gantz et al., "Targeted Genomic Integration of a Selectable Floxed Dual Fluorescence Reporter in Human Embryonic Stem Cells", PLos One, 7.10, (2012).
Gekas et al., "Mef2C is a lineage-restriced target of Scl/Tal1 and regulates megakaryopoiesis and B-cell homeostasis", Blood, 113. 15, 3461-3471 (2009).
Kattman et al. "Stage-specific optimization of activin/nodal and BMP signaling promotes cardiac differentiation of mouse and human pluripotent stem cell lines." Cell Stem Cell 8(2): 228-240 (2011).
Kennedy et al. "Development of the hemangioblast defines the onset of hematopoiesis in human ES cell differentiation cultures." Blood 109(7): 2679-2687 (2007).
Kennedy et al. "T lymphocyte potential marks the emergence of definitive hematopoietic progenitors in human pluripotent stem cell differentiation cultures." Cell Rep 2(6): 1722-1735 (2012).

(Continued)

*Primary Examiner* — Valarie E Bertoglio
(74) *Attorney, Agent, or Firm* — Nixon Peabody LLP; Mark J. FitzGerald; Alissa R. Young

(57) ABSTRACT

Provided herein are methods that enable the polarization of hPSC mesoderm such that closely related yet distinct cardiovascular populations can be generated efficiently without the need of post-facto enrichment.

13 Claims, 22 Drawing Sheets

Specification includes a Sequence Listing.

(56) References Cited

OTHER PUBLICATIONS

Kim et al., "Activin-A and Bmp4 levels modulate cell type specification during CHIR-induced cardiomyogenesis", PLoS One 10(2) e0118670 (2015).
Kim et al., "Signaling axis involving Hedgehog, Notch, and Scl promotes the embryonic endothelial-to-hematopoietic transition", Proceedings of the National Academy of Sciences, 110:2 141-150 (2013).
Laflamme et al., "Cardiomyocytes derived from human embryonic stem cells in pro-survival factors enhance function of infarcted rat hearts", Nat Biotechnol 25(9) 1015-1024 (2007).
Lancrin et al., "The haemangioblast generates haematopoietic cells through a haemogenic endothelium stage", Nature, 457:12, 892 (2009).
Leda et al., "Direct Reprogramming of Fibroblasts into Functional Cardiomyocytes by Defined Factors", Cell, 142.3, 375-386 (2010).
Lengerke et al., "Interactions between Cdx genes and retinoic acid modulate early cardiogenesis", Developmental biology, 354: 134-142 (2011).
Levenberg et al. "Isolation, differentiation and characterization of vascular cells derived from human embryonic stem cells." Nat Protoc 5(6): 1115-1126 (2010).
Lian et al. "Directed cardiomyocyte differentiation from human pluripotent stem cells by modulating Wnt/β-catenin signaling under fully defined conditions." Nat Protoc 8(1): 162-175 (2013).
Lian et al. "Insulin inhibits cardiac mesoderm, not mesendoderm, formation during cardiac differentiation of human pluripotent stem cells and modulation of canonical Wnt signaling can rescue this inhibition." Stem Cells 31(3): 447-457 (2013).
Lian et al. "Robust cardiomyocyte differentiation from human pluripotent stem cells via temporal modulation of canonical Wnt signaling." Proc Natl Acad Sci U S A 109(27): E1848-E18557 (2012) 10 Pages.
Lin et al., "Requirement of the MADS-box transcription factor MEF2C for vascular development", Development 125, 4565-4574 (1998).
Martin, et al., "Canonical Wnt Signaling Dynamically Controls Multiple Stem Cell Fate Decisions during Vertebrate Body Formation", Developmental Cell 22, 223-232 (2012).
Maska et al., "A TIx2-Cre Mouse Line Uncovers Essential Roles for Hand1 in Extraembryonic and Lateral Mesoderm", Genesis 48:479-484 (2010).
Mendjan et al. "NANOG and CDX2 pattern distinct subtypes of human mesoderm during exit from pluripotency." Cell Stem Cell 15(3): 310-325 (2014).
Misfeldt et al. "Endocardial cells are a distinct endothelial lineage derived from Flk1+ multipotent cardiovascular progenitors." Dev Biol 333(1): 78-89 (2009).
Morikawa et al., "Extra-embryonic vasculature development is regulated by the transcription factor HAND1", Development 131, 2195-2204 (2004).
Mummery et al. "Differentiation of human embryonic stem cells and induced pluripotent stem cells to cardiomyocytes! a methods overview." Circ Res 111(3): 344-358 (2012).
Murry et al. "Differentiation of embryonic stem cells to clinically relevant populations: lessons from embryonic development." Cell 132(4): 661-680 (2008).
Nakano et al. "Haemogenic endocardium contributes to transient definitive haematopoiesis", Nature Communications 4:1564, 1-10 (2013).
Nostro et al. "Wnt, activin, and BMP signaling regulate distinct stages in the developmental pathway from embryonic stem cells to blood." Cell Stem Cell 2(1): 60-71 (2008).
Nourse et al. "VEGF induces differentiation of functional endothelium from human embryonic stem cells: implications for tissue engineering." Arterioscler Thromb Vasc Biol 30(1): 80-89 (2010).
Orlova et al., "Generation, expansion and functional analysis of endothelial cells and pericytes derived from human pluripotent stem cells", 9:6 1514-1531 (2014). Nature Protocols.
Ovchinnikov et al., "Isolation of Contractile Cardiomyocytes from Human Pluripotent Stem-Cell-Derived Cardiomyogenic Cultures Using a Human NCX1-EGFP Reporter" 24:1, 11-20 (2015).
Paffet-Lugassy et al., "Heart eld origin of great vessel precursors relies on nkx2.5—mediated vasculogenesis", Nature Cell Biology 15:11, 1362-1369 (2013).
Paige et al. "A temporal chromatin signature in human embryonic stem cells identifies regulators of cardiac development." Cell 151(1): 221-232 (2012).
Paige et al. "Endogenous Wnt/beta-catenin signaling is required for cardiac differentiation in human embryonic stem cells." PLoS One 5(6): 1-8 (2010).
Paige et al., "A Temporal Chromatin Signature in Human Embryonic Stem Cells Identifies Regulators of Cardiac Development", Cell 151, 221-232 (2012).
Paige et al., "Endogenous Wnt/b-Catenin Signaling Is Required for Cardiac Differentiation in Human Embryonic Stem Cells", PLoS One 5:6, 11134 1-8 (2010).
Palpant et al. "Cardiac development in zebrafish and human embryonic stem cells is inhibited by exposure to tobacco cigarettes and e-cigarettes." PLoS One 10(5): 1-19 (2015).
Palpant et al. "Inhibition of β-catenin signaling respecifies anterior-like endothelium into beating human cardiomyocytes." Development 142(18): 3198-3209 (2015).
Palpant et al. "Transmembrane protein 88: a Wnt regulatory protein that specifies cardiomyocyte development." Development 140(18): 3799-3808 (2013).
Palpant et al., "Inhibition of β-catenin signaling respecifies anterior-like endothelium into beating human cardiomyocytes", 142, 3198-3209 (2015).
Papapetrou et al., "Stoichiometric and temporal requirements of Oct4, Sox2, Klf4, and c-Myc expression for efficient human iPSC induction and differentiation", PNAS 106:31, 12759-12764 (2009).
Peterkin et al., "Common genetic control of haemangioblast and cardiac development in zebrafish", 136, 1465-1474 (2009).
Rafii et al., "Human ESC-derived hemogenic endothelial cells undergo distinct waves of endothelial to hematopoietic transition", Blood 121:5, 770-779 (2018).
Ranger et al., "The Transcription factor NF-Atc is essential for cardiac valve formation", Nature 392, 186-190 (1998).
Reid et al., "Transcriptional integration of Wnt and Nodal pathways in establishment of the Spemann organizer", Developmental Biology, 368:231-241 (2012).
Scheller et al., "Hematopoietic stem cell and multilineage defects generated by constitutive b-catenin activation", Nature Immunology 7:10, 1037-1047 (2006).
Schoenebeck et al., "Vessel and Blood Specification Override Cardiac Potential in Anterior Mesoderm", Developmental Cell 13, 254-267 (2007).
Shalaby et al., "A Requirement for Flk1 in Primitive and Defiitive Hematopoiesis and Vasculogenesis", Cell 89, 981-990 (1997).
Siedner et al., "Developmental changes in contractility and sarcomeric proteins from the early embryonic to the adult stage in the mouse heart", J Physiol 548.2, 593-505 (2003).
Sturgeon et al., "Wnt signaling controls the specification of definitive and primitive hematopoiesis from human pluripotent stem cells", Nature Biotechnology 32:6, 554-561 (2014).
Sumi et al. "Defining early lineage specification of human embryonic stem cells by the orchestrated balance of canonical Wnt/beta-catenin, Activin/Nodal and BMP signaling." Development 135(17): 2969-2979 (2008).
Takahashi et al., "Induction of Pluripotent Stem Cells from Mouse Embryonic and Adult Fibroblast Cultures by Defined Factors", Cell 126, 663-676 (2006).
Ten Berge et al., "Wnt Signaling Mediates Self-Organization and Axis Formation in Embryoid Bodies", Cell Stem Cell 3, 508-518 (2008).
Tohyama et al., "Distinct Metabolic Flow Enables Large-Scale Purification of Mouse and Human Pluripotent Stem Cell-Derived Cardiomyocytes", Cell Stem Cell 12, 127-137 (2013).
Jeno et al. "Biphasic role for Wnt/beta-catenin signaling in cardiac specification in zebrafish and embryonic stem cells." Proc Natl Acad Sci U S A 104(23): 9685-9690 (2007).

(56) References Cited

OTHER PUBLICATIONS

Urness et al., "Redundant and dosage sensitive requirements for Fgf3 and Fgf10 in cardiovascular development", Developmental Biology 356, 383-397 (2011).

Van Handel et al. "Scl represses cardiomyogenesis in prospective hemogenic endothelium and endocardium." Cell 150(3): 590-605 (2012).

Merbuchen et al., "Direct conversion of fibroblasts to functional neurons by defined factors", Nature 463 1035-1041 (2010).

Walmsley et al., "Adult and embryonic blood and endothelium derive from distinct precursor populations which are differentially programmed by BMP in Xenopus", Development 129, 5683-5695 (2002).

Wamstad et al. "Dynamic and coordinated epigenetic regulation of developmental transitions in the cardiac lineage." Cell 151(1): 206-220 (2012).

Wang et al., "Cdx gene deficiency compromises embryonic hematopoiesis in the mouse", PNAS 105:22, 7756-7761 (2008).

White et al. "Limited gene expression variation in human embryonic stem cell and induced pluripotent stem cell-derived endothelial cells." Stem Cells 31(1): 92-103 (2013).

Willems et al. "Small-molecule inhibitors of the Wnt pathway potently promote cardiomyocytes from human embryonic stem cell-derived mesoderm." Circ Res 109(4): 360-364 (2011).

Williams et al., "SnapShot: directed differentiation of pluripotent stem cells", Cell 149(5) 1147-1147e.1 (2012).

Woll et al., "Wnt signaling promotes hematoendothelial cell development from human embryonic stem cells", Blood 111:1, 122-131 (2008).

Wu et al., "Nfatc1 Coordinates Valve Endocardial Cell Lineage Development Required for Heart Valve Formation", Circulation Research 10:1161, 183-191 (2011).

Xu et al., "Activin, BMP and FGF pathways cooperate to promote endoderm and pancreatic lineage cell differentiation from human embryonic stem cells", Mech Dev 128(7-10) 412-427 (2011).

Xu et al., "Construction of a Vertebrate Embryo from Two Opposing Morphogen Gradients", 344, 87-89 (2014).

Yamaguchi et al., "T (Brachyury) is a direct target pf Wnt3a during paraxial mesoderm specification", Genes & Development 13:3185-3190 (1990).

Yutzey et al., "Diversification of Cardiomyogenic Cell Lineages During Early Heart Development", 77:216-219 (1995).

Zhang et al. "Extracellular matrix promotes highly efficient cardiac differentiation of human pluripotent stem cells: the matrix sandwich method." Circ Res 111(9): 1125-1136 (2012).

Zheng et al., "In vitro microvessels for the study of angiogenesis and thrombosis", PNAS 109:24 9342-9347 (2012).

Zovein et al., "Fate Tracing Reveals the Endothelial Origin of Hematopoietic Stem Cells", Cell Stem Cell 3, 625-636 (2008).

\* cited by examiner

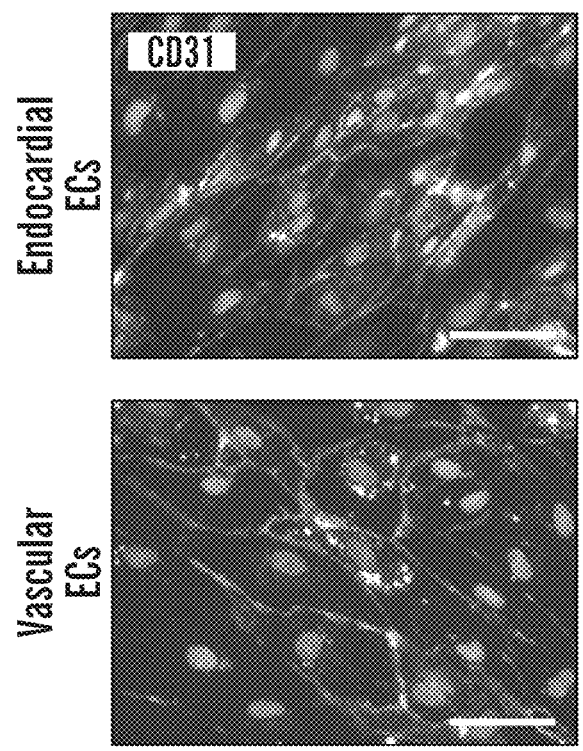
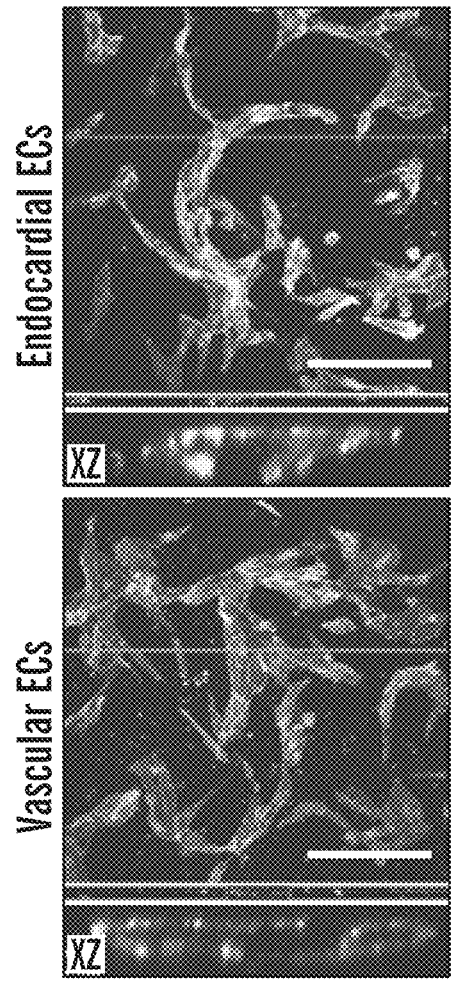
*FIG. 6B*                    *FIG. 6C*

SEQUENCE LISTING

```
<160> NUMBER OF SEQ ID NOS: 56

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgacactggc aaaacaatgc a                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtccttttc accagcaagc t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caaatcctca tcctcagttt g                                              21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtcagaatag gttggagaat tg                                             22

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atgcacggca tctgggaatc                                                20
```

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtcactgtcc tgcaagttgc tgtc                                          24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tggaggtggg atgaagtcac ctat                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aacccagcct gaggcaatga gatt                                          24

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aacagctatc caaatgcag                                                19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcacagggga gttccataaa                                               20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcgaagtggt tccttggcag ac                                            22

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cctcctgctt gcctacaaag tgtc                                          24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gaggagaaag tggaggtctg gtt                                           23

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctctgatgag gaccgcttct g                                             21

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtggcagcg gtaagactc                                                19

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgtaacggct gtaatgaaac tcc                                           23

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcagaggcgg aactgatctt                                               20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
cgaccctctg tgccatagat g                                     21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
aactacgtgg agatcatgcc c                                     21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gactccctgg tagctttgtc                                       20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
gctgccttca atcttctcct g                                     21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
ataaagggct cggctgtagg                                       20

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
acaccccaat ctcgatatgt ttg                                   23

<210> SEQ ID NO 24

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gttgcacaga tagtgacccg t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atttccctat gtgttggttg c                                              21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cgttcttgct gaagccgatg                                                20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccaaggaccc tagagccgaa                                                20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ataggcgggg taggcgttat                                                20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tcaaagaggc cttttcattg                                                20

<210> SEQ ID NO 30
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cgtctcaaag tccagcatct                                                  20

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttcaccaaag atctgctcct cgct                                             24

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ttattactgg tgtggagtgg gtgtgg                                           26

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
caagttggaa gacgagtgct                                                  20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
atgggcctct tgtagagctt                                                  20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tccaacgtct tttccatgtt                                                  20

<210> SEQ ID NO 36
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 36
tctgtcccat tgagcttctc                                                    20

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gaaccacaag atcacgcaat ta                                                 22

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
acaccattct cacactggta t                                                  21

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
atgacaaccc actgagaaga gaa                                                23

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cgaaggtcag attggtctca tattt                                              25

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
agaacttaca cacgcgac ctg                                                  23

<210> SEQ ID NO 42
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 42
catctctaac cggaccatac tgc                                              23

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aagggcacag catctgtagt ca                                               22

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aagtcttcag cagagggtca cgta                                             24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aaatcctctt cctctgaggc tgga                                             24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
aagaggcagc tggtgataag ggtt                                             24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
atcatttcta gcgcatggcc tggt                                             24

<210> SEQ ID NO 48
<211> LENGTH: 24
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 48
atttgtggag ggcgaggtca taga                                            24

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gcattttcct tgatccctgt                                                 20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agcagcttta gggtgcaaat                                                 20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tcaaagacgc actcttccac                                                 20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gtgcagcgac aaaaagaaaa                                                 20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctttcaggtg tacccattgc                                                 20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 54
aaagtctcca ggaagctggt                                                  20

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
atgtggtcct atttaagcca gccc                                             24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tcatctggct gaagacacca gctt                                             24
```

HUMAN PLURIPOTENT STEM CELL DERIVED ENDOCARDIAL ENDOTHELIUM

CROSS REFERENCE TO RELATED APPLICATIONS

This application is a Divisional of U.S. application Ser. No. 15/437,786, filed Feb. 21, 2017, which claims benefit under 35 U.S.C. § 119(e) of U.S. Provisional Application No. 62/297,241 filed Feb. 19, 2016, the contents of each of which are incorporated herein by reference in their entireties.

GOVERNMENT SUPPORT

This invention was made with government support under Grant Nos. P01 GM081619 and U01 HL099997, awarded by the National Institutes of Health. The government has certain rights in the invention.

The instant application contains a Sequence Listing which has been submitted electronically in ASCII format and is hereby incorporated by reference in its entirety. Said ASCII copy, created on Mar. 29, 2017, is named 034186-088681_US_SL.txt and is 12,941 bytes in size.

FIELD OF THE INVENTION

The field of the invention relates to the efficient differentiation of human pluripotent cells to cells committed to the cardiovascular lineage.

BACKGROUND

The heart is the earliest organ to form in the developing embryo providing the basis for a functional circulation as other organ systems develop. Emerging bioengineering and biotechnology approaches to study the formation of the mesoderm and its cellular linages are a great opportunity to develop new insights into this complex developmental process. In particular, human pluripotent stem cells (hPSCs) provide an ideal system with which to study these questions because they are of human origin, scalable, allow for the use of advanced molecular biology tools for analysis, and provide a simplified system for studying cell fate choices in early development. During embryogenesis, cell fate decisions are coordinated by gradients of cytokines and morphogens, which allow for differentiation and organization of multiple cell types into complex tissues[1].

The capacity to direct these complex fate choices is mediated by critical spatiotemporally orchestrated cues required to direct specific cell fates and cell subtypes. Well-described anterior-posterior morphogen gradients principally involving Activin/Nodal and bone morphogenic protein (BMP4) are required for developing a polarized axis during gastrulation[2–5]. This polarization of mesoderm gives rise to the heterogeneous cell types of the cardiovascular system including cardiomyocytes, endocardium, vascular endothelium, and the hematopoietic system that are specified by differences in VEGF and Wnt signaling. Studies using hPSCs[6–11] have contributed significantly to knowledge about mechanisms of human mesodermal patterning. Because of the different degrees of differentiation efficiency for the desired cell types, diverse methods have been used to select and enrich for cardiomyocytes or endothelial cells[12–20].

SUMMARY

Provided herein, in part, is a protocol that enables the polarization of hPSC mesoderm such that closely related yet distinct cardiovascular populations can be generated efficiently without the need for post-facto enrichment (e.g., sorting of cells). hPSC polarization towards anterior cardiogenic mesoderm allows for the derivation of both cardiac muscle and endocardial endothelium, whereas hemogenic endothelium can be derived from cultures polarized towards posterior mesoderm.

In one aspect, provided herein is a method for generating human endocardial endothelial cells, comprising: culturing human pluripotent stem cells in defined medium, in the presence of Activin A, and then in the presence of a Bone Morphogenetic Protein, such as Bone Morphogenetic Protein-2 or -4 (BMP2 or BMP4).

In one embodiment of this aspect and all other aspects provided herein, the pluripotent stem cells comprise human embryonic stem cells (ESCs) or human induced pluripotent stem cells (iPSCs).

In another embodiment of this aspect and all other aspects provided herein, the culture comprises a monolayer culture.

In another embodiment of this aspect and all other aspects provided herein, the method does not involve a feeder layer, embryoid bodies or embryoid body formation.

In another embodiment of this aspect and all other aspects provided herein, the Activin A is present in defined medium in a concentration of at least about 100 ng/mL. It should be noted herein that differentiation to anterior mesoderm fates required higher Activin A concentrations (e.g., at least about 100 ng/mL), while differentiation to posterior hemogenic endothelium requires lower Activin A concentrations (e.g., less than 100 ng/mL, for example, 0-100 ng/mL, 0-75 ng/mL, 0-50 ng/mL, 0-25 ng/mL, or any range therebetween).

In another embodiment of this aspect and all other aspects provided herein, the Activin A is present in a concentration of about 100 ng/mL.

In another embodiment of this aspect and all other aspects provided herein, the BMP4 is present in defined medium at a concentration less than 10 ng/mL.

In another embodiment of this aspect and all other aspects provided herein, the BMP4 is present in a concentration of about 5 ng/mL.

In another embodiment of this aspect and all other aspects provided herein, Activin A is added to the culture of human pluripotent stem cells at a first time point, and BMP4 is added to the culture at a second time point, 12-24 hours after the first time point.

In another embodiment of this aspect and all other aspects provided herein, Activin A-containing medium is replaced with BMP4-containing medium at the second time point.

In another embodiment of this aspect and all other aspects provided herein, the Activin A and BMP4 are in RPMI medium, with B27 supplement lacking insulin. B27 supplement (see, e.g., Brewer, Brain Res. 494: 65-74 (1989)) is commercially available, e.g., from Thermo Fisher Scientific. In one embodiment, the B-27 supplement plus insulin is commercially available from Thermo Fisher Scientific (cat no 17504-044; serum free) and comprises the following ingredients: an anti-oxidant cocktail, insulin and vitamin A. The B-27 supplement minus insulin used herein is also commercially available from Thermo Fisher Scientific (cat no A18956-01; serum free).

In another embodiment of this aspect and all other aspects provided herein, the Activin A is in RPMI medium with B27 supplement lacking insulin and a soluble basement membrane preparation.

In another embodiment of this aspect and all other aspects provided herein, the method further comprises a step, after culturing in the presence of BMP4, of culturing the cells in defined medium comprising BMP4, basic Fibroblast Growth Factor (bFGF) and Vascular Endothelial Growth Factor (VEGF).

In another embodiment of this aspect and all other aspects provided herein, the defined medium comprising BMP4, bFGF and VEGF comprises 100 mM monothioglycerol (MTG), 100 mM L-glutamine, 50 mg/mL ascorbic acid, 10 µg/mL BMP4, 5 µg/mL bFGF and 300 µg/mL VEGF. It is contemplated that concentrations of these agents can vary somewhat without radically altering the direction or efficiency of endocardial endothelial differentiation, or for that matter, that certain variations in concentration may assist in promoting even higher efficiencies. Thus, it is contemplated that variation in the concentration of any one or more of monothioglycerol (MTG), L-glutamine, ascorbic acid, bFGF and/or VEGF can be tolerated and still efficiently provide endocardial endothelial cells. As but one example, variation in any one or more of monothioglycerol (MTG), L-glutamine, ascorbic acid, bFGF and/or VEGF by ±50% from the values noted above can also permit or promote differentiation along the endocardial endothelial lineage.

In another embodiment of this aspect and all other aspects provided herein, the pluripotent stem cells are cultured with Activin A for 12-20 hours, followed by culture with BMP4 for 20-28 hours, followed by culture in defined medium containing BMP4, bFGF and VEGF for 65-80 hours.

In another embodiment of this aspect and all other aspects provided herein, the method generates a culture comprising at least 60% endocardial endothelial cells, without the need for a cell sorting or enrichment step. In other embodiments of this aspect and all other aspects provided herein, the method generates a culture comprising at least 70%, at least 75%, at least 80%, at least 85%, at least 90%, at least 92%, at least 95%, at least 99% or even 99.9% endocardial endothelial cells, without the need for a cell sorting or enrichment step.

In another embodiment of this aspect and all other aspects provided herein, the endocardial endothelial cells are NFATc1+. In another embodiment of this aspect and all other aspects provided herein, the endocardial endothelial cells are $CDH13^{high}$ and/or $CD226^{high}$. In another embodiment of this aspect and all other aspects provided herein, the endocardial endothelial cells are enriched for expression of CDH13 and CD226.

In another embodiment of this aspect and all other aspects provided herein, less than 1% of the resulting cells are $CD43^+$ and $CD235a^+$.

In another embodiment of this aspect and all other aspects provided herein, the pluripotent stem cells are at a cell density of about $1.6 \times 10^5$ cells/cm$^2$ when the cells are contacted with Activin A. In other embodiments, the pluripotent stem cells are at a cell density of about $1.0 \times 10^5$ cells/cm$^2$, about $1.1 \times 10^5$ cells/cm$^2$, about $1.2 \times 10^5$ cells/cm$^2$, about $1.3 \times 10^5$ cells/cm$^2$, about $1.4 \times 10^5$ cells/cm$^2$, about $1.5 \times 10^5$ cells/cm$^2$, about $1.7 \times 10^5$ cells/cm$^2$, about $1.8 \times 10^5$ cells/cm$^2$, about $1.9 \times 10^5$ cells/cm$^2$, about $2.0 \times 10^5$ cells/cm$^2$, about $5 \times 10^5$ cells/cm$^2$, or about $1 \times 10^6$ cells/cm$^2$.

Another aspect provided herein relates to a method of generating endocardial endothelial cells from human pluripotent stem cells, the method comprising polarizing differentiation potential towards cardiogenic, rather than hemogenic mesoderm, at the onset of treatment of pluripotent stem cells for differentiation, by contacting the cells in monolayer culture with defined medium comprising Activin A for 12-20 hours, followed by contacting the cells with defined medium comprising BMP4 for 20-28 hours, before treating the resulting cells for differentiation to endocardial endothelial cells, wherein the method generates a culture comprising at least 60% endocardial endothelial cells without the need for a cell sorting step.

In one embodiment of this aspect and all other aspects provided herein, the Activin A is present in defined medium in a concentration of at least about 100 ng/mL. In other embodiments, the Activin A concentration can vary as discussed herein above for the promotion of endocardial endothelium.

In another embodiment of this aspect and all other aspects provided herein, the Activin A is present in a concentration of about 100 ng/mL.

In another embodiment of this aspect and all other aspects provided herein, the BMP4 is present in defined medium at a concentration less than 10 ng/mL. In other embodiments, the BMP4 concentration can vary as discussed herein above for the promotion of endocardial endothelium.

In another embodiment of this aspect and all other aspects provided herein, the BMP4 is present in a concentration of about 5 ng/mL.

In another embodiment of this aspect and all other aspects provided herein, treating the cells for differentiation to endocardial endothelial cells comprises culturing them in defined medium comprising BMP4, bFGF and VEGF.

In another embodiment of this aspect and all other aspects provided herein, the defined medium comprising BMP4, bFGF and VEGF comprises 100 mM monothioglycerol (MTG), 100 mM L-glutamine, 50 mg/mL ascorbic acid, 10 µg/mL BMP4, 5 µg/mL bFGF and 300 µg/mL VEGF. It is contemplated that these concentrations can vary as noted above without substantial impact on the efficiency or direction of differentiation.

In another embodiment of this aspect and all other aspects provided herein, the endocardial endothelial cells are NFATc1+.

In another embodiment of this aspect and all other aspects provided herein, less than 1% of the resulting cells are $CD43^+$ and $CD235a^+$. In another embodiment of this aspect and all other aspects provided herein, the endocardial endothelial cells are enriched for expression of CDH13 and CD226.

Another aspect provided herein relates to a method of promoting wound healing on or in a subject in need thereof, the method comprising administering a human endocardial endothelial cell derived from a human pluripotent stem cell to a wound. As used herein, the term "wound healing" refers to any injury to the body that results in loss of cell and is followed by inflammation and repair. That is, the term "wound healing" encompasses a variety of injuries and not just skin injuries, as is traditionally understood as the primary site of wound healing mechanisms. In one embodiment, the endocardial endothelial cell is administered in or on a scaffold material.

In one embodiment of this aspect and all other aspects provided herein, the pluripotent stem cell is autologous to the subject.

In another embodiment of this aspect and all other aspects provided herein, the pluripotent stem cell is an induced pluripotent stem cell.

In some embodiments, it is advantageous that an induced pluripotent stem cell not include integrated exogenous nucleic acids, because insertional mutagenesis can lead to unwanted effects, including, but not limited to tumorigenesis. However, approaches are known that minimize or avoid the integration of nucleic acids encoding reprogramming factors, using, for example, RNA or protein to effect reprogramming of somatic cells to induced pluripotent stem cells. Thus, in another embodiment of this aspect and all other aspects provided herein, the induced pluripotent stem cell carries no exogenous nucleic acid sequences.

In another embodiment of this aspect and all other aspects provided herein, the human endocardial endothelial cell is prepared by a method comprising contacting the pluripotent stem cells in monolayer culture with defined medium comprising Activin A for 12-20 hours, followed by contacting the cells with defined medium comprising BMP4 for 20-28 hours, before treating the resulting cells for differentiation to endocardial endothelial cells by culturing them in defined medium comprising BMP4, bFGF and VEGF.

Also provided herein, in another aspect, is a method of promoting angiogenesis in a subject in need thereof, the method comprising administering a human endocardial endothelial cell derived from a human pluripotent stem cell.

In another embodiment of this aspect and all other aspects provided herein, the pluripotent stem cell is autologous to the subject.

In another embodiment of this aspect and all other aspects provided herein, the pluripotent stem cell is an induced pluripotent stem cell.

In another embodiment of this aspect and all other aspects provided herein, the induced pluripotent stem cell carries no exogenous nucleic acid sequences.

In another embodiment of this aspect and all other aspects provided herein, the human endocardial endothelial cell is prepared by a method comprising contacting the pluripotent stem cells in monolayer culture with defined medium comprising Activin A for 12-20 hours, followed by contacting the cells with defined medium comprising BMP4 for 20-28 hours, before treating the resulting cells for differentiation to endocardial endothelial cells by culturing them in defined medium comprising BMP4, bFGF and VEGF.

Another aspect provided herein relates to a method of producing cardiac valve interstitial cells, comprising contacting endocardial endothelial cells derived from a human pluripotent stem cell with a TGF-β pathway agonist and/or an agent that induces epithelial to mesenchymal transition. Some exemplary factors that can induces epithelial to mesenchymal transition include, but are not limited to, VEGF, BMP2 and agents that activate Notch signaling.

In one embodiment of this aspect and all other aspects provided herein, the method further comprises culturing the cells in or on an extracellular matrix preparation or a synthetic 3-dimensional material.

In another embodiment of this aspect and all other aspects provided herein, the cardiac valve interstitial cell has increased expression of SNAI1, SNAI2, TWIST1, smooth muscle actin (SMA), vimentin, NCAM/CD56 and/or collagens 1 and 3 as compared to a cell from which it is derived. SNAI1, SNAI2, TWIST1 are transiently upregulated in the valve interstitial cell population. Without wishing to be bound by theory, SMA activation may depend on substrate stiffness and the cytokine environment.

In another embodiment of this aspect and all other aspects provided herein, the cardiac valve interstitial cell has decreased expression of VE-cadherin and CD31 as compared to a cell from which it is derived.

In another aspect, provided herein is a composition comprising a human endocardial endothelial cell in or on a scaffold. Scaffolds are discussed herein below, but in one embodiment, the combination cell/scaffold composition includes a scaffold, comprised, for example, of a polymer or copolymer, or a scaffold matrix. The polymer or matrix can be one that occurs in nature, e.g., collagen, fibrin or a polysaccharide. In one embodiment, the polymer or matrix is synthetic or man made. In another embodiment, the polymer or matrix is one that may occur in nature, yet does not generally occur with human endocardial endothelial cells.

Also provided herein, in another aspect, is a human mesodermal stem cell comprising a heterologous sequence encoding a reporter polypeptide, operably linked to sequences that regulate the NFAT1c gene.

In one embodiment of this aspect and all other aspects provided herein, the reporter polypeptide comprises a fluorescent polypeptide.

In another embodiment of this aspect and all other aspects provided herein, the cell is polarized to form cardiogenic mesoderm.

In another embodiment of this aspect and all other aspects provided herein, is derived from an induced pluripotent stem cell.

In another embodiment of this aspect and all other aspects provided herein, the heterologous sequence is operably linked to sequences that regulate the endogenous NFAT1c gene.

In some embodiments, the endocardial endothelial cells and differentiated valve cells thereof can be used in screening assays, for example, to test a candidate agent (e.g., a potential cardiovascular agent) for effects of the agent.

BRIEF DESCRIPTION OF THE FIGURES

FIG. 3A, Effect of cell density on cardiomyocyte differentiation efficiency based on FACS analyses of cTnT+ cells on day 14. FIG. 3B, Immunohistochemistry of cardiomyocytes at day 14 based on staining for the transcription factor Nkx2-5, the myofilament protein α-actinin, and the intercalated disk protein connexin-43. n≥3 per sample.

FIGS. 4A-4B, Cells were differentiated into EECs (FIG. 4A) and HECs (FIG. 4B) and tested for efficiency on the basis of density at the onset of differentiation and amount of VEGF exposure at day 2. Cells were phenotyped (FIG. 4C) on day 5 of differentiation for KDR/CD34, VE-cadherin, and CD31 by FACS analysis. These data show a clear dependency of differentiation on the basis of VEGF stimulation but much less effect of density at the onset of differentiation. n≥3 per sample.

FIG. 5A, Representative FACS plot of day 5 EECs and HECs showing differences in primitive hematopoietic activity indicated by CD43/CD235a double positive cells. FIG. 5B, Representative images of primitive erythroid (Ery-P) and macrophage (Mac) colonies in methylcellulose colony forming assays. Images are magnified for EryP (100×) and Mac (50×) to show details of colony morphology.

FIGS. 6A-6C. Differentiation into definitive endothelial cells. FIG. 6A, Analysis of EC differentiation using different matrix substrates showing no effect on differentiation efficiency using gelatin, fibronectin, or MATRIGEL™. FIG.

6B, Staining of EECs and HECs in a monolayer for CD31. FIG. 6C, Confocal z-stack showing de novo lumen formation in collagen gel as seen in both EECs and HECs. Orthogonal slices below each z-stack show lumen formation. n≥3 per sample.

FIGS. 7A-7C, Cells were differentiated into cardiomyocytes based on cTnT+ cells on day 14 of differentiation (FIG. 7A), EECs and HECs based KDR+/CD34+ cells on day 5 (FIG. 7B), and definitive EECs and HECs based on CD31+ cells on day 14 of differentiation (FIG. 7C). n≥3 per sample.

FIG. 8A, Different cell densities tested throughout this protocol to assess density-dependency of differentiation into cardiac and endothelial lineages. FIGS. 8B & 8C, Phenotyping changes that are observed as cells transition from pluripotency to day 1, remaining in close contact during exposure to Activin A (FIG. 8B) and then undergo near single cell dispersion across the plate during exposure to BMP4 and progression to mesoderm on day 2 (FIG. 8C).

FIG. 9A, Schematic diagram of time course of directed differentiation and days (FIGS. 9A-9F) in which changes were made as outlined in FIGS. 9B-9H to optimize conditions for differentiation into endothelium. FIGS. 9B-9H, Flow cytometry analysis for the cardiac progenitor marker KDR+/PDGFRα+ and the endothelial marker KDR+/CD31+ (FIGS. 9B-9H) at day 5 of differentiation. Manipulation of conditions at time points in FIGS. 9A-9F are described to the right of each panel.

FIG. 10A, Schematic of differentiation timeline. FIG. 10B, Exposure to VEGF continuously starting on day 1 of differentiation vs. subsequent days as it impacts efficiency of endothelial cell production on day 5 by FACS analysis for KDR and CD34. FIG. 10C, Exposure to VEGF for 24 hour increments starting on day 1 vs. subsequent days as it impacts efficiency of endothelial cell production on day 5 by FACS analysis for KDR and CD34.

DETAILED DESCRIPTION

Figure 1:
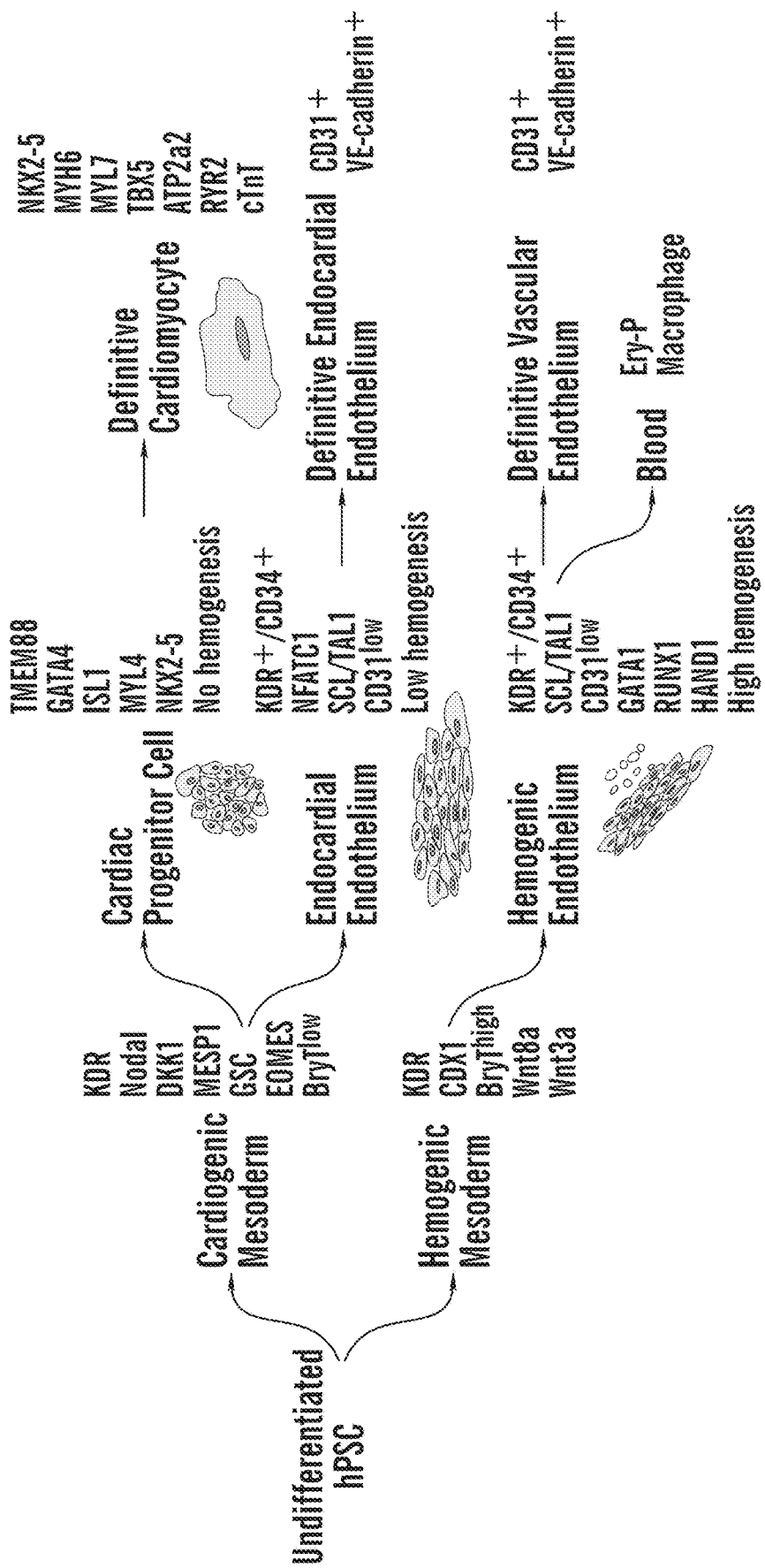
FIG. 1 Lineage fate choices in cardiovascular development. Schematic outlining major cell fate decisions from pluripotency to definitive cardiac and vascular cell types. Molecular markers and functional characteristics of each population are noted for each population.

The compositions and methods described herein are related, in part, to the discovery of a protocol that permits the efficient differentiation of human pluripotent stem cells to e.g., endocardial endothelial cells and cardiomyocytes. The methods described herein permit the generation of cardiomyocytes and endocardial endothelial cells in a greater number than previously achieved and advantageously does not require sorting of cells. Such cells can be used in the treatment and/or prevention of heart disease, injury to the heart, wound healing and other diseases/disorders that would benefit from increased blood vessel growth. Endocardial endothelial cells also have particular utility in promoting angiogenesis, wound healing, tissue engineering, and treatment of heart valve disorders.

The following describes methods for preparing endocardial endothelial cells and considerations necessary for those of skill in the art to make and use them.

Definitions

As used herein the term "human stem cell" refers to a human cell that can self-renew and differentiate to at least one cell type. The term "human stem cell" encompasses human stem cell lines, human-derived iPS cells, human embryonic stem cells, human pluripotent cells, human multipotent stem cells, amniotic stem cells, placental stem cells, or human adult stem cells.

As used herein, the term "multipotent" refers to the ability of a cell to differentiate into a plurality of different phenotypes. Multipotent cells can generally only differentiate into cells of a single germ layer lineage. This is in contrast to pluripotent cells which can, by definition, differentiate into cells of all three germ layers. Pluripotent cells are characterized primarily by their ability to differentiate to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. A pluripotent cell typically has the potential to divide in vitro for a long period of time, e.g., greater than one year or more than 30 passages.

As used herein, the term "positive for" when referring to a cell positive for a marker (e.g., NFATC1 positive endocardial endothelial cells) means that a cell surface marker is detectable above background levels on the cell using immunofluorescence microscopy or flow cytometry methods, such as fluorescence activated cell sorting (FACS). Alternatively, the terms "positive for" or "expresses a marker" means that expression of mRNA encoding a cell surface or intracellular marker is detectable above background levels using RT-PCR. The expression level of a cell surface marker or intracellular marker can be compared to the expression level obtained from a negative control (i.e., cells known to lack the marker) or by isotype controls (i.e., a control antibody that has no relevant specificity and only binds non-specifically to cell proteins, lipids or carbohydrates). Thus, a cell that "expresses" a marker (or is "positive for a marker") has an expression level detectable above the expression level determined for the negative control for that marker.

As used herein, the term "negative for" when referring to a cell negative for a marker (or the term "does not express") means that a cell surface marker cannot be detected above background levels on the cell using immunofluorescence microscopy or flow cytometry methods, such as fluorescence activated cell sorting (FACS). Alternatively, the terms "negative" or "does not express" means that expression of the mRNA for an intracellular marker or cell surface marker cannot be detected above background levels using RT-PCR. The expression level of a cell surface marker or intracellular marker can be compared to the expression level obtained from a negative control (i.e., cells known to lack the marker) or by isotype controls (i.e., a control antibody that has no relevant specificity and only binds non-specifically to cell proteins, lipids or carbohydrates). Thus, a cell that "does not express" a marker appears similar to the negative control with respect to that marker.

As used herein, the phrase "cell is proliferative" refers to the ability of a stem cell to self-renew. Self-renewal can occur by either of two major mechanisms. Stem cells can divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only.

As used herein, the term "capacity to differentiate" refers to the ability of a stem cell, progenitor cell, pluripotent cell, or multipotent cell to differentiate into a subset of more differentiated cells. The term "capacity to differentiate" does not encompass moving backwards along the differentiation spectrum such that a cell is produced that comprises a greater differentiation capacity than the parent cell. That is, the term "capacity to differentiate" does not encompass re-programming methods to shift cells to a less differentiated state.

In the context of cell ontogeny, the term "differentiate", or "differentiating" is a relative term that indicates a "differentiated cell" is a cell that has progressed further down the developmental pathway than its precursor cell. Thus in some embodiments, a reprogrammed cell as this term is defined herein, can differentiate to lineage-restricted precursor cells (such as a human cardiac progenitor cell or mid-primitive streak cardiogenic mesoderm progenitor cell), which in turn can differentiate into other types of precursor cells further down the pathway (such as a tissue specific precursor such as a cardiomyocyte precursor), and then to an end-stage differentiated cell, which plays a characteristic role in a certain tissue type, and may or may not retain the capacity to proliferate further.

As used herein, the terms "dedifferentiation" or "reprogramming" or "retrodifferentiation" refer to the process that generates a cell that re-expresses a more stem cell phenotype or a less differentiated phenotype than the cell from which it is derived. For example, a multipotent cell can be dedifferentiated to a pluripotent cell. That is, dedifferentiation shifts a cell backward along the differentiation spectrum of totipotent cells to fully differentiated cells. Typically, reversal of the differentiation phenotype of a cell requires artificial manipulation of the cell, for example, by expressing stem cell-specific mRNA and/or proteins. Reprogramming is not typically observed under native conditions in vivo or in vitro.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cells forming the body of an organism, as opposed to germline cells. Every cell type in the mammalian body—apart from the sperm and ova, the cells from which they are made (gametocytes) and undifferentiated stem cells—is a somatic cell: internal organs, skin, bones, blood, and connective tissue are all substantially made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for reprogramming a differentiated cell (e.g., to generate an iPSC) can be performed both in vivo and in vitro (where in vivo is practiced when a differentiated cell is present within a subject, and where in vitro is practiced using an isolated differentiated cell maintained in culture).

As used herein, the term "adult cell" refers to a cell found throughout the body after embryonic development.

As used herein, the term "endocardial endothelial cells," in part, refers to cells that are substantially similar to the endothelial cells that line the inside of the heart chambers or cardiac valves in vivo. Expression of NFATc1 is a hallmark of endocardial endothelial cells. An endocardial endothelial cell, as that term is used herein, is an endothelial cell that is committed to the cardiac lineage, and expresses CD31, VE-cadherin, and/or NFAT1c. In some embodiments, the endocardial endothelial cell is enriched for the expression of CDH13, CD226 and/or one or more of the genes listed in Table 6. In other embodiments, the endocardial endothelial cell lacks detectable expression of hemogenic or hematopoietic markers (i.e., blood forming cell markers), such as HAND1, GATA1, RUNX1, SCL/TAL1, and KDR/CD34. In one embodiment, the transcript level of NFAT1c is measured using qRT-PCR and is greater than 0.3 relative units when normalized to HPRT. In another embodiment, the transcript of NFAT1c is measured using qRT-PCR and is less than 0.8 relative units when normalized to HAND1. Functionally, in one embodiment an endocardial endothelial cell is capable of participating in or promoting angiogenesis, particularly coronary angiogenesis.

As used herein, the term "cardiac valve interstitial cell" refers to a cell that is substantially similar to a valve interstitial cell in vivo, which are the most prevalent cells in the heart valve and are found in all three layers of the valve—the fibrosa, the spongiosa, and the ventricularis. Functionally, a cardiac valve interstitial cell is responsible for maintaining the structural integrity of the valve. In one embodiment, a cardiac valve interstitial cell, as that term is used herein, expresses vimentin, NCAM/CD56, SNAI1, SNAI, TWIST 1, smooth muscle actin (SMA) and/or collagens 1 and 3. It is important to note that the expression of SNAI1/2 and TWIST1 are transiently upregulated in cardiac valve interstitial cells and should not be used alone as a positive marker for such cells. In another embodiment, a cardiac valve interstitial cell exhibits reduced or down-regulated expression of endothelial markers, such as VE-cadherin and CD31 relative to endocardial endothelial cells.

The term "isolated cell" as used herein refers to a cell that has been removed from an organism in which it was originally found, or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched. In some embodiments, the isolated population is an isolated population of human cardiac progenitor cells or their differentiated progeny, e.g., a substantially pure population of human cardiac progenitor cells or their differentiated progeny as compared to a heterogeneous population of cells comprising human cardiac progenitor cells and cells from which the human cardiac progenitor cells were derived.

The term "substantially pure," with respect to a particular cell population, refers to a population of cells that is at least about 75%, preferably at least about 85%, more preferably at least about 90%, and most preferably at least about 95% pure, with respect to the cells making up a total cell population. That is, the terms "substantially pure" or "essentially purified," with regard to a population of endocardial endothelial cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not endocardial endothelial cells as defined by the terms herein.

The terms "enriching" or "enriched" are used interchangeably herein and mean that the yield (fraction) of cells of one type, such as human endocardial endothelial cell compositions and cells for use in the methods described herein, is increased by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, or by at least 75%, over the fraction of cells of that type in the starting biological sample, culture, or preparation.

As used herein, "proliferating" and "proliferation" refer to an increase in the number of cells in a population (growth) by means of cell division. Cell proliferation is generally understood to result from the coordinated activation of multiple signal transduction pathways in response to the environment, including growth factors and other mitogens. Cell proliferation can also be promoted by release from the actions of intra- or extracellular signals and mechanisms that block or negatively affect cell proliferation.

The terms "renewal" or "self-renewal" or "proliferation" are used interchangeably herein, and refers to a process of a cell making more copies of itself (e.g. duplication) of the cell. In some embodiments, cardiac progenitor cells are capable of renewal of themselves by dividing into the same undifferentiated cells (e.g. as determined by measuring the presence of absence of one or more cell surface or other markers) over long periods, and/or many months to years. In some instances, proliferation refers to the expansion of cardiac progenitor cells by the repeated division of single cells into two identical daughter cells.

The term "separation" or "selection" as used herein refers to isolating different cell types into one or more populations and collecting the isolated population as a target cell population which is enriched, for example, in a specific target stem cell. Selection can be performed using positive selection, whereby a target enriched cell population is retained, or negative selection, whereby non-target cell types are discarded (thereby enriching for desired target cell types in the remaining cell population).

The term "positive selection" as used herein refers to selection of a desired cell type by retaining the cells of interest. In some embodiments, positive selection involves the use of an agent to assist in retaining the cells of interest, e.g., use of a positive selection agent such as an antibody which has specific binding affinity for a surface antigen on the desired or target cell. In some embodiments, positive selection can occur in the absence of a positive selection agent, e.g., in a "touch-free" or closed system, for example, where positive selection of a target cell type is based on any of cell size, density and/or morphology of the target cell type.

The term "negative selection" as used herein refers to selection of undesired or non-target stem cells for depletion or discarding, thereby retaining (and thus enriching) the desired target cell type. In some embodiments, negative selection involves the use of an agent to assist in selecting undesirable cells for discarding, e.g., use of a negative selection agent such as a monoclonal antibody which has specific binding affinity for a surface antigen on unwanted or non-target cells. In some embodiments, negative selection does not involve a negative selection agent. In some embodiments, negative selection can occur in the absence of a negative selection agent, e.g., in a "touch-free" or closed system, for example, where negative selection of an undesired (non-target) cell type to be discarded is based on any of cell size, density and/or morphology of the undesired (non-target) cell type.

The term "marker" as used herein is used to describe the characteristics and/or phenotype of a cell. Markers can be used for selection of cells comprising characteristics of interest and can vary with specific cells. Markers are characteristics, whether morphological, functional or biochemical (enzymatic) characteristics of the cell of a particular cell type, or molecules expressed by the cell type. In one aspect, such markers are proteins. Such proteins can possess an epitope for antibodies or other binding molecules available in the art. However, a marker can consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers can be detected by any method available to one of skill in the art. Markers can also be the absence of a morphological characteristic or absence of proteins, lipids etc. Markers can be a combination of a panel of unique characteristics of the presence and/or absence of polypeptides and other morphological characteristics. In one embodiment, the marker is a cell surface marker. Exemplary cell surface markers expressed on pluripotent cardiac lineage cells and their progeny at different stages of differentiation include, but are not limited to, the markers in Table 6 or FIG. 1.

In some embodiments, the absence of a cell surface marker can be used to distinguish e.g., a cardiogenic mesoderm cell or endocardial endothelial cell from a cell of another lineage (e.g., a hematopoietic cell or "blood-forming" cell). Exemplary cell surface markers that are absent on cardiogenic mesoderm cells and permit identification/selection from hemogenic mesoderm cells include, but are not limited to, KDR/CD34, SCL/TAL1, GATA1, RUNX1, HAND1, CDX1, WNT8a and WNT3a. Conversely, exemplary cell surface markers on hemogenic mesoderm cells that can be used to remove hemogenic mesoderm cells include, but are not limited to, KDR/CD34, SCL/TAL1, GATA1, RUNX1, HAND1, CDX1, WNT8a and WNT3a. One of skill in the art will recognize that a cell surface marker can be present at a particular point in development or in a particular cardiac progenitor cell type but can be lost as the cell is differentiated further down a committed lineage of cells. For example, KDR is expressed in cardiogenic mesoderm cells, but is lost upon differentiation to a cardiac progenitor cell. Thus, a cell surface marker can be used in combination with a positive selection strategy for endocardial endothelial cells and also used in combination with a negative selection strategy for other cells (e.g., hematopoietic cells).

As used herein, the term "scaffold" refers to a structure, comprising a biocompatible material that provides a surface suitable for adherence and proliferation of cells. A scaffold can further provide mechanical stability and support. A scaffold can be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

As used herein, the term "implantable in a subject" refers to any non-living (e.g., acellular) implantable structure that upon implantation does not generate an appreciable immune response in the host organism. Thus, an implantable structure should not for example, be or contain an irritant, or contain LPS etc.

As used herein, the term "biodegradable" refers to the ability of a scaffold to degrade under physiological conditions, for example, under conditions that do not adversely affect cell viability of the delivered cells or cells in vivo. Such biodegradable scaffolds will preferably not be or contain an irritant or an allergen that can cause a systemic reaction in the subject to which the composition has been implanted. In some embodiments, biodegradable means that the scaffold can be metabolized and the metabolites cleared from the subject by physiological excretion mechanisms (e.g., urine, feces, liver detoxification etc.).

As used herein, the term "treating" includes reducing or alleviating at least one adverse effect or symptom of a condition, disease or disorder. For example, the term "treating" and "treatment" refers to administering to a subject an effective amount of a composition, e.g., an effective amount of a composition comprising a population of e.g., cardiac progenitor cells, cardiomyocytes, endocardial endothelial cells etc. so that the subject has a reduction in at least one symptom of the disease or an improvement in the disease, for example, beneficial or desired clinical results (e.g., improved cardiac function in an infarcted area of the heart, improved heart valve function etc.). For purposes of this disclosure, beneficial or desired clinical results include, but are not limited to, alleviation of one or more symptoms, diminishment of extent of disease, disease stabilization (e.g., not worsening), delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment can improve the disease condition, but may not be a complete cure for the disease. In some embodiments, treatment can include prophylaxis. However, in alternative embodiments, treatment does not include prophylaxis.

"Treatment" of a cardiac disorder, a cardiac disease, or a cardiac injury (e.g., myocardial infarction) as referred to herein refers to therapeutic intervention that enhances cardiac function and/or repairs heart valves and/or enhances blood vessel growth in a treated area, thus improving the function of e.g., the heart and/or promotes blood vessel growth. That is, cardiac "treatment" is oriented to the function of the heart (e.g., improved heart valve function, enhanced function within an infarcted area), and/or other site treated with the compositions described herein. A therapeutic approach that prevents heart valve dysfunction, restores heart valve function, induces blood vessel growth and/or improves the function of the heart by at least 10%, and preferably by at least 20%, 30%, 40%, 50%, 75%, 90%, 100% or more, e.g., 2-fold, 5-fold, 10-fold or more, up to and including full function, relative to such function prior to such therapy is considered effective treatment. Effective treatment need not cure or directly impact the underlying cause of the heart disease or disorder to be considered effective treatment.

"Treatment" of, e.g., a wound refers to therapeutic intervention that promotes or enhances healing of a wound relative to the healing that occurs in the absence of such treatment. Wound healing can be quantitated, for example, in terms of the time necessary to achieve a predetermined degree of wound closure, for example. Assays for measuring wound healing in animal models that use a uniform type and size of wound can be applied to evaluate the wound-healing effects of a composition as described herein.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "prevention" or "preventing," when used in reference to a disease, disorder or symptoms thereof, refers to a reduction in the likelihood that an individual will develop a disease or disorder, e.g., heart valve dysfunction from infective endocarditis, as but one example. The likelihood of developing a disease or disorder is reduced, for example, when an individual having one or more risk factors for a disease or disorder either fails to develop the disorder or develops such disease or disorder at a later time or with less severity, statistically speaking, relative to a population having the same risk factors and not receiving treatment as described herein. The failure to develop symptoms of a disease, or the development of reduced (e.g., by at least 10% on a clinically accepted scale for that disease or disorder) or delayed (e.g., by days, weeks, months or years) symptoms is considered effective prevention.

As used herein, the term "induced to differentiate" refers to a chemical/biological treatment, a physical environment or a genetic modification that is conducive to the formation of more differentiated cells (e.g., endocardial endothelial cells) from pluripotent or multipotent stem cells. Differentiation can be assessed by the appearance of distinct cell-type specific markers or by the loss of stem cell specific markers, or both.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Embryonic Stem Cells

Stem cells are cells that retain the ability to renew themselves through mitotic cell division and can differentiate into a diverse range of specialized cell types. Three broad types of mammalian stem cells include: embryonic stem (ES) cells that are found in blastocysts, induced pluripotent stem cells (iPSCs) that are reprogrammed from somatic cells, and adult stem cells that are found in adult tissues. Other sources of pluripotent stem cells can include amnion-derived or placental-derived stem cells. In a developing embryo, stem cells can differentiate into all of the specialized embryonic tissues. In adult organisms, stem cells and progenitor cells act as a repair system for the body, replenishing specialized cells, but also maintain the normal turnover of regenerative organs, such as blood, skin or intestinal tissues. Pluripotent stem cells can differentiate into cells derived from any of the three germ layers.

Stem cells are classified by their developmental potential as: (1) totipotent, which is able to give rise to all embryonic and extra-embryonic cell types; (2) pluripotent, which is able to give rise to all embryonic cell types, i.e., endoderm, mesoderm, and ectoderm; (3) multipotent, which is able to give rise to a subset of cell lineages, but all within a particular tissue, organ, or physiological system (for example, cardiac mesoderm cells can produce progeny that include cardiac progenitor cells (self-renewal) and the cell types and elements (e.g., cardiomyocytes, endocardial endothelial cells) that are normal components of the heart); (4) oligopotent, which is able to give rise to a more restricted subset of cell lineages than multipotent stem cells; and (5) unipotent, which is able to give rise to a single cell lineage (e.g., spermatogenic stem cells).

Provided herein are methods of generating several human cardiac stem/progenitor cells (e.g., cardiac progenitor cells, endocardial endothelial cells, cardiomyocytes and definitive endocardial endothelial cells) from both embryonic stem cells and induced pluripotent stem cells. In one embodiment, methods of generating endocardial endothelial cells are provided herein. In one embodiment, the methods provided herein relate to generation of human cardiogenic cells and/or endocardial endothelial cells from embryonic stem cells. Alternatively, in some embodiments, the methods provided herein do not encompass generation of human cardiogenic cells and/or endocardial endothelial cells from cells taken from a viable human enbryo.

Embryonic stem cells and methods of their retrieval are well known in the art and are described, for example, in Trounson A O (Reprod Fertil Dev (2001) 13: 523), Roach M L (Methods Mol Biol (2002) 185: 1), and Smith A G (Annu Rev Cell Dev Biol (2001) 17:435). The term "embryonic stem cell" is used to refer to the pluripotent stem cells of the inner cell mass of the embryonic blastocyst (see e.g., U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235,970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

Cells derived from embryonic sources can include embryonic stem cells or stem cell lines obtained from a stem cell bank or other recognized depository institution. Other means of producing stem cell lines include methods comprising the use of a blastomere cell from an early stage embryo prior to formation of the blastocyst (at around the 8-cell stage). Such techniques correspond to the pre-implantation genetic diagnosis technique routinely practiced in assisted reproduction clinics. The single blastomere cell is co-cultured with established ES-cell lines and then separated from them to form fully competent ES cell lines.

Embryonic stem cells are considered to be undifferentiated when they have not committed to a specific differentiation lineage. Such cells display morphological characteristics that distinguish them from differentiated cells of embryo or adult origin. Undifferentiated embryonic stem (ES) cells are easily recognized by those skilled in the art, and typically appear in the two dimensions of a microscopic view in colonies of cells with high nuclear/cytoplasmic ratios and prominent nucleoli. In some embodiments, the human cardiac progenitor cells described herein are not derived from embryonic stem cells or any other cells of embryonic origin.

Adult stem cells are stem cells derived from tissues of a post-natal or post-neonatal organism or from an adult organism. An adult stem cell is structurally distinct from an embryonic stem cell not only in markers it does or does not express relative to an embryonic stem cell, but also by the presence of epigenetic differences, e.g. differences in DNA methylation patterns.

Induced Pluripotent Stem Cells (iPSCs)

In some embodiments, the human cardiogenic cells, cardiomyocytes and/or endocardial endothelial cells described herein are derived from isolated pluripotent stem cells. An advantage of using iPSCs is that the cells can be derived from the same subject to which the desired human cardiac or cardiogenic cells are to be administered. That is, a somatic cell can be obtained from a subject, reprogrammed to an induced pluripotent stem cell, and then re-differentiated into a human cardiogenic mesoderm cell, a cardiomyocyte and/or an endocardial endothelial cell to be administered to the subject (e.g., autologous cells). Since the cardiogenic progenitors or their differentiated progeny are essentially derived from an autologous source, the risk of engraftment rejection or allergic responses is reduced compared to the use of cells from another subject or group of subjects. In some embodiments, the cardiogenic progenitors and/or endocardial endothelial cells are derived from non-autologous sources. In addition, the use of iPSCs negates the need for cells obtained from an embryonic source. Thus, in one embodiment, the stem cells used in the disclosed methods are not embryonic stem cells.

Although differentiation is generally irreversible under physiological contexts, several methods have been developed in recent years to reprogram somatic cells to induced pluripotent stem cells. Exemplary methods are known to those of skill in the art and are described briefly herein below.

As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. However, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character when differentiated cells are placed in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain embodiments described herein, reprogramming of a differentiated cell (e.g., a somatic cell) causes the differentiated cell to assume an undifferentiated state with the capacity for self-renewal and differentiation to cells of all three germ cell lineages. The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent.

The specific approach or method used to generate pluripotent stem cells from somatic cells (broadly referred to as "reprogramming") is not critical to the claimed invention. Thus, any method that re-programs a somatic cell to the pluripotent phenotype would be appropriate for use in the methods described herein.

Reprogramming methodologies for generating pluripotent cells using defined combinations of transcription factors are known in the art. Yamanaka and Takahashi converted mouse somatic cells to ES cell-like cells with expanded developmental potential by the direct transduction of Oct4, Sox2, Klf4, and c-Myc (Takahashi and Yamanaka, 2006). iPSCs resemble ES cells as they restore the pluripotency-associated transcriptional circuitry and much of the epigenetic landscape. In addition, mouse iPSCs satisfy all the standard assays for pluripotency: specifically, in vitro differentiation into cell types of the three germ layers, teratoma formation, contribution to chimeras, germline transmission (Maherali and Hochedlinger, 2008), and tetraploid complementation (Woltjen et al., 2009).

Subsequent studies have shown that human iPS cells can be obtained using similar transduction methods (Lowry et al., 2008; Park et al., 2008; Takahashi et al., 2007; Yu et al., 2007b), and the transcription factor trio, OCT4, SOX2, and NANOG, has been established as the core set of transcription factors that govern pluripotency (Jaenisch and Young, 2008). The production of iPS cells can be achieved by the introduction of nucleic acid sequences encoding stem cell-associated genes into an adult, somatic cell, historically using viral vectors.

iPS cells can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 2010 Nov. 5; 7(5):618-30). Reprogramming can be achieved by introducing a combination of nucleic acids encoding stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and LIN28. In one embodiment, reprogramming using the methods and compositions described herein can further comprise introducing one or more of Oct-3/4, a member of the Sox family, a member of the Klf family, and a member of the Myc family to a somatic cell. In one embodiment, the methods and compositions described herein further comprise introducing one or more of each of Oct 4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors.

The efficiency of reprogramming (i.e., the number of reprogrammed cells) derived from a population of starting cells can be enhanced by the addition of various small molecules as shown by Shi, Y., et al (2008) Cell-Stem Cell 2:525-528, Huangfu, D., et al (2008) Nature Biotechnology 26(7):795-797, and Marson, A., et al (2008) Cell-Stem Cell 3:132-135. Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from Biomol International, Fukasawa, Merck Biosciences, Novartis, Gloucester Pharmaceuticals, Aton Pharma, Titan Pharmaceuticals, Schering AG, Pharmion, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Somatic Cells for reprogramming: "Somatic cells," as that term is used herein, refers to any cells forming the body of an organism, excluding germline cells. Every cell type in the mammalian body—apart from the sperm and ova, the cells from which they are made (gametocytes) and undifferentiated stem cells—is a differentiated somatic cell. For example, internal organs, skin, bones, blood, and connective tissue are all made up of differentiated somatic cells.

Additional somatic cell types for use with the compositions and methods described herein include: a fibroblast (e.g., a primary fibroblast), a muscle cell (e.g., a myocyte), a cumulus cell, a neural cell, a mammary cell, a hepatocyte and a pancreatic islet cell. In some embodiments, the somatic cell is a primary cell line or is the progeny of a primary or secondary cell line. In some embodiments, the somatic cell is obtained from a human sample, e.g., a hair follicle, a blood sample, a biopsy (e.g., a skin biopsy or an adipose biopsy), a swab sample (e.g., an oral swab sample), and is thus a human somatic cell.

Some non-limiting examples of differentiated somatic cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. In some embodiments, a somatic cell can be a primary cell isolated from any somatic tissue including, but not limited to brain, liver, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used for generation of human cardiac progenitor cells and/or endocardial endothelial cells to be used in the therapeutic treatment of disease, it is desirable, but not required, to use somatic cells isolated from the patient being treated. For example, somatic cells involved in diseases, and somatic cells participating in therapeutic treatment of diseases and the like can be used. In some embodiments, a method for selecting the reprogrammed cells from a heterogeneous population comprising reprogrammed cells and somatic cells from which they were derived or generated from can be performed by any known means. For example, a drug resistance gene or the like, such as a selectable marker gene can be used to isolate the reprogrammed cells using the selectable marker as an index.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; β-III-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15; Stat3; Grb2; β-catenin, and Bmi1. Such cells can also be characterized by the down-regulation of markers characteristic of the somatic cell from which the induced pluripotent stem cell is derived.

Signaling Pathways for Differentiation

Provided herein are methods for generating cardiac cells (e.g., definitive cardiomyocytes and definitive endocardial endothelial cells) from human pluripotent cells (e.g., iPS cells, embryonic stem cells, amniotic stem cells, placental stem cells, or adult stem cells) through a step-wise differentiation approach. The methods are described herein in detail in the working Examples and are summarized briefly here.

Human pluripotent stem cells are differentiated and polarized into mesoderm cells representing the mid-primitive streak cardiogenic mesoderm and the posterior-primitive streak hemogenic mesoderm. Polarization of the pluripotent cells in vitro is performed, in part, by treatment with Activin A and then BMP4 as described herein. Cells representing the mid-streak mesoderm cells are used for further differentiation of cells committed to the cardiac lineage (e.g., cardiogenic mesoderm cells, cardiomyocytes, endocardial endothelial cells), while cells representing the posterior-streak mesoderm cells are used for differentiation to cells in the hematopoietic lineage (e.g., blood cells, vascular endothelial cells.) While any of these cell types, including the cardiac mesoderm-like cells and the hemogenic mesoderm-like cells, can be generated using the methods described herein and administered for the treatment of a given disease, the endocardial endothelial cells have particular utility in the treatment of a wide variety of cardiovascular and/or angiogenic diseases/disorders.

For example, endocardial endothelial cells are contemplated herein for use in (i) promoting angiogenesis wherever desired, (ii) wound healing, (iii) repair of cardiac structures, including valves, (iv) tissue engineering applications, and (iv) repairing cardiac tissue and/or function following a cardiac injury.

TGF-β signaling pathway modulation: In some embodiments, one or more TGF-β agonists (e.g., Activin A; BMP4) are used to promote a particular differentiation step of a pluripotent cell (e.g., polarization of mesoderm from a pluripotent cell). In such embodiments, an activating agent specific for TGF-β signaling can be a TGF-β polypeptide or an active fragment thereof, a fusion protein comprising a TGF-β polypeptide or an active fragment thereof, an agonist antibody to a TGF-β receptor, or a small molecule agonist of a TGF-β receptor.

The Transforming Growth Factor beta (TGF-β) signaling pathway is involved in many cellular processes in both the adult organism and the developing embryo including cell growth, cell differentiation, apoptosis, cellular homeostasis and other cellular functions. TGF-β superfamily ligands bind to a type II receptor, which recruits and phosphorylates a type I receptor. The type I receptor then phosphorylates receptor-regulated SMADs (R-SMADs) which then bind the coSMAD SMAD4. R-SMAD/coSMAD complexes accumulate in the nucleus where they act as transcription factors and participate in the regulation of target gene expression.

TGF-β1 is a prototypic member of a family of cytokines including the TGF-βs, activins, inhibins, bone morphogenetic proteins and Mullerian-inhibiting substance. Smad proteins are exemplary downstream signal transduction factors in the TGF-beta pathway and therefore, in some embodiments, can be activated directly to effect differentiation to a human cardiac cell progenitor phenotype (e.g., by treating a cell with an activator of a Smad protein). Exemplary Smad activators include, but are not limited to, Smad proteins or functional peptides or fragments thereof (e.g., Smad1, Smad5, Smad8), BMP2, BMP4, and Mullerian inhibiting substance (MIS). Activin ligands transduce signals in a manner similar to TGF-β ligands. Activins bind to and activate ALK receptors, which in turn phosphorylate Smad proteins such as Smad2 and Smad3. The consequent formation of a hetero-Smad complex with Smad4 results in the activin-induced regulation of gene transcription.

In some embodiments, the dose of TGF-β agonist (e.g., Activin A) used in the methods described herein (e.g., polarizing mesoderm) is between 100 ng/mL and 1000 ng/mL, between 100 ng/mL and 750 ng/mL, between 100 ng/mL and 500 ng/mL, between 100 ng/mL and 400 ng/mL, between 100 ng/mL and 300 ng/mL, between 100 ng/mL and 200 ng/mL, between 90 ng/mL and 150 ng/mL, or between 80 ng/mL and 120 ng/mL.

It is noted that treatment of pluripotent stem cells with Activin A at or below 50 ng/mL promotes differentiation along the hemogenic endothelium lineage, while treatment at 100 ng/mL biases towards the endocardial endothelial lineage. It is contemplated that Activin A treatment at concentrations less than 100 ng/mL but more than 50 ng/mL can also promote the endocardial endothelial lineage. For example, it is contemplated that at least 60 ng/mL, at least 70 ng/mL, at least 80 ng/mL, at least 90 ng/mL or at least 95 ng/mL can also promote differentiation along the endocardial endothelial lineage. In other embodiments, treatment of pluripotent stem cells along the posterior hemogenic endothelium lineage can be achieved by treatment with less than 50 ng/mL Activin A and in other embodiments, less than 40 ng/mL, less than 30 ng/mL, less than 20 ng/mL, less than 10 ng/mL, less than 5 ng/mL or even in the complete absence of Activin A.

In some embodiments, the dose of TGF-β agonist (e.g., Activin A) is e.g., at least 50 ng/mL, at least 75 ng/mL, at least 80 ng/mL, at least 85 ng/mL, at least 90 ng/mL, at least 95 ng/mL, at least 99 ng/mL, at least 100 ng/mL, at least 105 ng/mL, at least 110 ng/mL, at least 120 ng/mL, at least 150 ng/mL or more.

BMP Receptor Signaling Pathway Modulation

BMP2 and BMP4 both signal through the type I receptor, ALK3, while BMP7 binds to a separate type I receptor, ALK2. See e.g., von Bubnoff A et al., *Developmental Biology* (2001) 239:1-14; Chen D. et al., *Growth Factors* (2004) 22(4):233-241; Sieber C. et al., *Cytokine and Growth Factor Rev.* (2009) 20:343-355; and Miyazono K et al., *Journal of Biochemistry* (2010) 147(1):35-51.

Typically, BMP2 and BMP4 bind to a BMP receptor I/II complex, leading to phosphorylation of Smads 1/5/8, followed by formation of heterotrimeric complexes with Smad4. These complexes translocate to the nucleus and activate expression of target genes (von Bubnoff A et al., *Developmental Biology* (2001) 239:1-14; Chen D. et al., *Growth Factors* (2004) 22(4):233-241; Sieber C. et al., *Cytokine and Growth Factor Rev.* (2009) 20:343-355; and Miyazono K et al., *Journal of Biochemistry* (2010) 147(1):35-51). Besides Smad1/5/8-mediated transcription, BMP-induced receptor complexes can activate the mitogen-activated protein kinase (MAPK) pathway via ERK, JNK, or p38 (Kozawa O et al., *Journal of Cellular Biochemistry* 84:583-589).

BMP receptor pathway activation: In some embodiments, a BMP agonist is used with the methods described herein for polarization of the mesoderm and/or for differentiation of a cardiogenic progenitor cell.

In one embodiment, one or more BMP agonists are used to promote a particular differentiation step of a pluripotent cell. In such embodiments, an activating agent specific for BMP signaling can be a BMP polypeptide or an active fragment thereof, a fusion protein comprising a BMP polypeptide or an active fragment thereof, an agonist antibody to a BMP receptor, or a small molecule agonist of a BMP receptor. In one embodiment, the BMP used with the methods described herein is BMP4.

Treatment of Activin A-treated stem cells as described herein with a 40 ng/mL concentration of BMP4 biases cells towards the hemogenic lineage. To promote efficient differentiation along the endocardial endothelial lineage, lower concentrations of BMP are used. Thus, BMP4 can be used at a concentration of less than 30 ng/mL to promote differentiation along the endocardial endothelial cell lineage. Thus, BMP4 concentrations in the range of, for example, 0.5 to 30 ng/mL, 0.5 to 25 ng/mL, 0.5 to 20 ng/mL, 0.5 to 15 ng/mL, 0.5 to 10 ng/mL, 0.5 to 7.5 ng/mL, 0.5 to 5 ng/mL, 1 to 30 ng/mL, 1 to 25 ng/mL, 1 to 20 ng/mL, 1 to 15 ng/mL, 1 to 10 ng/mL, 1 to 5 ng/mL, 1 to 2.5 ng/mL, 5 to 30 ng/mL, 5 to 25 ng/mL, 5 to 20 ng/mL, 5 to 15 ng/mL, 5 to 10 ng/mL, 5 to 7.5 ng/mL, 7.5 to 30 ng/mL, 7.5 to 25 ng/mL, 7.5 to 20 ng/mL, 7.5 to 15 ng/mL, 7.5 to 10 ng/mL, 10 to 30 ng/mL, 10 to 25 ng/mL, 10 to 20 ng/mL, or 10-15 ng/mL, 15 to 30 ng/mL, 15 to 25 ng/mL, 15 to 20 ng/mL, 20 to 30 ng/mL, 20 to 25 ng/mL or 25-30 ng/mL are contemplated for use to promote differentiation along the endocardial endothelial lineage.

In other embodiments, the dosage range useful for BMP4 is a dose less than 25 ng/mL, less than 20 ng/mL, less than 15 ng/mL, less than 12 ng/mL, less than 10 ng/mL, less than 9 ng/mL, less than 8 ng/mL, less than 7 ng/mL, less than 6 ng/mL, less than 5 ng/mL, less than 4 ng/mL, less than 3 ng/mL, less than 2 ng/mL, less than 1 ng/mL, or about 0.5 ng/mL.

FGF activation: Fibroblast growth factors, or FGFs, are a family of growth factors that play a role in angiogenesis, wound healing, and embryonic development. FGFs and functional fragments or analogs thereof are useful for e.g., differentiating human hemogenic endothelial cells to e.g., definitive vascular endothelial cells, and blood cells, as described herein. bFGF can also be used to induce differentiation of endocardial endothelium to definitive endocardial endothelial cells.

FGFs are heparin-binding proteins, which interact with cell-surface-associated heparan sulfate proteoglycans to effect FGF signaling. At least 22 different members of the FGF family have been identified. FGF1, FGF2 (bFGF), FGF3, FGF4, FGF5, FGF6, FGF7, FGF8, FGF9, and FGF10 bind and effect signaling through fibroblast growth receptors (FGFR).

FGFs induce mitosis in a variety of cell types and also have regulatory, morphological, and endocrine effects. FGFs function throughout embryonic development and aid in mesoderm induction, antero-posterior patterning, limb development, neural induction and neural development. In one embodiment, a preferred FGF for use with the methods described herein is FGF2, which is also known in the art as Basic Fibroblast Growth Factor (bFGF).

In some embodiments, the dosage range useful for FGF2 is between 1 and 30 ng/mL, for example between 1 and 25 ng/mL, between 1 and 20 ng/mL, between 1 and 15 ng/mL, between 1 and 10 ng/mL, between 1 and 5 ng/mL, between 1.5 and 30 ng/mL, between 2 and 30 ng/mL, between 5 and 30 ng/mL, between 10 and 30 ng/mL, between 15 and 30 ng/mL, between 20 and 30 ng/mL, between 25 and 30 ng/mL, between 8 and 12 ng/mL, between 9 and 15 g/mL, between 9 and 11 ng/mL, or between 8 and 20 ng/mL.

In some embodiments the dose of FGF2 is e.g., at least 1 ng/mL, at least 2 ng/mL, at least 3 ng/mL, at least 4 ng/mL, at least 5 ng/mL, at least 6 ng/mL, at least 7 ng/mL, at least 8 ng/mL, at least 9 ng/mL, or more.

Wnt Antagonists: Provided herein are methods for directing mesoderm cells into the cardiac lineage by contacting a cell with a Wnt antagonist.

Without wishing to be bound by theory, Wnt proteins and their cognate receptors signal through at least two distinct intracellular pathways. The "canonical" Wnt signaling pathway, (referred to herein as the Wnt/β-catenin pathway) involves Wnt signaling via β-catenin to activate transcription through TCF-related proteins (van de Wetering et al. (2002) Cell 109 Suppl: S13-9; Moon et al. (2002) Science 296(5573): 1644-6). A non-canonical alternative pathway exists, in which Wnt activates protein kinase C (PKC), calcium/calmodulin-dependent kinase II (CaMKII), JNK and Rho-GTPases (Veeman et al. (2003) Dev Cell 5(3): 367-77), and is often involved in the control of cell polarity.

As used herein, the term "Wnt antagonist" or "Wnt inhibitor" refers to any agent that inhibits the Wnt/β-catenin pathway, or enhances the activity and/or expression of inhibitors of Wnt/β-catenin signaling, for example activators or enhancers of GSK-3β activity. A Wnt inhibitory agent as used herein can suppress the Wnt/β-catenin pathway at any point along the pathway, for example, but not limited to decreasing the expression and/or activity of Wnt, or β-catenin or Wnt dependent genes and/or proteins, and increasing the expression and/or activity of endogenous inhibitors of Wnt and/or β-catenin or increasing the expression and/or activity of endogenous inhibitors of components of the Wnt/β-catenin pathway, for example increasing the expression of GSK-3β or inhibiting the tankyrase enzyme.

Some non-limiting examples of Wnt antagonists include Wnt pathway inhibitor V (also known as (E)-4-(2,6-Difluorostyryl)-N,N-dimethylaniline), IWR-1 endo, IWP-2, CCT036477, XAV-939 (tankyrase inhibitor), and a peptide comprising the sequence t-Boc-NH-Met-Asp-Gly-Cys-Glu-Leu-CO2H.

In some embodiments, the dosage range useful for a Wnt antagonist (e.g. XAV-939) is between 0.5 and 5 μM, between 0.5 and 4 μM, between 0.5 and 3 μM, between 0.5 and 2 μM, between 0.5 and 1 μM, between 4 and 5 μM, between 3 and 5 μM, between 2 and 5 μM, between 1 and μM, between 0.5 and 2 μM, between 0.75 and 2 μM, between 0.9 μM and 2 μM, or any range therebetween.

In some embodiments the dose of a Wnt antagonist is e.g., at least 20 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 110 ng/mL, at least 120 ng/mL, at least 130 ng/mL, at least 140 ng/mL, at least 150 ng/mL, at least 160 ng/mL, at least 170 ng/mL, at least 180 ng/mL, at least 190 ng/mL, at least 200 ng/mL, or more.

Monitoring Differentiation of Endocardial Endothelial Cells

Provided herein are methods for differentiating or redifferentiating a pluripotent stem cell (e.g., a mesoderm cell, a mid-streak primitive mesoderm cell, an ES cell or an iPSC) to a human cardiogenic cell, and optionally further differentiating such human cardiogenic progenitor cells to cardiac progenitor cells, definitive cardiomyocytes, endocardial endothelium and/or definitive endocardial endothelial cells. These aspects are based on the novel discovery of a protocol for differentiation of pluripotent stem cells to a stem cell or progenitor cell committed to the cardiac and/or hematopoietic lineage. Such methods are exemplified in the Examples section herein. Also provided herein are compositions comprising human cardiac progenitor cells including cardiogenic mesoderm cells, cardiogenic progenitor cells, endocardial endothelium, definitive cardiomyocytes, and/or definitive endocardial endothelial cells. Alternatively, or in addition, the human cardiac lineage progenitor cell compositions described herein lack markers of hematopoietic or hemogenic cells, vascular endothelial cells, embryonic stem cells or induced pluripotent stem cells. In one embodiment of the methods described herein, one or more cell surface markers are used to determine the degree of differentiation along the spectrum of embryonic stem cells or iPSCs to e.g., fully differentiated cardiomyocytes or endocardial endothelial cells.

Cell surface markers, particularly stem cell surface markers, are useful with the methods and compositions described herein to identify the differentiation or dedifferentiation state of a cell. For example, during reprogramming of a somatic cell to an induced pluripotent stem cell the activation of stem cell markers can be used to confirm that the somatic cell has been dedifferentiated (either partially or completely). Alternatively, during differentiation of an ES cell or an iPSC to a human cardiogenic progenitor cell, the activation of cardiac cell-specific markers can be used to confirm the degree of differentiation that the stem cell has undergone. In addition, the activation or deactivation of particular cardiac-specific markers can be used to determine the degree of multipotency of a human cardiogenic progenitor cell. This can be achieved by comparing the cardiac-specific markers present on, or expressed by the cell with the marker profile of cardiac cells during development and inferring the degree of multipotency of the differentiated cell based on the known degree of multipotency of the corresponding cardiac cell during embryonic development.

Marker-specific agents can be used to recognize stem cell markers, for instance labeled antibodies that recognize and bind to cell-surface markers or antigens on desired stem cells. Antibodies or similar agents specific for a given marker, or set of markers, can be used to separate and isolate the desired stem cells using fluorescent activated cell sorting (FACS), panning methods, magnetic particle selection, particle sorter selection and other methods known to persons skilled in the art, including density separation (Xu et al. (2002) Circ. Res. 91:501; U.S.S.N. 20030022367) and separation based on other physical properties (Doevendans et al. (2000) J. Mol. Cell. Cardiol. 32:839-851).

Alternatively, genetic selection methods can be used, where a progenitor or stem cell can be genetically engineered to express a reporter protein operatively linked to a tissue-specific promoter and/or a specific gene promoter; therefore the expression of the reporter can be used for positive selection methods to identify and/or isolate or enrich the desired stem cell. For example, a fluorescent reporter protein can be expressed in the desired stem cell by genetic engineering methods to operatively link the marker protein to a promoter active in a desired stem cell (Klug et al. (1996) J. Clin. Invest. 98:216-224; U.S. Pat. No. 6,737, 054). In some embodiments, cells from which the human cardiogenic cells and/or endocardial endothelial cells are derived are not modified using genetic means. Other approaches for positive selection include drug selection, for instance as described by Klug et al., supra, involving enrichment of desired cells by density gradient centrifugation. Negative selection can be performed, including selecting and removing cells with undesired markers or characteristics, for example fibroblast markers, epithelial cell markers etc.

Undifferentiated ES cells express genes that can be used as markers to detect the presence of undifferentiated cells. The polypeptide products of such genes can be used as markers for negative selection. For example, see U.S.S.N. 2003/0224411 A1; Bhattacharya (2004) Blood 103(8):2956-64; and Thomson (1998), supra., each herein incorporated by reference. Human ES cell lines express cell surface markers that characterize undifferentiated nonhuman primate ES and human EC cells, including, but not limited to, stage-specific embryonic antigen (SSEA)-3, SSEA-4, TRA-I-60, TRA-1-81, and alkaline phosphatase. The globo-series glycolipid GL7, which carries the SSEA-4 epitope, is formed by the addition of sialic acid to the globo-series glycolipid Gb5, which carries the SSEA-3 epitope. Thus, GL7 reacts with antibodies to both SSEA-3 and SSEA-4. Undifferentiated human ES cell lines do not stain for SSEA-1, but differentiated cells stain strongly for SSEA-1. Methods for proliferating hES cells in the undifferentiated form are described in WO 99/20741, WO 01/51616, and WO 03/020920, the contents of which are herein incorporated by reference in their entireties.

Exemplary cell surface markers expressed on cardiogenic mesoderm cells include, but are not limited to, KDR, Nodal, DKK1, MESP1, GSC, EOMES, and $BryT^{low}$ (see e.g., FIG. 1).

Exemplary cell surface markers expressed on cardiac progenitor cells include, but are not limited to, TMEM88, GATA4, ISL1, MYL4, and NKX2-5.

Exemplary cell surface markers expressed on cardiomyocytes include, but are not limited to, NKX2-5, MYH6, MYL7, TBX5, ATP2a2, RYR2, and cTnT.

Exemplary cell surface markers expressed on endocardial endothelial progenitor cells include, but are not limited to, KDR+/CD34+, NFATC1, SCL/TAL1, and $CD31^{low}$. Expression of NFATc1 is a hallmark of endocardial endothelial cells prepared as described herein. Such cells fo not express HAND1 of RUNX1.

Exemplary cell surface markers expressed on definitive endocardial endothelial cells include, but are not limited to, CD31+ and VE-cadherin.

Particular cell compositions with combinations of such cell surface markers are exemplified herein in the Examples section.

In some embodiments, the desired cells (e.g., definitive endocardial endothelial cells) are an enriched population of cells; that is, the percentage of human definitive endocardial endothelial cells (e.g., percent of cells) in a population of cells is at least 10% of the total number of cells in the population. For example, an enriched population comprises at least 15% definitive endocardial endothelial cells, at least 20%, at least 30%, at least 40%, at least 50%, at least 60%, at least 70%, at least 80%, at least 90%, at least 95%, at least 99% or even 100% of the population comprises human definitive endocardial endothelial cells. In some embodiments, a population of cells comprises at least 100 cells, at least 500 cells, at least 1000 cells, at least $1\times10^4$ cells, at least $1\times10^5$ cells, at least $1\times10^6$ cells, at least $1\times10^7$ cells, at least $1\times10^8$ cells, at least $1\times10^9$ cells, at least $1\times10^{10}$ cells, at least $1\times10^{11}$ cells, at least $1\times10^{12}$ cells, at least $1\times10^{13}$ cells, at least $1\times10^{14}$ cells, at least $1\times10^{15}$ cells, or more.

In one embodiment, the human definitive endocardial endothelial cells described herein are not tumor cells or cancer cells. In such embodiments, the human definitive endocardial endothelial cell can be distinguished from a tumor cell or cancer cell using e.g., a cell marker profile.

Scaffold Compositions

In one aspect, the cells described herein can be admixed with or grown in or on a preparation that provides a scaffold to support the cells. Such a scaffold can provide a physical advantage in securing the cells in a given location, e.g., after implantation, as well as a biochemical advantage in providing, for example, extracellular cues for the further maturation or, e.g., maintenance of phenotype until the cells are established.

Biocompatible synthetic, natural, as well as semi-synthetic polymers, can be used for synthesizing polymeric particles that can be used as a scaffold material. In general, for the practice of the methods described herein, it is preferable that a scaffold biodegrades such that the cardiogenic lineage cells (e.g., definitive endocardial endothelial cells) can be isolated from the polymer prior to implantation or such that the scaffold degrades over time in a subject and does not require removal. Thus, in one embodiment, the scaffold provides a temporary structure for growth and/or delivery of human cardiac progenitor cells to a subject in need thereof. In some embodiments, the scaffold permits human cells or cell progenitors to be grown in a shape suitable for transplantation or administration into a subject in need thereof, thereby permitting removal of the scaffold prior to implantation and reducing the risk of rejection or allergic response initiated by the scaffold itself Examples of polymers which can be used include natural and synthetic polymers, although synthetic polymers are preferred for reproducibility and controlled release kinetics. Synthetic polymers that can be used include biodegradable polymers such as poly(lactide) (PLA), poly(glycolic acid) (PGA), poly(lactide-co-glycolide) (PLGA), and other poly-hydroxyacids, poly(caprolactone), polycarbonates, polyamides, polyanhydrides, polyphosphazene, polyamino acids, polyortho esters, polyacetals, polycyanoacrylates and biodegradable polyurethanes; non-biodegradable polymers such as polyacrylates, ethylene-vinyl acetate polymers and other acyl-substituted cellulose acetates and derivatives thereof; polyurethanes, polystyrenes, polyvinyl chloride, polyvinyl fluoride, poly(vinyl imidazole), chlorosulphonated polyolefins, and polyethylene oxide. Examples of biodegradable natural polymers include proteins such as albumin, collagen, fibrin, silk, synthetic polyamino acids and prolamines; polysaccharides such as alginate, heparin; and other naturally occurring biodegradable polymers of sugar units. Alternately, combinations of the aforementioned polymers can be used. In one aspect, a natural polymer that is not generally found in the extracellular matrix can be used.

PLA, PGA and PLA/PGA copolymers are particularly useful for forming biodegradable scaffolds. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well documented in the patent literature. The following U.S. Patents, the teachings of which are hereby incorporated by reference, describe in detail suitable polylactides, their properties and their preparation: U.S. Pat. No. 1,995,970 to Dorough; U.S. Pat. No. 2,703,316 to Schneider; U.S. Pat. No. 2,758,987 to Salzberg; U.S. Pat. No. 2,951,828 to Zeile; U.S. Pat. No. 2,676,945 to Higgins; and U.S. Pat. Nos. 2,683,136; 3,531,561 to Trehu.

PGA is a homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. PGA polymers and their properties are described in more detail in Cyanamid Research Develops World's First Synthetic Absorbable Suture", Chemistry and Industry, 905 (1970).

Fibers can be formed by melt-spinning, extrusion, casting, or other techniques well known in the polymer processing area. Preferred solvents, if used to remove a scaffold prior to implantation, are those which are completely removed by the processing or which are biocompatible in the amounts remaining after processing.

Polymers for use in the matrix should meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy.

Scaffolds can be of any desired shape and can comprise a wide range of geometries that are useful for the methods described herein. A non-limiting list of shapes includes, for example, hollow particles, tubes, sheets, cylinders, spheres, and fibers, among others. The shape or size of the scaffold should not substantially impede cell growth, cell differentiation, cell proliferation or any other cellular process, nor should the scaffold induce cell death via e.g., apoptosis or necrosis. In addition, care should be taken to ensure that the scaffold shape permits appropriate surface area for delivery of nutrients from the surrounding medium to cells in the population, such that cell viability is not impaired. The scaffold porosity can also be varied as desired by one of skill in the art.

In some embodiments, attachment of the cells to a polymer is enhanced by coating the polymers with compounds such as basement membrane components, agar, agarose, gelatin, gum arabic, collagens types I, II, III, IV, and V, fibronectin, laminin, glycosaminoglycans, polyvinyl alcohol, mixtures thereof, and other hydrophilic and peptide attachment materials known to those skilled in the art of cell culture or tissue engineering. Examples of a material for coating a polymeric scaffold include polyvinyl alcohol and collagen.

In some embodiments it can be desirable to add bioactive molecules to the scaffold. A variety of bioactive molecules can be delivered using the matrices described herein. These are referred to generically herein as "factors" or "bioactive factors".

In one embodiment, the bioactive factors include growth factors. Examples of growth factors include platelet derived growth factor (PDGF), transforming growth factor alpha or beta (TGFβ), bone morphogenic protein 4 (BMP4), fibroblastic growth factor 7 (FGF7), fibroblast growth factor 10 (FGF10), epidermal growth factor (EGF/TGFα), vascular endothelium growth factor (VEGF), some of which are also angiogenic factors.

These factors are known to those skilled in the art and are available commercially or described in the literature. Bioactive molecules can be incorporated into the matrix and released over time by diffusion and/or degradation of the matrix, or they can be suspended with the cell suspension.

Treatment of Cardiac Disease and/or Injury

The heart is made of three major tissue layers: the endocardium, myocardium, and epicardium. The coronary arteries that are responsible for blood flow in the heart are formed within the myocardial layer. The epicardium is the outermost epithelial layer of the heart and is responsible for the formation of coronary vascular smooth muscle cells. Studies have shown that epicardial cells generate coronary vascular smooth muscle cells and interstitial fibroblasts. The endocardium is the internal epithelial layer of the heart, which lines the inner wall of the heart chambers. The endocardium provides the endothelial cells for much of the coronary circulation. Provided herein are methods of generating endocardial endothelial cells of the endocardium and uses thereof in the treatment of cardiac injury, cardiac disease/disorder, wound healing and/or promoting angiogenesis.

The methods and compositions provided herein relate to the generation and use of human cardiac lineage cells and/or endocardial endothelial cells. In one embodiment, a therapeutically effective amount of endocardial endothelial cells is administered to a subject to (i) promote angiogenesis, particularly coronary angiogenesis, (ii) tissue repair and/or tissue engineering (e.g., cardiac repair), (iii) to generate heart valves, and/or (iv) to repair heart valve function. In another embodiment, a therapeutically effective amount of definitive cardiomyocytes is administered to a subject to (i) repair infarcted zones of cardiac injury, (ii) promote recovery following cardiac ischemia or injury, and/or (iii) tissue repair and/or tissue engineering. In another embodiment, a therapeutically effective amount of cardiogenic progenitor cells are administered to a subject to repair cardiac injury, for tissue engineering, and to treat/prevent a number of cardiac diseases.

Accordingly, provided herein are methods for the treatment and prevention of a cardiac injury or a cardiac disease or disorder in a subject in need thereof. The methods described herein can be used to treat, ameliorate, prevent or slow the progression of a number of cardiac diseases or their symptoms, such as those resulting in pathological damage to the structure and/or function of the heart. The terms "cardiac disease," "cardiac disorder," and "cardiac injury," are used interchangeably herein and refer to a condition and/or disorder relating to the heart, including the valves, endothelium, infarcted zones, or other components or structures of the heart.

Such cardiac diseases or cardiac-related disease include, but are not limited to, myocardial infarction, heart failure, cardiomyopathy, congenital heart defect, heart valve disease/dysfunction, endocarditis, rheumatic fever, mitral valve prolapse, infective endocarditis, hypertrophic cardiomyopathy, dilated cardiomyopathy, myocarditis, cardiomegaly, and mitral insufficiency, among others.

One of skill in the art of medicine will appreciate that vascular diseases, which may be associated with cardiac diseases/disorders can be treated by administering definitive vascular endothelial cells and/or endocardial endothelial cells derived as described herein. Such vascular diseases include, but are not limited to, coronary artery disease, cerebrovascular disease, aortic stenosis, aortic aneurysm, peripheral artery disease, atherosclerosis, varicose veins, angiopathy, infarcted area of heart lacking coronary perfusion, non-healing wounds, diabetic or non-diabetic ulcers, or any other disease/disorder in which it is desirable to induce formation of blood vessels.

As used herein, the terms "administering," "introducing" and "transplanting" are used interchangeably in the context of the placement of cells, e.g. cardiac progenitor cells or definitive cells, as described herein into a subject, by a method or route which results in at least partial localization of the introduced cells at a desired site, such as a site of injury or repair, such that a desired effect(s) is produced. The cells e.g. cardiogenic progenitor cells, or their differentiated progeny (e.g. cardiomyocytes, endocardial endothelial cells etc.) can be implanted directly to the heart, or alternatively be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years, i.e., long-term engraftment. In other embodiments, cardiac progenitor cells or their differentiated progeny can be administered via an indirect systemic route of administration, such as an intraperitoneal or intravenous route.

When provided prophylactically, the cardiac progenitor cells or their differentiated progeny described herein can be administered to a subject in advance of any symptom of a cardiac disorder, e.g., an acute myocardial infarction, or infective endocarditis before onset of valve dysfunction. Accordingly, the prophylactic administration of a population of cardiac progenitor cells or their differentiated progeny serves to prevent a cardiac disorder, as disclosed herein.

When provided therapeutically, cardiac progenitor cells or their differentiated progeny are provided at (or after) the onset of a symptom or indication of a cardiac disorder, e.g., myocardial infarction, endocarditis, infective endocarditis, etc.

In some embodiments of the aspects described herein, the population of cells being administered according to the methods described herein comprises allogeneic cardiac progenitor cells or their differentiated progeny obtained from one or more donors. As used herein, "allogeneic" refers to a cardiac progenitor cell or biological samples comprising cardiac progenitor cells or their differentiated progeny obtained from one or more different donors of the same species, where the genes at one or more loci are not identical. For example, a cardiac progenitor cell population being administered to a subject can be derived from pluripotent stem cells obtained from one more unrelated donor subjects, or from one or more non-identical siblings. In some embodiments, syngeneic cardiac progenitor cell populations can be used, such as those obtained from genetically identical animals, or from identical twins. In other embodiments of this aspect, the cardiac progenitor cells or their differentiated progeny are autologous cells; that is, the cells are obtained or isolated from a subject and administered to the same subject, i.e., the donor and recipient are the same.

Depending on the disease/disorder or injury to be treated, as well as the location of cardiac injury, either undifferentiated cardiac progenitor cells or their differentiated progeny can be administered to the subject.

Pharmaceutically Acceptable Carriers

The methods of administering human cardiac progenitor cells or their differentiated progeny to a subject as described herein involve the use of therapeutic compositions comprising such cells. Therapeutic compositions contain a physiologically tolerable carrier together with the cell composition and optionally at least one additional bioactive agent as described herein, dissolved or dispersed therein as an active ingredient. In a preferred embodiment, the therapeutic composition is not substantially immunogenic when administered to a mammal or human patient for therapeutic purposes, unless so desired. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset, transplant rejection, allergic reaction, and the like. A pharmaceutically acceptable carrier will not promote the raising of an immune response to an agent with which it is admixed, unless so desired. The preparation of a composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared.

In general, the cardiac progenitor cells or their differentiated progeny described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the human cardiac progenitor cells as described herein using routine experimentation.

A cell composition can also be emulsified or presented as a liposome composition, provided that the emulsification procedure does not adversely affect cell viability. The cells and any other active ingredient can be mixed with excipients which are pharmaceutically acceptable and compatible with the active ingredient and in amounts suitable for use in the therapeutic methods described herein.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions as described herein that is effective in the treatment of a particular disorder or condition will depend on the nature of the disorder or condition, and can be determined by standard clinical techniques.

It is also contemplated herein that compositions comprising the endocardial endothelial cells as described herein and a scaffold can be used in the treatment of a subject in need thereof. The scaffold can aid in the formation of a 3D tissue for transplant or for screening assays or other research purposes. In another embodiment, the endocardial endothelial cells are present in a 2D sheet, with or without the presence of a scaffold. In one embodiment, the scaffold is biodegradable.

Administration and Efficacy

Provided herein are methods for treating a cardiac disease, a cardiac disorder, or a cardiac injury comprising administering human cardiogenic progenitor cells or differentiated progeny thereof, particularly endocardial endothelial cells, to a subject in need thereof. Also provided herein are methods that exploit the strong angiogenic activity of the endocardial endothelial cells described herein, for treatment outside the cardiac arena. Such uses include, for example, use in promoting wound healing.

Measured or measurable parameters include clinically detectable markers of disease, for example, elevated or depressed levels of a clinical or biological marker, as well as parameters related to a clinically accepted scale of symptoms or markers for a disease or disorder. It will be understood, however, that the total usage of the compositions and formulations as disclosed herein will be decided by the attending physician within the scope of sound medical judgment. The exact amount required will vary depending on factors such as the type of disease being treated.

The term "effective amount" as used herein refers to the amount of a population of human cardiac progenitor cells or their progeny (e.g., endocardial endothelial cells) needed to alleviate at least one or more symptoms of a disease or disorder, including but not limited to a cardiac injury or a cardiac disease or disorder, or, e.g., wound healing or another indication that can benefit from the promotion of angiogenesis. An "effective amount" relates to a sufficient amount of a composition to provide the desired effect, e.g., treat a subject having an infarct zone following myocardial infarction, prevent, repair and/or restore valve dysfunction following infective endocarditis, or a primary valve disease, or promote closure of a wound, etc. The term "therapeutically effective amount" therefore refers to an amount of human cardiac progenitor cells and/or endocardial endothelial cells or a composition comprising human cardiac progenitor cells and/or endocardial endothelial cells that is sufficient to promote a particular effect when administered to a typical subject, such as one who has or is at risk for a cardiac disease or disorder, or one with a wound. An effective amount as used herein would also include an amount sufficient to prevent or delay the development of a symptom of the disease, alter the course of a disease symptom (for example but not limited to, slow the progression of a symptom of the disease), or reverse a symptom of the disease. It is understood that for any given case, an appropriate "effective amount" can be determined by one of ordinary skill in the art using routine experimentation.

In some embodiments, the subject is first diagnosed as having a disease or disorder affecting, e.g., cardiac tissue prior to administering the cells according to the methods described herein. In some embodiments, the subject is first diagnosed as being at risk of developing cardiac disease or disorder prior to administering the cells.

For use in the various aspects described herein, an effective amount of human cardiac progenitor cells or their differentiated progeny, comprises at least $1 \times 10^3$ cardiac progenitor cells or their differentiated progeny, at least $1 \times 10^4$ cardiac progenitor cells or their differentiated progeny, at least $1 \times 10^5$ cardiac progenitor cells or their differentiated progeny, at least $5 \times 10^5$ cardiac progenitor cells or their differentiated progeny, at least $1 \times 10^6$ cardiac progenitor cells or their differentiated progeny, at least $2 \times 10^6$ cardiac progenitor cells or their differentiated progeny, at least $3 \times 10^6$ cardiac progenitor cells or their differentiated progeny, at least $4 \times 10^6$ cardiac progenitor cells or their differentiated progeny, at least $5 \times 10^6$ cardiac progenitor cells or their differentiated progeny, at least $6 \times 10^6$ cardiac progenitor cells or their differentiated progeny, at least $7 \times 10^6$ cardiac progenitor cells or their differentiated progeny, at least $8 \times 10^6$ cardiac progenitor cells or their differentiated progeny, at least $9 \times 10^6$ cardiac progenitor cells or their differentiated progeny, at least $1 \times 10^7$ cardiac progenitor cells or their differentiated progeny, at least $1.1 \times 10^7$ cardiac progenitor cells or their differentiated progeny, at least $1.2 \times 10^7$ cardiac progenitor cells or their differentiated progeny, at least $1.3 \times 10^7$ cardiac progenitor cells or their differentiated progeny, at least $1.4 \times 10^7$ cardiac progenitor cells or their differentiated progeny, at least $1.5 \times 10^7$ cardiac progenitor cells or their differentiated progeny, at least $1.6 \times 10^7$ cardiac progenitor cells or their differentiated progeny, at least $1.7 \times 10^7$ cardiac progenitor cells or their differentiated progeny, at least $1.8 \times 10^7$ cardiac progenitor cells or their differentiated progeny, at least $1.9 \times 10^7$ cardiac progenitor cells or their differentiated progeny, at least $2 \times 10^7$ cardiac progenitor cells or their differentiated progeny, at least $3 \times 10^7$ cardiac progenitor cells or their differentiated progeny, at least $4 \times 10^7$ cardiac progenitor cells or their differentiated progeny, at least $5 \times 10^7$ cardiac progenitor cells or their differentiated progeny, at least $6 \times 10^7$ cardiac progenitor cells or their differentiated progeny, at least $7 \times 10^7$ cardiac progenitor cells or their differentiated progeny, at least $8 \times 10^7$ cardiac progenitor cells or their differentiated progeny, at least $9 \times 10^7$ cardiac progenitor cells or their differentiated progeny, at least $1 \times 10^8$ cardiac progenitor cells or their differentiated progeny, at least $2 \times 10^8$ cardiac progenitor cells or their differentiated progeny, at least $5 \times 10^8$ cardiac progenitor cells or their differentiated progeny, at least $7 \times 10^8$ cardiac progenitor cells or their differentiated progeny, at least $1 \times 10^9$ cardiac progenitor cells or their differentiated progeny, at least $2 \times 10^9$ cardiac progenitor cells or their differentiated progeny, at least $3 \times 10^9$ cardiac progenitor cells or their differentiated progeny, at least $4 \times 10^9$ cardiac progenitor cells or their differentiated progeny, at least $5 \times 10^9$ or more cardiac progenitor cells or their differentiated progeny. Amounts of endocardial endothelial cells administered for, e.g., wound healing can be similar to those administered for cardiac indications, although the extent of the wound should be considered and larger or deeper wounds may require more cells than for cardiac treatment.

One of skill in the art will recognize that the number of definitive cardiomyocytes to be administered to treat e.g., myocardial infarction or cardiomyopathies will necessarily be higher than the number of cardiac progenitor cells, as cardiomyocytes exhibit less proliferation in vivo.

The cardiac progenitor cells or their differentiated progeny can be derived from one or more donors, or can be obtained from an autologous source. In some embodiments of the aspects described herein, the cardiac progenitor cells or their differentiated progeny are expanded in culture prior to administration to a subject in need thereof.

Exemplary modes of administration for use in the methods described herein include, but are not limited to, injection, systemic administration and implantation (with or without a scaffold material). "Injection" includes, without limitation, intravenous, intramuscular, intraarterial, intradermal, intraperitoneal and subcutaneous.

In some embodiments, a therapeutically effective amount of cardiac progenitor cells or their differentiated progeny (e.g., endocardial endothelial cells) is administered using direct injection into the heart (e.g., intracardiac injection), including administration during open-heart surgery or by intracardiac injection through an intact chest. In some aspects of these methods, a therapeutically effective amount of cardiac progenitor cells or their differentiated progeny (e.g., endocardial endothelial cells) are administered using a systemic, such as an intraperitoneal or intravenous route. In other aspects of these methods, a therapeutically effective amount of cardiac progenitor cells or their differentiated progeny (e.g., endocardial endothelial cells) is administered using systemic or intraperitoneal administration. These methods are particularly aimed at therapeutic and prophylactic treatments of human subjects having, or at risk of having, a cardiac disease or disorder. The human cardiac progenitor cells or their differentiated progeny (e.g., endocardial endothelial cells) described herein can be administered to a subject having any cardiac disease or disorder by any appropriate route which results in an effective treatment in the subject. In some embodiments of the aspects described herein, a subject having a cardiac disorder is first selected prior to administration of the cells.

In some embodiments, an effective amount of cardiac progenitor cells or their differentiated progeny (e.g., endocardial endothelial cells) are administered to a subject by intracardiac administration or delivery. As defined herein, "intracardiac" administration or delivery refers to all routes of administration whereby a population of cardiac progenitor cells or their differentiated progeny (e.g., endocardial endothelial cells) is administered in a way that results in direct contact of these cells with the cardiac endothelium or myocardium of a subject, including, but not limited to, systemic administration, direct cardiac injection, during surgery (e.g., cardiac bypass surgery, during implantation of a cardiac mini-pump or a pacemaker, etc.), or intravenous administration (e.g., bolus and/or infusions). In some such embodiments, the cells are injected into the myocardium (e.g., cardiomyocytes), one or more valves (e.g., endocardial endothelial cells), the endothelium (e.g., endocardial endothelial cells), or into the cavity of the atria and/or ventricles. In embodiments, intracardiac delivery of cells includes administration methods whereby cells are administered, for example as a cell suspension, to a subject undergoing surgery via a single injection or multiple "mini" injections into the desired region of the heart.

For administration in a wound healing context, the cells can be applied directly to the wound either in saline or in a compatible gel or matrix, alone or with other factors to promote healing, before or after closure of the wound with sutures or clips and bandaging if necessary or desired.

In some embodiments, an effective amount of cardiac progenitor cells or their differentiated progeny (e.g., endocardial endothelial cells) is administered to a subject by systemic administration, such as intravenous administration.

The phrases "systemic administration," "administered systemically", "peripheral administration" and "administered peripherally" are used herein refer to the administration of a population of cardiac progenitor cells or their differentiated progeny other than directly into a target site, tissue, or organ, such as the heart, such that it enters, instead, the subject's circulatory system.

In some embodiments of the aspects described herein, one or more routes of administration are used in a subject to achieve distinct effects.

The choice of formulation will depend upon the specific composition used and the number of cardiac progenitor cells or their differentiated progeny to be administered; such formulations can be adjusted by the skilled practitioner. However, as an example, where the composition is cardiac progenitor cells or their differentiated progeny in a pharmaceutically acceptable carrier, the composition can be a suspension of the cells in an appropriate buffer (e.g., saline buffer) at an effective concentration of cells per mL of solution. The formulation can also include cell nutrients, a simple sugar (e.g., for osmotic pressure regulation) or other components to maintain the viability of the cells. Alternatively, the formulation can comprise a scaffold, such as a biodegradable scaffold.

In some embodiments, additional agents to aid in treatment of the subject can be administered before or following treatment with the cardiac progenitor cells or their differentiated progeny as described herein. Such additional agents can be used to prepare the target tissue for administration of the progenitor cells. Alternatively the additional agents can be administered after the cardiac progenitor cells or their differentiated progeny to support the engraftment and growth of the administered cell into the heart or other desired administration site. In some embodiments, the additional agent comprises growth factors, such as VEGF, FGF family members, IGF family members, Notch signaling compounds or PDGF.

The efficacy of treatment can be determined by the skilled clinician. However, a treatment is considered "effective treatment," as the term is used herein, if any one or all of the symptoms, or other clinically accepted symptoms or markers of disease, e.g., cardiac disease, cardiac injury and/or a cardiac disorder are reduced, e.g., by at least 10% following treatment with a composition comprising human cardiac progenitor cells or their differentiated progeny as described herein. Methods of measuring these indicators are known to those of skill in the art and/or described herein.

Indicators of cardiac disease or cardiac disorder, or cardiac injury include functional indicators or parameters, e.g., stroke volume, heart rate, left ventricular ejection fraction, heart rate, heart rhythm, blood pressure, heart volume, regurgitation, etc. as well as biochemical indicators, such as a decrease in markers of cardiac injury, such as serum lactate dehydrogenase, or serum troponin, among others. As one example, myocardial ischemia and reperfusion are associated with reduced cardiac function. Subjects that have suffered an ischemic cardiac event and/or that have received reperfusion therapy have reduced cardiac function when compared to that before ischemia and/or reperfusion. Measures of cardiac function include, for example, ejection fraction and fractional shortening. Ejection fraction is the fraction of blood pumped out of a ventricle with each heartbeat. The term ejection fraction applies to both the right and left ventricles. LVEF refers to the left ventricular ejection fraction (LVEF). Fractional shortening refers to the difference between end-diastolic and end-systolic dimensions divided by end-diastolic dimension.

Non-limiting examples of clinical tests that can be used to assess cardiac functional parameters include echocardiography (with or without Doppler flow imaging), electrocardiogram (EKG), exercise stress test, Holter monitoring, or measurement of β-natriuretic peptide.

Where necessary or desired, animal models of cardiac injury or cardiac disease can be used to gauge the effectiveness of a particular composition as described herein. For example, an isolated working rabbit or rat heart model, or a coronary ligation model in either canines, non-human primates or porcines can be used. Animal models of cardiac function are useful for monitoring infarct zones, coronary perfusion, electrical conduction, left ventricular end diastolic pressure, left ventricular ejection fraction, heart rate, blood pressure, degree of hypertrophy, diastolic relaxation function, cardiac output, heart rate variability, and ventricular wall thickness, etc.

The efficacy of wound treatment using cells as described herein can be monitored in, e.g., an animal model that uses, for example, a skin punch that creates a uniformly sized wound. One or more control wounds that do not receive the cell treatment can be examined on the same animal that receives cell treatments for one or more other wounds. Regular monitoring of the wound and its rate of closure, etc. can provide a quantitative measure of wound healing efficacy. In one embodiment, a wound healing method is "therapeutically effective" if one or more measures of wound healing improves by at least 10% relative to a control wound not receiving the cell treatments as described herein, and preferably by at least 20%, at least 30%, at least 40%, at least 50%, at least 60%, at least 70%, at least 80%, at least 90%, at least 1-fold, at least 2-fold or more.

Screening Assays

The compositions described herein are useful to screen for agents for inducing differentiation of human cardiac progenitor cells or their differentiated progeny (e.g., endocardial endothelial cells) or for the treatment of a cardiac disease or disorder.

In some embodiments, the isolated human cardiac progenitor cells or their differentiated progeny (e.g., endocardial endothelial cells) or isolated human disease-specific cardiac cells derived from such human cardiac progenitor cells can be used in methods, assays, systems and kits to develop specific in vitro assays. Such assays for drug screening and toxicology studies have an advantage over existing assays because they are of human origin, and do not require immortalization of cell lines, have high efficiency of differentiation to desired definitive cardiac cell types nor do they require tissue from cadavers, which poorly reflect the physiology of normal human cells. For example, the methods, assays, systems, and kits described herein can be used to identify and/or test agents that can promote differentiation along the cardiac lineage. In addition, or in the alternative, the methods, assays, systems, and kits can be used to identify and/or test for agents useful in treating a cardiac disease or disorder, or for preventing/treating a cardiac injury.

In other embodiments, the endocardial endothelial cells can be used to test a candidate agent(s) for effects on cell proliferation, growth arrest, in vitro angiogenesis, in vitro vasculogenesis, epithelial to mesenchymal transition, endothelial activation, vasodilatory and vasoconstrictor signaling, thrombosis, leukocyte adhesion and cancer cell adhesion. In other embodiments, the cells as described herein can be used in 3D co-culture systems, for example to promote vascularization or paracrine support, for use in tissue engineering methods.

Accordingly, provided herein are methods for screening a test compound for biological activity, the method comprising (a) contacting an isolated human cardiac progenitor cell as described herein, or its progeny, with a test compound and (b) determining any effect of the compound on the cell. In one embodiment, the screening method further comprises generating a human cardiac progenitor cell or a human cardiac disease-specific cell as disclosed herein. In one embodiment, the cardiac progenitor cell is first differentiated to a desired cardiac cell phenotype. The effect on the cell can be one that is observable directly, or indirectly by use of reporter molecules.

As used herein, the term "biological activity" or "bioactivity" refers to the ability of a test compound to affect a biological sample. Biological activity can include, without limitation, elicitation of a stimulatory, inhibitory, regulatory, toxic or lethal response in a biological assay. For example, a biological activity can refer to the ability of a compound to modulate the effect of an enzyme, block a receptor, stimulate a receptor, modulate the expression level of one or more genes, modulate cell proliferation, modulate cell division, modulate cell metabolism, modulate differentiation, modulate cell morphology, or a combination thereof. In some instances, a biological activity can refer to the ability of a test compound to produce a toxic effect in a biological sample.

As discussed above, the specific lineage can be a lineage that is phenotypic and/or genotypic of a disease (e.g., a cardiac disease). Alternatively, the specific lineage can be a lineage which is phenotypic and/or genotypic of an organ and/or tissue or a part thereof (e.g., heart).

As used herein, the term "test compound" or "candidate agent" refers to an agent or collection of agents (e.g., compounds) that are to be screened for their ability to have an effect on the cell. Test compounds can include a wide variety of different compounds, including chemical compounds, mixtures of chemical compounds, e.g., polysaccharides, small organic or inorganic molecules (e.g. molecules having a molecular weight less than 2000 Daltons, less than 1000 Daltons, less than 1500 Dalton, less than 1000 Daltons, or less than 500 Daltons), biological macromolecules, e.g., peptides, proteins, peptide analogs, and analogs and derivatives thereof, peptidomimetics, nucleic acids, nucleic acid analogs and derivatives, an extract made from biological materials such as bacteria, plants, fungi, or animal cells or tissues, naturally occurring or synthetic compositions.

Depending upon the particular embodiment being practiced, the test compounds can be provided free in solution, or can be attached to a carrier, or a solid support, e.g., beads. A number of suitable solid supports can be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds can be screened individually, or in groups. Group screening is particularly useful where hit rates for effective test compounds are expected to be low such that one would not expect more than one positive result for a given group.

A number of small molecule libraries are known in the art and are commercially available. These small molecule libraries can be screened using the screening methods described herein. A chemical library or compound library is a collection of stored chemicals that can be used in conjunction with the methods described herein to screen candidate agents for a particular effect. A chemical library also comprises information regarding the chemical structure, purity, quantity, and physiochemical characteristics of each compound. Compound libraries can be obtained commercially, for example, from Enzo Life Sciences™, Aurora Fine Chemicals™, Exclusive Chemistry Ltd.™, ChemDiv, ChemBridge™, TimTec Inc.™, AsisChem™, and Princeton Biomolecular Research™, among others.

Without limitation, the compounds can be tested at any concentration that can exert an effect on the cells relative to a control over an appropriate time period. In some embodiments, compounds are tested at concentrations in the range of about 0.01 nM to about 100 mM, about 0.1 nM to about 500 µM, about 0.1 µM to about 20 µM, about 0.1 µM to about 10 µM, or about 0.1 µM to about 5 µM.

The compound screening assay can be used in a high through-put screen. High through-put screening is a process in which libraries of compounds are tested for a given activity. High through-put screening seeks to screen large numbers of compounds rapidly and in parallel. For example, using microtiter plates and automated assay equipment, a laboratory can perform as many as 100,000 assays per day in parallel.

The compound screening assays described herein can involve more than one measurement of the cell or reporter function (e.g., measurement of more than one parameter and/or measurement of one or more parameters at multiple points over the course of the assay). Multiple measurements can allow for following the biological activity over incubation time with the test compound. In one embodiment, the reporter function is measured at a plurality of times to allow monitoring of the effects of the test compound at different incubation times.

The screening assay can be followed by a subsequent assay to further identify whether the identified test compound has properties desirable for the intended use. For example, the screening assay can be followed by a second assay selected from the group consisting of measurement of any of: bioavailability, toxicity, or pharmacokinetics, but is not limited to these methods.

Kits

Another aspect of the technology described herein relates to kits for treating a cardiac disease or disorder, kits for screening a candidate agent and/or kits for differentiating a human stem cell to a human cardiac progenitor cell or for differentiating a human cardiac progenitor cell to a specific type or types of human cardiac cell(s). Described herein are kit components that can be included in one or more of the kits described herein.

In one embodiment, the kits described herein can include a human cardiac progenitor cell and/or an endocardial endothelial cell, as that term is used herein. In one embodiment, one or more signaling pathway agonists or antagonists that promote differentiation of a stem cell are included in the kit. In another embodiment, a component described herein such as one or more TGF-β receptor agonists (e.g., Activin A), one or more BMP agonists (e.g., BMP4), one or more FGF agonists (e.g., bFGF), and instructions for converting a stem cell (e.g., embryonic stem cell, isolated pluripotent stem cell, adult stem cell etc.) to a human cardiac progenitor cell, e.g., using a method described herein.

Another aspect of the technology disclosed herein relates to kits to produce human cardiac progenitor cells and/or endocardial endothelial cells according to the methods as disclosed herein. Another aspect provided herein relates to kits comprising a human mesodermal stem cell comprising a heterologous sequence encoding a reporter polypeptide, operably linked to sequences that regulate the NFAT1c gene (e.g., an endogenous NFAT1c gene).

In some embodiments, the components described herein can be provided singularly or in any combination as a kit. The kit includes the components described herein, e.g., a composition(s) that includes a compound(s) described herein, e.g., a compound or cocktail of compounds or reagents for differentiating a human stem cell to a cardiac progenitor cell or its differentiated progeny. Such kits can optionally include one or more agents that permit the detection of a cardiac progenitor cell marker or a cardiac cell marker or set thereof. In addition, the kit optionally comprises informational material.

In some embodiments, the compound in the kit can be provided in a watertight or gas tight container which in some embodiments is substantially free of other components of the kit. For example, a signaling pathway or differentiation pathway modulating compound can be supplied in more than one container, e.g., it can be supplied in a container having sufficient reagent for a predetermined number of differentiation reactions, e.g., 1, 2, 3 or greater. One or more compound as described herein can be provided in any form, e.g., liquid, dried or lyophilized form. It is preferred that the compound(s) described herein are substantially pure and/or sterile. When the one or more signaling pathway modulating compounds described herein is provided in a liquid solution, the liquid solution preferably is an aqueous solution, with a sterile aqueous solution being preferred. When a compound described herein is provided as a dried form, reconstitution generally is by the addition of a suitable solvent. The solvent, e.g., sterile water or buffer, can optionally be provided in the kit.

The informational material can be descriptive, instructional, marketing or other material that relates to the methods described herein and/or the use of a compound(s) described herein for the methods described herein. The informational material of the kits is not limited in its form. In one embodiment, the informational material can include information about production of the compound, molecular weight of the compound, concentration, date of expiration, batch or production site information, and so forth. In one embodiment, the informational material relates to methods for using or administering the compound.

In one embodiment, the informational material can include instructions to administer a human cardiac progenitor cell or differentiated progeny thereof as described herein in a suitable manner to effect treatment of a cardiac injury or a cardiac disease or disorder, e.g., in a suitable dose, dosage form, or mode of administration (e.g., a dose, dosage form, or mode of administration described herein). In another embodiment, the informational material can include instructions for differentiating a human stem cell to a human cardiac progenitor cell or differentiated progeny thereof. Alternatively, the informational material can include instructions for screening a candidate agent for treating a cardiac disease or disorder.

In addition to a compound(s) described herein, the composition of the kit can include other ingredients, such as a solvent or buffer, a stabilizer, a preservative, and/or an additional agent, e.g., for differentiating stem cells (e.g., in vitro) or for treating a condition or disorder described herein. Alternatively, the other ingredients can be included in the kit, but in different compositions or containers than a cell or signaling pathway or differentiation pathway modulating compound described herein. In such embodiments, the kit can include instructions for admixing a compound(s) described herein and the other ingredients, or for using a compound(s) described herein together with the other ingredients, e.g., instructions on combining the two agents prior to use or administration.

The kit can include a component for the detection of a marker for human cardiac progenitor cells, ES cells iPS cells, cardiomyocytes, endocardial endothelial cells, hematopoietic cells, vascular endothelial cells etc. In addition, the kit can include one or more antibodies that bind a cell marker, or primers for an RT-PCR or PCR reaction, e.g., a semi-quantitative or quantitative RT-PCR or PCR reaction. Such components can be used to assess the activation of cardiac cell-specific markers or the loss of ES cell, iPSC, or adult stem cell markers. If the detection reagent is an antibody, it can be supplied in dry preparation, e.g., lyophilized, or in a solution. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

The kit can also include one or more reagents for enhancing the efficiency of induced pluripotent stem cell production, such as an HDAC inhibitor (e.g., valproic acid) or a DNA methyltransferase inhibitor (e.g., 5azaC).

In one embodiment, the kit comprises a cell or tissue medium for cardiac mesoderm generation. In one embodiment, the medium comprises Activin A and BMP4.

The kit will typically be provided with its various elements included in one package, e.g., a fiber-based, e.g., a cardboard, or polymeric, e.g., a Styrofoam box. The enclosure can be configured so as to maintain a temperature differential between the interior and the exterior, e.g., it can provide insulating properties to keep the reagents at a preselected temperature for a preselected time.

EXAMPLES

Figure 2:
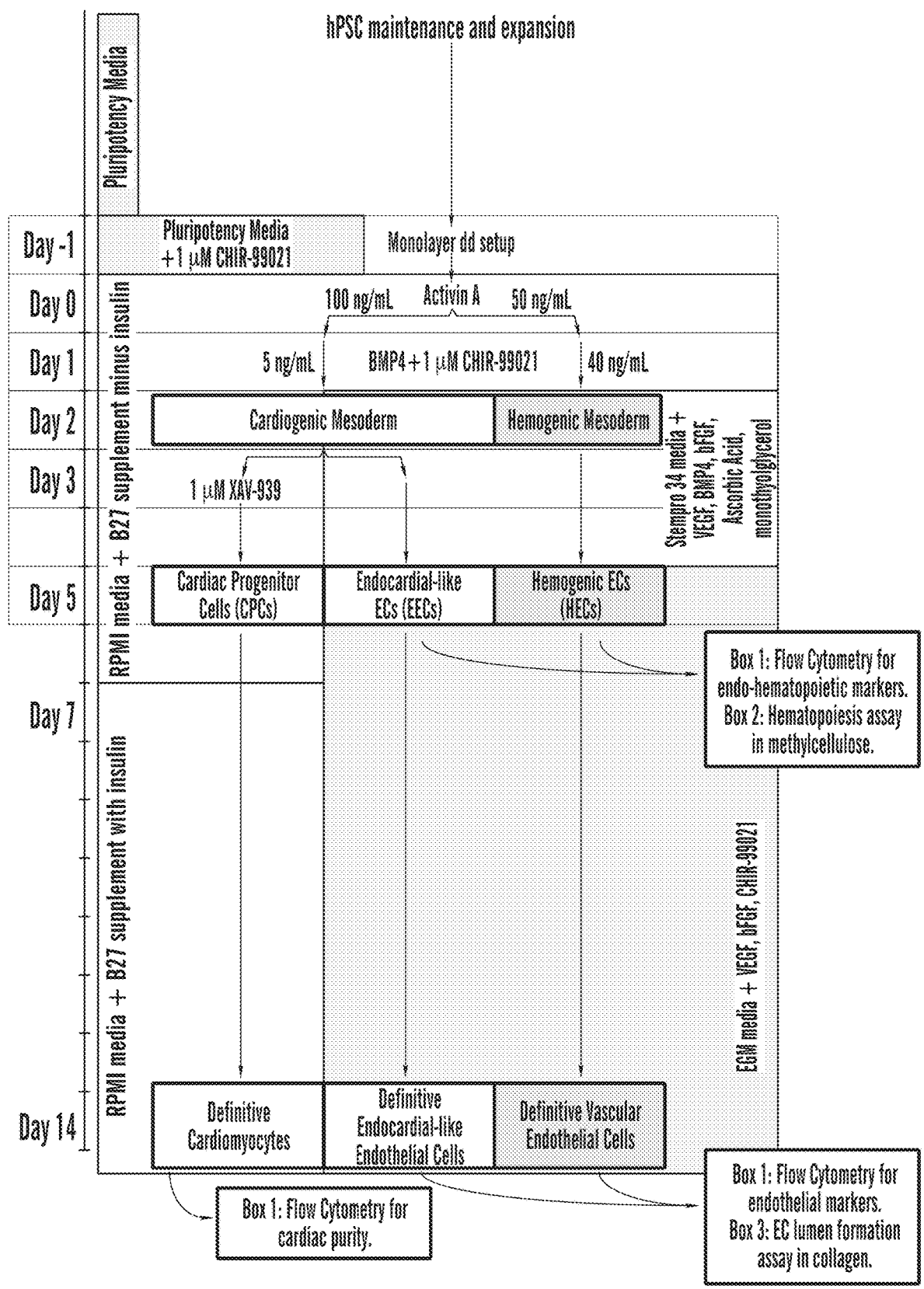
FIG. 2 Outline of protocol for derivation of cardiac and vascular lineages from hPSCs. Overall approach is outlined with lineage fate choices demarcated by arrows mediated by stage specific changes in cytokine and media conditions.

As described below, cues during embryonic development are used in combination with a monolayer differentiation approach as a platform for reproducibly generating different cardiovascular subtypes while achieving greater than 90% purity of all lineages without sorting (FIG. 2). The efficient control of differentiation of diverse cardiovascular subtypes from hPSCs provides a step forward from existing approaches and opens up significant opportunities to dissect the genomics, epigenetics, functional biology, drug screening, and therapeutic applications.

Example 1 hPSC Maintenance, Passaging, and Setup (Steps 1-12)

Figure 8A:
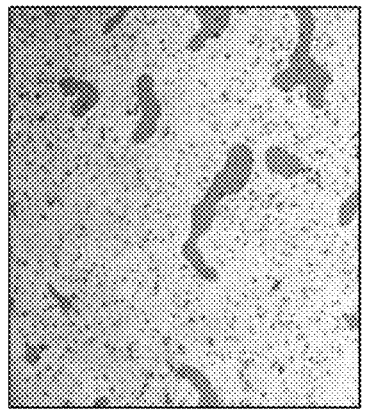
FIGS. 8A-8C. Cell culture density and phenotype from pluripotency to mesoderm.
Figure 8A:
Figure 8A:
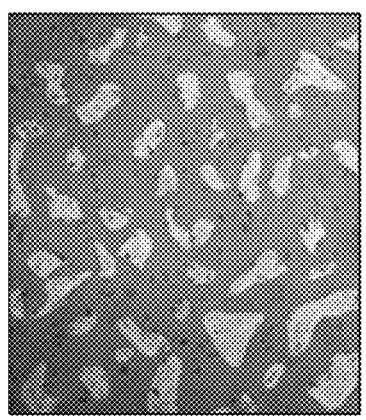

This protocol is used to derive distinct cardiovascular populations from both hESC (RUES2) and hiPSC lines (WTC and IMR90 cells). Successful results have been obtained when the pluripotent stem cells are maintained in either conditioned media or defined mTeSR media. This protocol provides detailed steps for thawing hPSCs, standard maintenance and passaging. During setup of differentiation, cells are dispersed to single cells using the chelating agent VERSE NE™ (ThermoFisher Scientific, Waltham, MA) and plated in pluripotency media containing the Wnt/β-catenin agonist CHIR-99021 for 24 hrs prior to induction with Activin A. Plating density of hPSCs at the onset of differentiation is a well-known variable that influences differentiation efficiency. Three different plating densities were tested to determine the impact on lineage specification into cardiac and endothelial cell types (FIG. 8A) as shown throughout this protocol.

Polarization of Lineages into Cardiogenic vs. Hemogenic Mesoderm (Steps 13A-13B)

Although efforts have been made to define conditions for polarization of lateral plate mesoderm from embryonic stem cells in vitro[3–5,21,22], there has been limited success in translating these observations into protocols to generate high purity definitive populations. Studies have shown that polarization of hPSCs during specification of mesoderm provides developmental cues that are deterministic for generating definitive cell types[7,21]. This is in keeping with a history of studies showing that developmental specification of definitive lineages occurs as early as gastrulation where gene programs required to direct one lineage also simultaneously actively repress gene programs for other lineages[21–24].

Figure 8C:
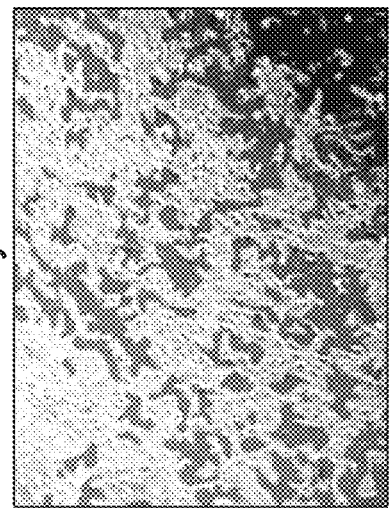
Figure 8B:
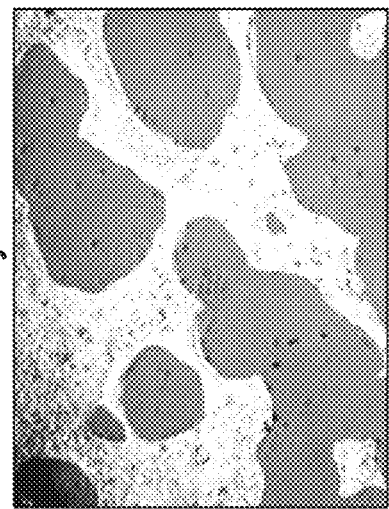
Figure 9A:
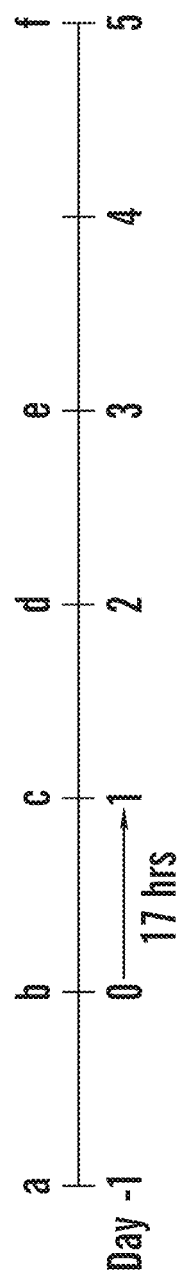
FIGS. 9A-9H Protocol development for directed differentiation of hemogenic endothelium from human embryonic stem cells.
Figure 9B:
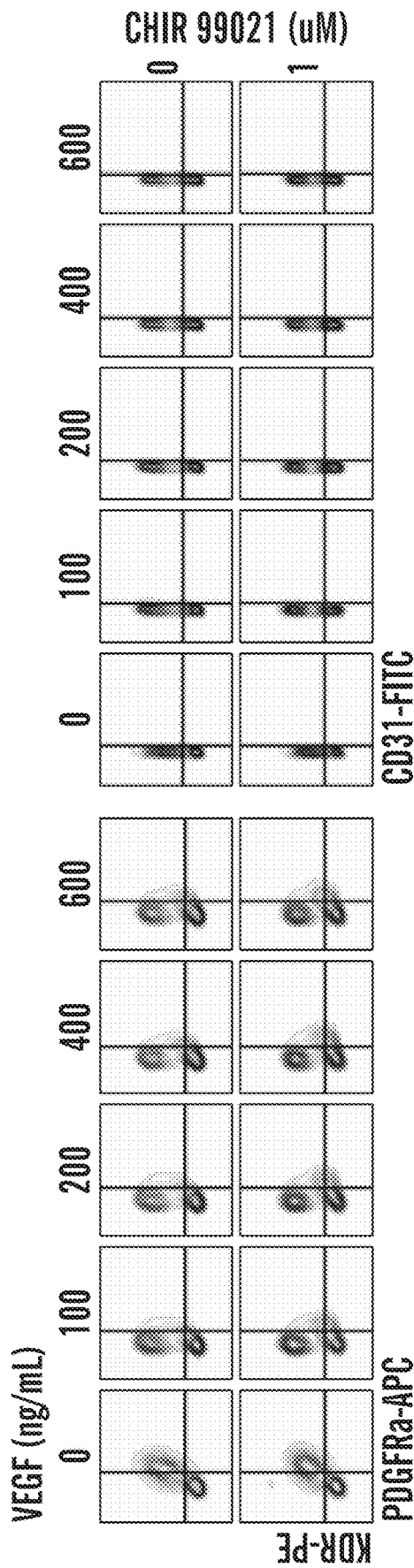
Figure 9C:
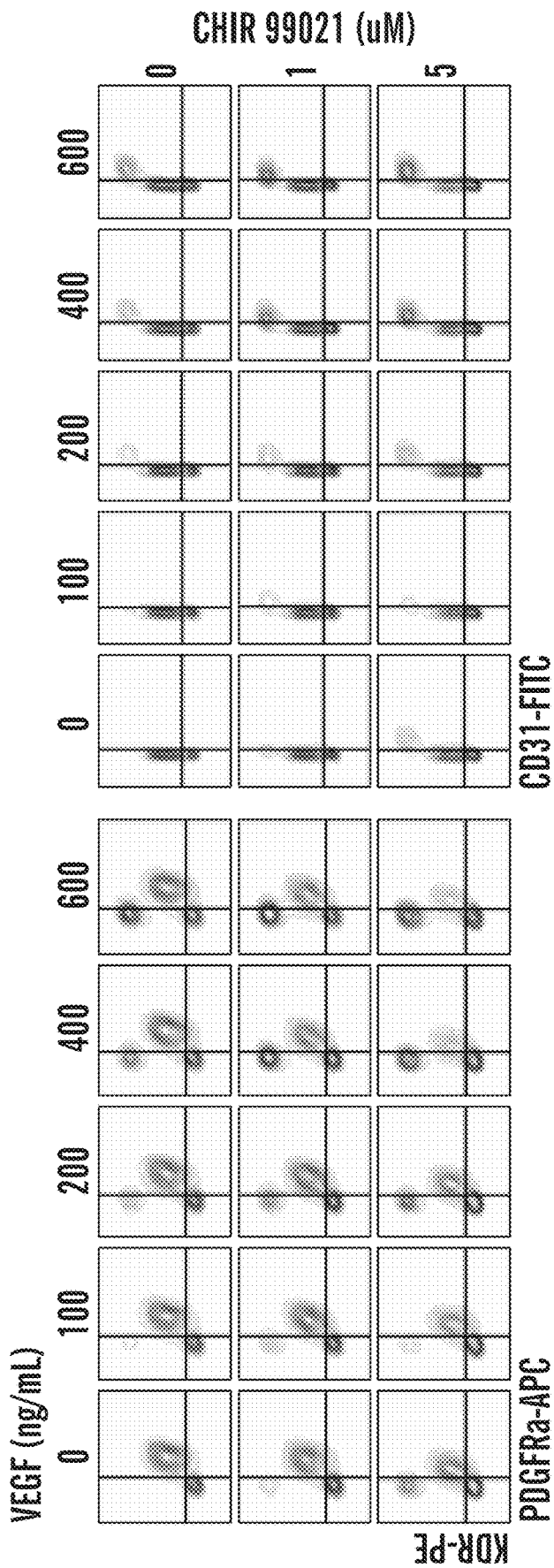
Figure 9D:
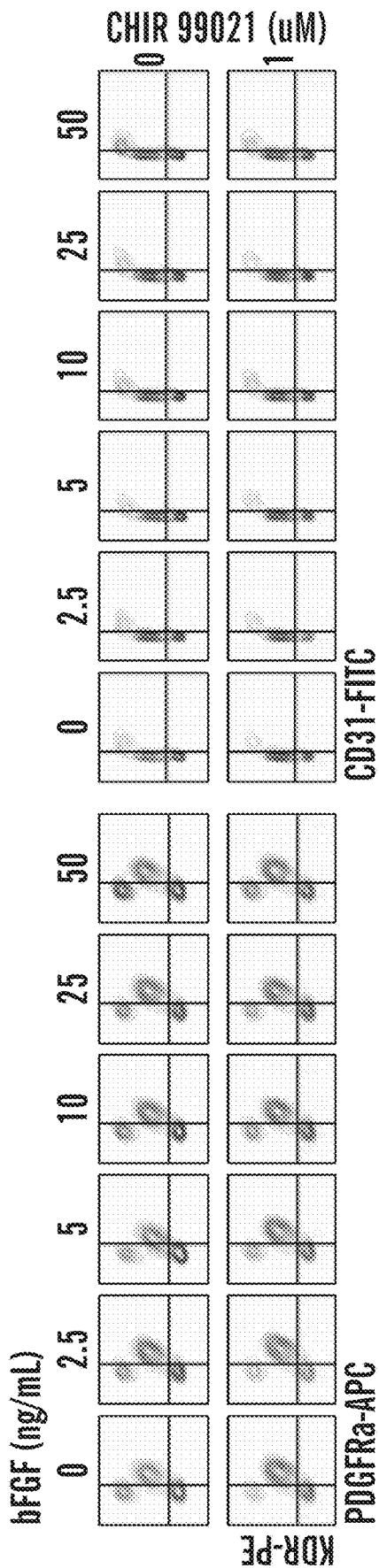
Figure 9E:
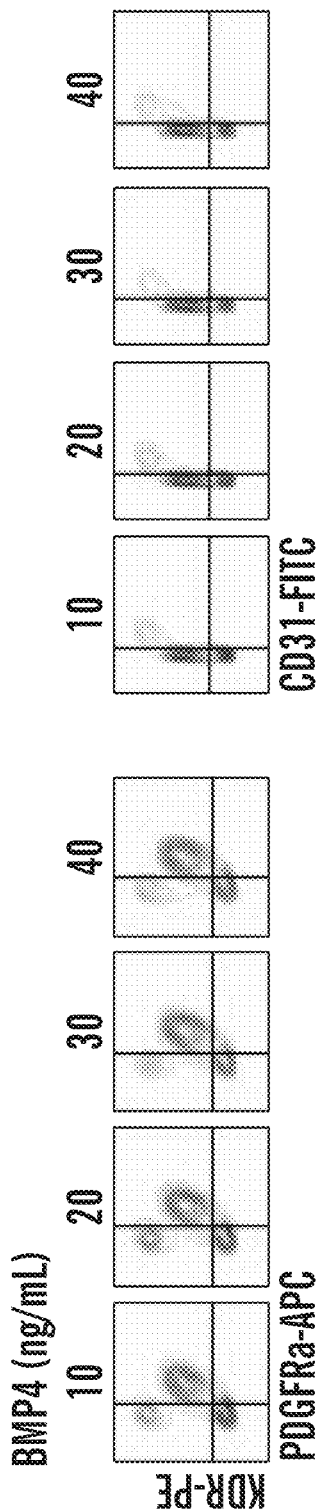
Figure 9F:
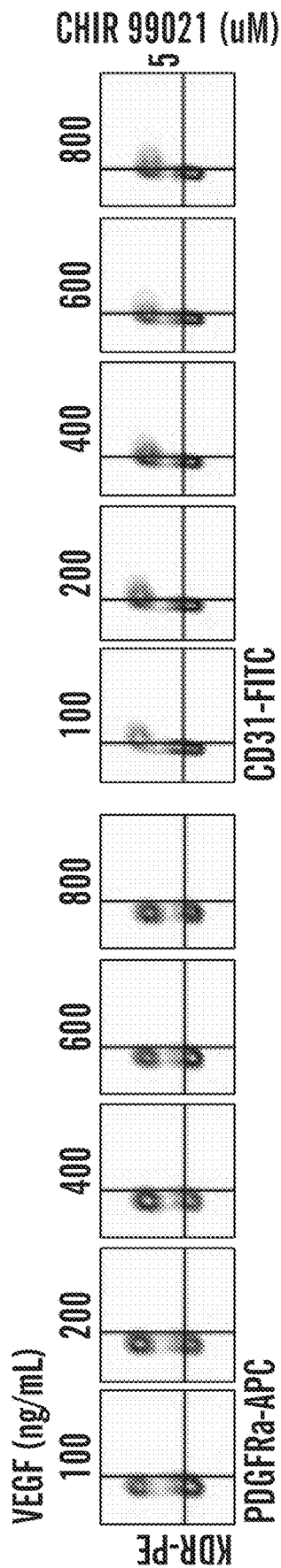
Figure 9G:
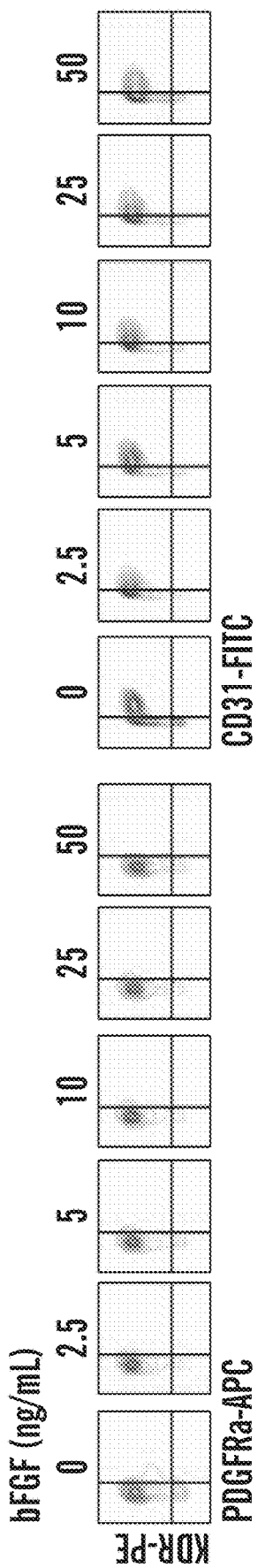
Figure 9H:
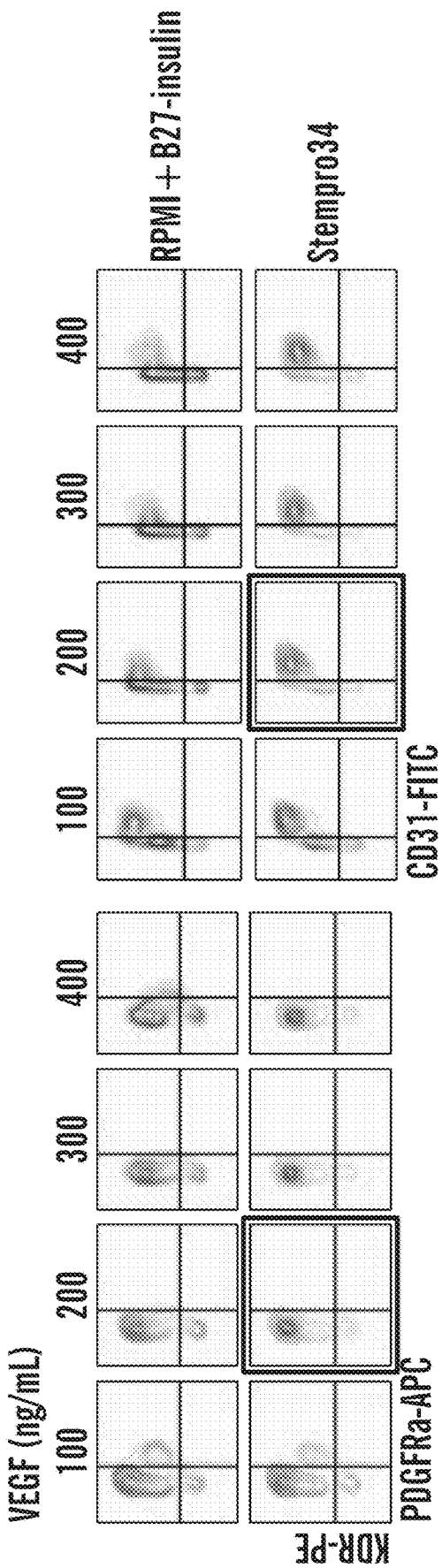
Figure 10A:
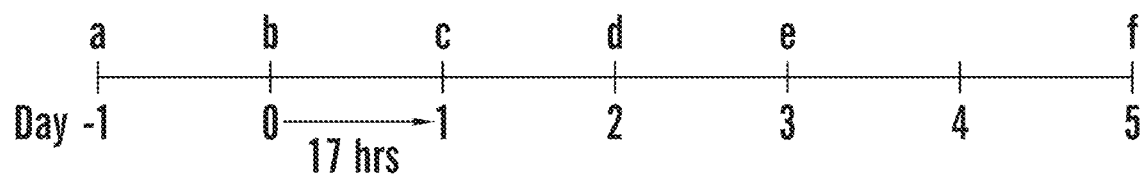
FIGS. 10A-10C Time dependency of VEGF treatment during endothelial differentiation.
Figure 10B:
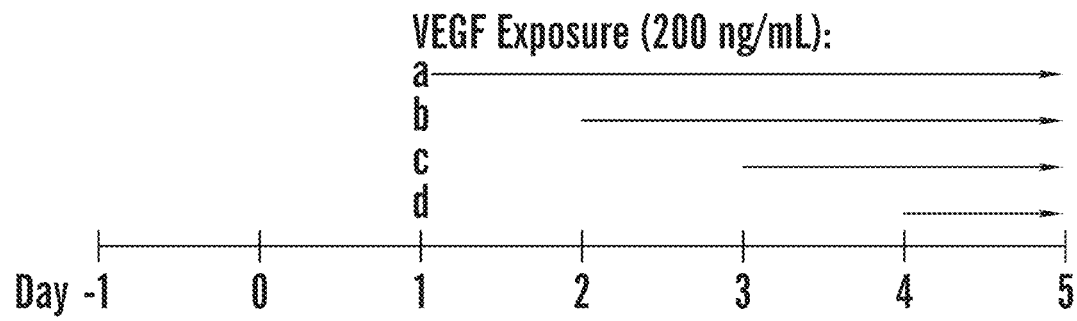
Figure 10B:
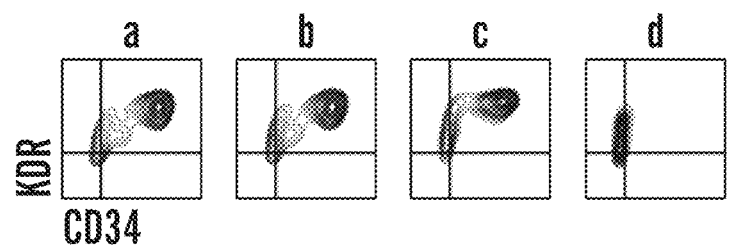
Figure 10C:
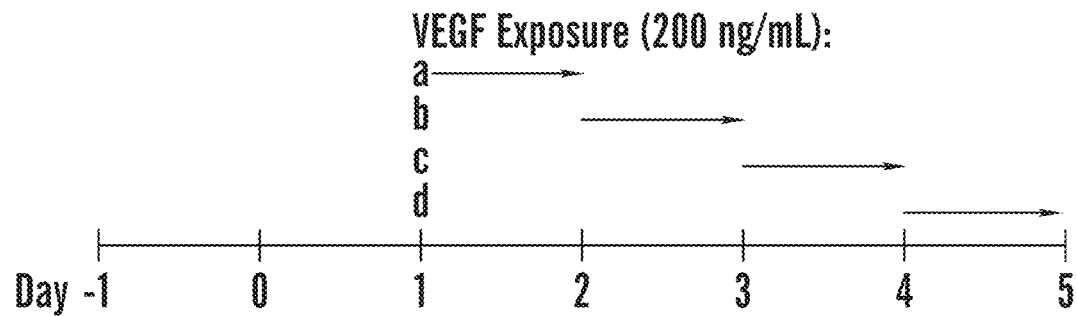
Figure 10C:
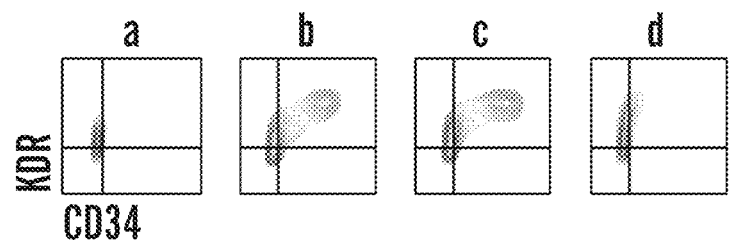

The protocol provided herein comprises a method for generating polarized mesoderm by induction of differentiation under varying concentrations of Activin A (day 0) and BMP4 (day 1) in RPMI media with B27 supplement minus insulin. MATRIGEL™ is added to the induction media in an effort to facilitate signaling cues for epithelial to mesenchymal transition that occurs during gastrulation (see e.g., Zhang et al[25]). However, not all cell lines require MATRIGEL™ for efficient differentiation. In keeping with developmental gradients of Activin A that direct polarization of mesoderm, cardiogenic mesoderm (mid-primitive streak) is derived under conditions of 100 ng/mL Activin A whereas hemogenic mesoderm (posterior-primitive streak) is derived under conditions of 50 ng/mL Activin A. RPMI media with B27 supplement minus insulin is utilized in both cases[7]. During exposure to Activin A (17-18 hrs), cells appear to tighten leaving acellular regions throughout the plate (FIG. 8B).

On day 1, media is changed to RPMI media with B27 supplement minus insulin containing the Wnt/β-catenin signaling agonist CHIR-99021. Cardiogenic mesoderm is derived from cultures exposed to 5 ng/mL BMP4 whereas hemogenic mesoderm is derived from cultures exposed to 40 ng/mL BMP4. It was empirically shown that mesoderm is formed on day 2 based on time-course assays of gene expression[7,8]. Under the conditions described, the cells transition from a compact state on day 1 to a dispersed monolayer throughout the plate on day 2 (FIG. 8C). Extensive characterization of these mesoderm populations was previously provided using gene expression, proteomics, and analysis of endogenous Wnt/β-catenin signaling activity[7]. Table 1 provides primers for quantitative RT-PCR for analysis of pan-mesoderm genes as well as those that show lineage specific expression in cardiogenic vs. hemogenic mesoderm. Cardiomyocyte purity is assessed at day 14 using FACS to detect cTnT+ cells. KDR+/CD34+ expression at day 5 is used as an indicator of purity during early stages of differentiation.

Cardiac Differentiation (Steps 13A-14)

Figure 3A:
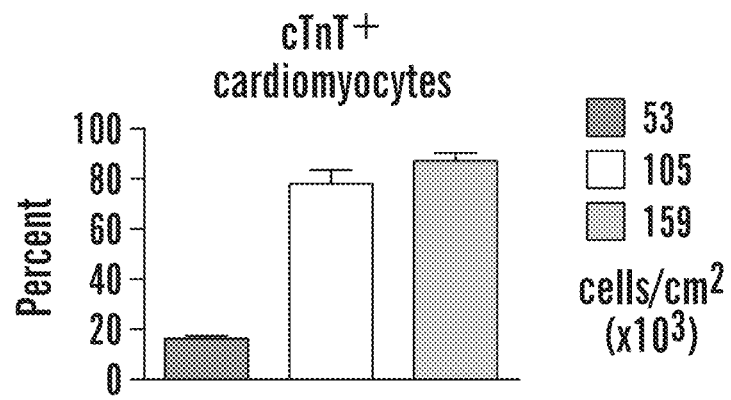
FIGS. 3A-3B Cardiac directed differentiation.

The efficiency of cardiac differentiation from pluripotency is directly related to the ability to specify mid-streak cardiogenic mesoderm as opposed to the more anterior-streak endoderm or posterior-streak hemogenic mesoderm. As shown previously, deviating away from precise specification of cardiogenic mesoderm has dramatic effects on the efficiency of cardiomyocyte differentiation[7]. It is shown herein that the density of cells has major implications for proper specification of high purity derivatives (FIG. 3A).

Proper dosage of Wnt/β-catenin signaling has been shown to be one of the major determinants of specification into the cardiac lineage[7,8,11,26–28]. Although Wnts are required for mesoderm specification, they must be inhibited to direct cells into the cardiac lineage[8,11,26,28]. An exogenous tankyrase inhibitor, XAV-939, was added on day 3 of differentiation to reinforce this key step during cardiac progenitor cell specification. Previous work has suggested that cardiac progenitor cells, which emerge on day 5 of differentiation, can be assessed for purity on the basis of KDR/PDGFRα expression[3,29].

Using the protocol described herein, a statistically significant negative correlation with KDR+/PDGFRα+ cells was found at day 5 vs. the efficiency of cardiac differentiation at day 14 and therefore this phenotyping approach[7] is not preferred. Table 1 provides primers for amplifying genes involved in specification of the cardiac progenitor cell including NKX2-5, GATA4, TMEM88, ISL1, and MYL4.

TABLE 1

Quantitative RT-PCR primers for human genes

| Gene Name | Forward Primer | Reverse Primer |
|---|---|---|
| *House keeping* | | |
| HPRT | TGACACTGGCAAAACAATGCA (SEQ ID NO: 1) | GGTCCTTTTCACCAGCAAGCT (SEQ ID NO: 2) |
| *Pan mesoderm* | | |
| T | CAAATCCTCATCCTCAGTTTG (SEQ ID NO: 3) | GTCAGAATAGGTTGGAGAATTG (SEQ ID NO: 4) |
| KDR | ATGCACGGCATCTGGGAATC (SEQ ID NO: 5) | GTCACTGTCCTGCAAGTTGCTGTC (SEQ ID NO: 6) |
| *Cardiogenic mesoderm* | | |
| NODAL | TGGAGGTGGGATGAAGTCACCTAT (SEQ ID NO: 7) | AACCCAGCCTGAGGCAATGAGATT (SEQ ID NO: 8) |
| DKK1 | AACAGCTATCCAAATGCAG (SEQ ID NO: 9) | TCACAGGGGAGTTCCATAAA (SEQ ID NO: 10) |
| MESP1 | TCGAAGTGGTTCCTTGGCAGAC (SEQ ID NO: 11) | CCTCCTGCTTGCCTACAAAGTGTC (SEQ ID NO: 12) |
| GSC | GAGGAGAAAGTGGAGGTCTGGTT (SEQ ID NO: 13) | CTCTGATGAGGACCGCTTCTG (SEQ ID NO: 14) |
| *Hemogenic mesoderm* | | |
| CDX1 | GGTGGCAGCGGTAAGACTC (SEQ ID NO: 15) | TGTAACGGCTGTAATGAAACTCC (SEQ ID NO: 16) |
| WNT8a | GCAGAGGCGGAACTGATCTT (SEQ ID NO: 17) | CGACCCTCTGTGCCATAGATG (SEQ ID NO: 18) |
| WNT3a | AACTACGTGGAGATCATGCCC (SEQ ID NO: 19) | GACTCCCTGGTAGCTTTGTC (SEQ ID NO: 20) |
| *Cardiac progenitor cells* | | |
| TMEM88 | GCTGCCTTCAATCTTCTCCTG (SEQ ID NO: 21) | ATAAAGGGCTCGGCTGTAGG (SEQ ID NO: 22) |
| GATA4 | ACACCCCAATCTCGATATGTTTG (SEQ ID NO: 23) | GTTGCACAGATAGTGACCCGT (SEQ ID NO: 24) |
| ISL1 | ATTTCCCTATGTGTTGGTTGC (SEQ ID NO: 25) | CGTTCTTGCTGAAGCCGATG (SEQ ID NO: 26) |
| NKX2.5 | CCAAGGACCCTAGAGCCGAA (SEQ ID NO: 27) | ATAGGCGGGGTAGGCGTTAT (SEQ ID NO: 28) |
| MYL4 | TCAAAGAGGCCTTTTCATTG (SEQ ID NO: 29) | CGTCTCAAAGTCCAGCATCT (SEQ ID NO: 30) |
| *Cardiomyocytes* | | |
| TNNT2 | TTCACCAAAGATCTGCTCCTCGCT (SEQ ID NO: 31) | TTATTACTGGTGTGGAGTGGGTGTGG (SEQ ID NO: 32) |
| MYH6 | CAAGTTGGAAGACGAGTGCT (SEQ ID NO: 33) | ATGGGCCTCTTGTAGAGCTT (SEQ ID NO: 34) |
| MYL7 | TCCAACGTCTTTTCCATGTT (SEQ ID NO: 35) | TCTGTCCCATTGAGCTTCTC (SEQ ID NO: 36) |
| TBX5 | GAACCACAAGATCACGCAATTA (SEQ ID NO: 37) | ACACCATTCTCACACTGGTAT (SEQ ID NO: 38) |
| ATP2A2 | ATGACAACCCACTGAGAAGAGAA (SEQ ID NO: 39) | CGAAGGTCAGATTGGTCTCATATTT (SEQ ID NO: 40) |

TABLE 1-continued

Quantitative RT-PCR primers for human genes

| Gene Name | Forward Primer | Reverse Primer |
|---|---|---|
| RYR2 | AGAACTTACACACACGCGACCTG (SEQ ID NO: 41) | CATCTCTAACCGGACCATACTGC (SEQ ID NO: 42) |
| Pan endothelium | | |
| SCL | AAGGGCACAGCATCTGTAGTCA (SEQ ID NO: 43) | AAGTCTTCAGCAGAGGGTCACGTA (SEQ ID NO: 44) |
| CD34 | AAATCCTCTTCCTCTGAGGCTGGA (SEQ ID NO: 45) | AAGAGGCAGCTGGTGATAAGGGTT (SEQ ID NO:46) |
| CD31 | ATCATTTCTAGCGCATGGCCTGGT (SEQ ID NO: 47) | ATTTGTGGAGGGCGAGGTCATAGA (SEQ ID NO: 48) |
| Endocardial endothelium | | |
| NFATC1 | GCATTTTCCTTGATCCCTGT (SEQ ID NO: 49) | AGCAGCTTTAGGGTGCAAAT (SEQ ID NO: 50) |
| Hemogenic endothelium | | |
| HAND1 | TCAAAGACGCACTCTTCCAC (SEQ ID NO: 51) | GTGCAGCGACAAAAAGAAAA (SEQ ID NO: 52) |
| GATA1 | CTTTCAGGTGTACCCATTGC (SEQ ID NO: 53) | AAAGTCTCCAGGAAGCTGGT (SEQ ID NO: 54) |
| RUNX1 | ATGTGGTCCTATTTAAGCCAGCCC (SEQ ID NO: 55) | TCATCTGGCTGAAGACACCAGCTT (SEQ ID NO: 56) |

Figure 3B:
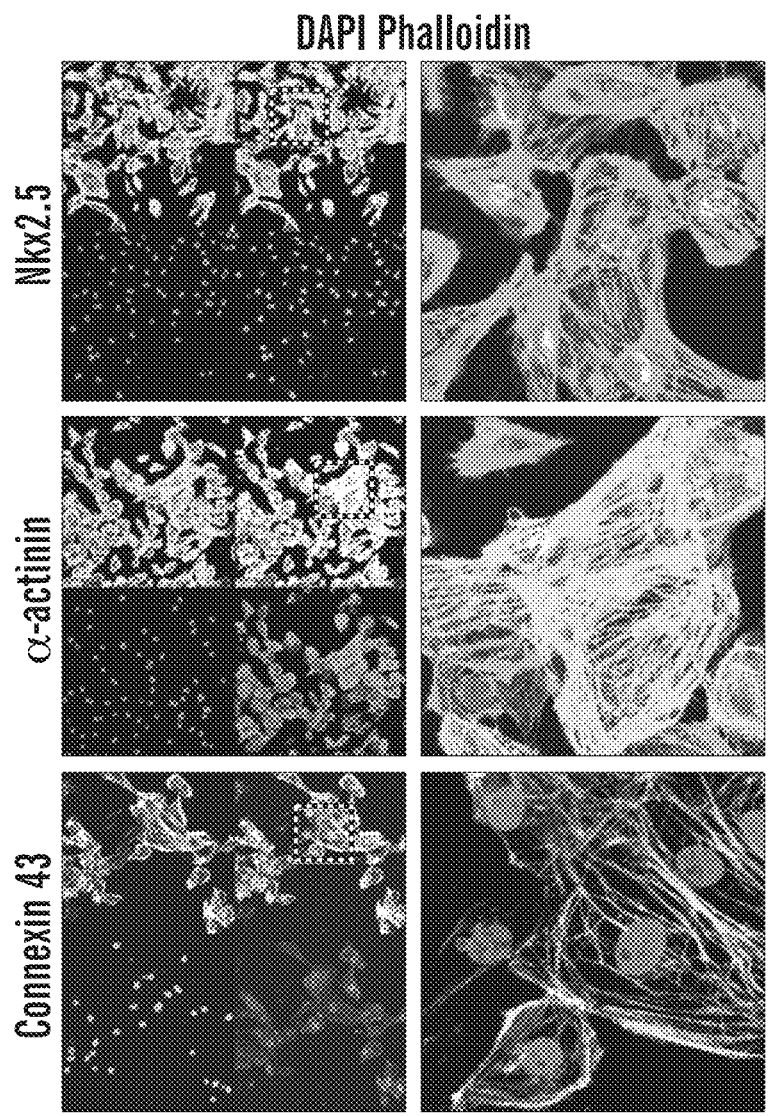

As the protocol progresses past the progenitor cell stage, insulin is used in a stage dependent manner during cardiac differentiation. This approach has been supported by studies showing that insulin is inhibitory prior to cardiac progenitor cell specification but required for definitive cardiomyocyte development[30]. Accordingly, RPMI media is changed on day 7 to include the B27 supplement containing insulin. Beating cardiomyocytes can be seen as early as day 7. Cells progressively mature to definitive cardiomyocytes by day 14 at which point they are approximately 90% cTnT+ by FACS analysis and express high levels of Nkx2-5, α-actinin, and the junctional protein connexin-43 (FIG. 3B). Methods for staining cardiomyocytes for quantification of cardiac Troponin T (cTnT) and smooth muscle actin (SMA) by FACS analysis is described herein under the heading "Flow cytometry analysis of hPSC-derived cardiomyocytes and ECs." SMA is expressed in immature cardiomyocytes but disappears as cardiomyocytes become more mature. Table 1 provides primers for amplifying genes expressed in definitive cardiomyocytes including myofilament genes TNNT2, MYH6, MYL7, the transcription factor TBX5, and calcium handling genes ATP2a2 and RYR2. For further phenotyping, previous protocols which have provided detailed methods for characterization of cardiomyocytes by immunohistochemistry[31] are recommended. As with other lineages outlined in the protocol, this protocol does not require purification (e.g. using selection or sorting[12,18–20,32]) at any point to achieve high purity cardiomyocytes.

Rationale for Method to Derive Distinct Endothelial Subtypes hPSCs have been used extensively in efforts to derive human endothelium[14,33–35]. Despite significant effort, the capacity to generate high purity endothelium from hPSCs has been met with modest success with efficiencies ranging from 5% to 30% cells positive for lineage markers including VE-cadherin, KDR, and CD34[13–17]. As such, most widely implemented protocols currently require cell sorting to enrich endothelial cells to purity[34–35]. This is problematic because it shows that control of cell fate choices into the endothelial lineage, despite being well understood during embryogenesis are not efficiently controlled in hPSC directed differentiation.

The current protocol provides two significant strides forward for hPSC directed differentiation into endothelium. First, developmental studies have shown distinct origins and mechanisms for specifying endocardial endothelium versus blood forming vascular endothelium[36–41]. To this end, using an approach of polarizing hPSC mesoderm at the onset of differentiation, this protocol provides the first approach for controlling endocardial vs. vascular endothelial differentiation. Secondly, unlike other protocols reported to date, conditions have been identified for directing differentiation into greater than 90% pure endothelium without any sorting steps.

Figure 4A:
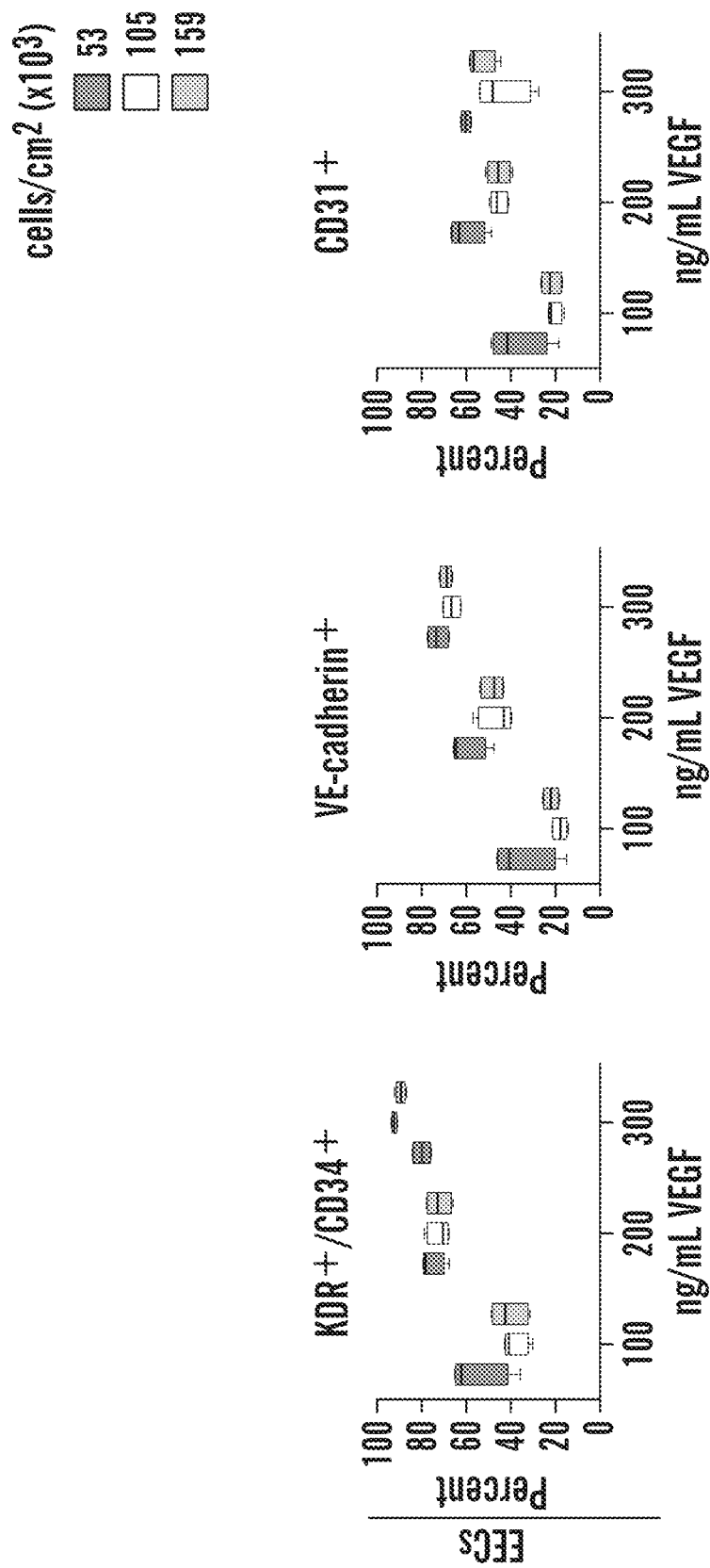
FIGS. 4A-4C Variables influencing endothelial differentiation efficiency.
Figure 4B:
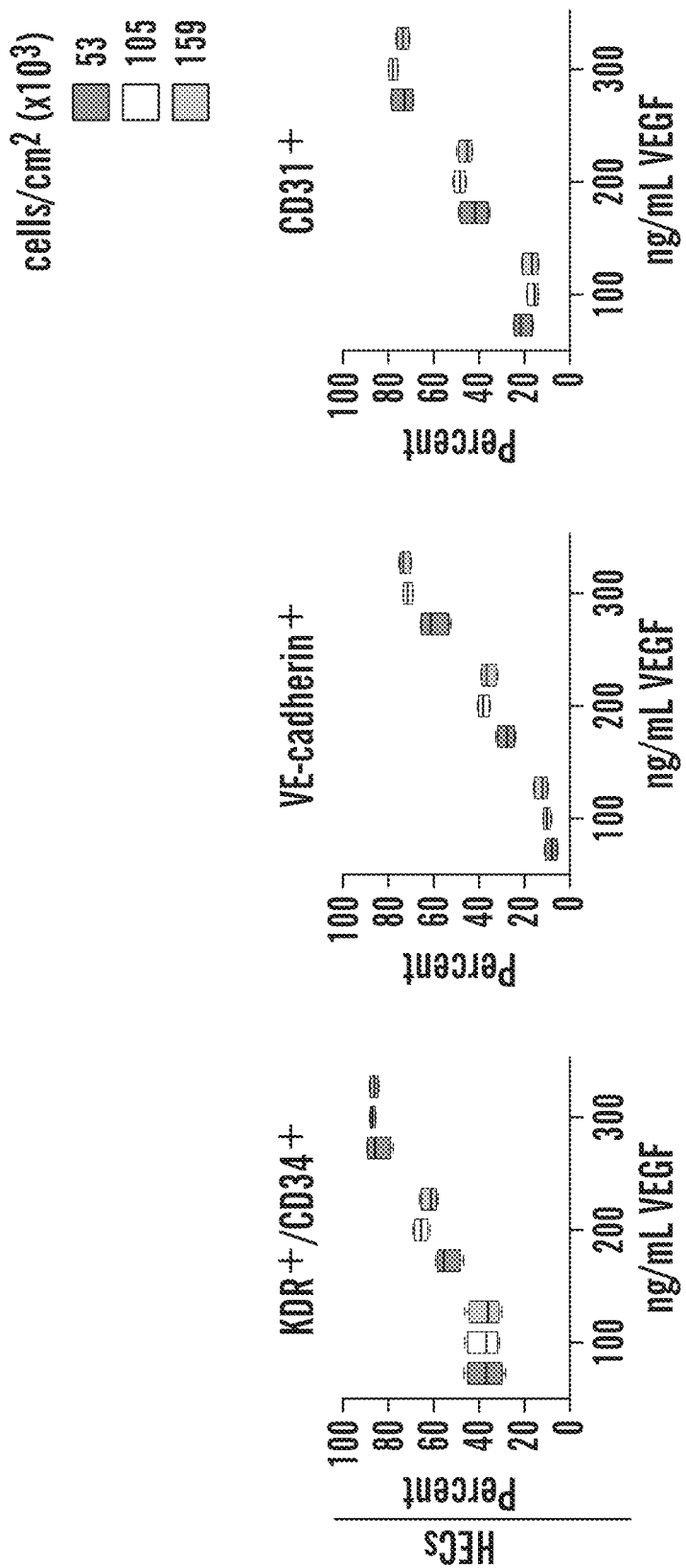
Figure 4C:
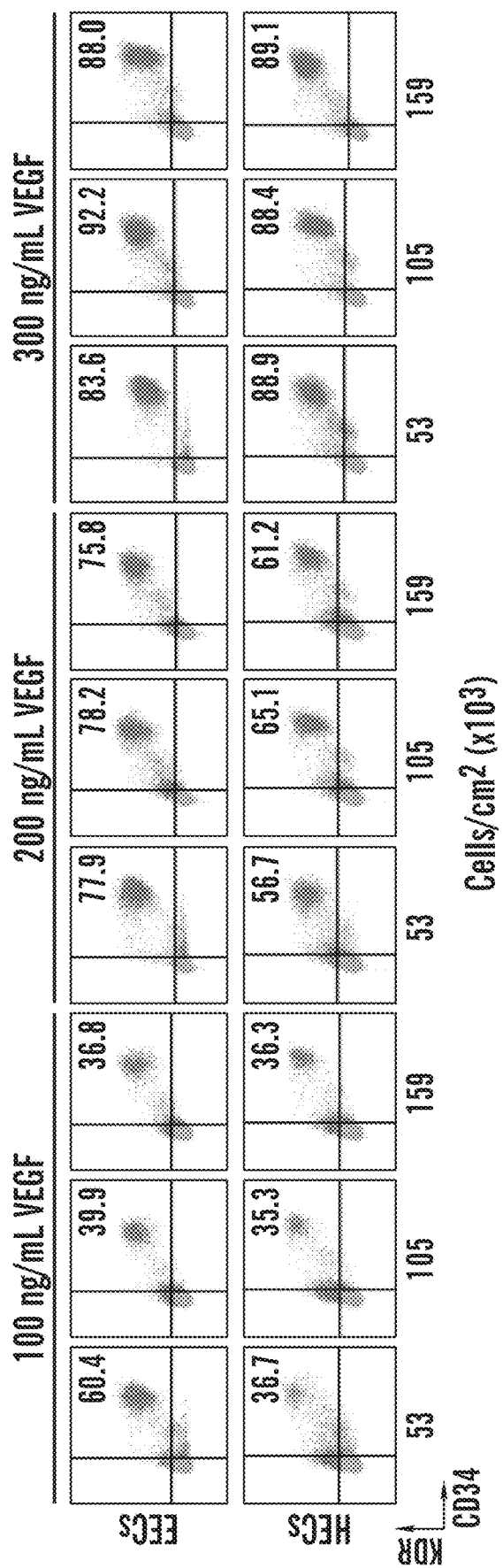

Previous work has shown the requirement for VEGF and active Wnt/β-catenin signaling in development of hemogenic endothelium[42,43]. Based on this, wide range of culture conditions, adapted from previous differentiation protocols[13–17], were tested to determine optimal parameters for differentiation of endothelium building from the monolayer directed mesodermal differentiation platform described herein (FIG. 9). These optimization studies led to some interesting observations. First, compared to the dramatic effects observed with cardiac differentiation, it was found that the seeding densities tested at the onset of differentiation did not markedly influence the purity of endothelial cells generated by this protocol (FIG. 4). Secondly, in contrast to current embryoid body protocols[13–15,17], high levels of VEGF stimulation are required to direct endothelial differentiation in a monolayer format (FIG. 2 & FIG. 4). Third, it was determined that cells remain responsive to VEGF stimulation between days 2 and 3 of differentiation but lack responsiveness prior to or after that window of time (FIG. 3). Lastly it was found that augmenting Wnt/β-catenin pathway activity using the agonist CHIR-99021 was inhibitory at all doses tested (FIG. 2). Among a wide range of conditions vetted, a protocol generating greater than 90% pure endocardial ECs and blood forming vascular ECs was designed. Differentiation of Endocardial and Hemogenic Endothelium (Steps 13 and 15)

In contrast to cardiomyocyte differentiation, which is highly sensitive to specification of hPSCs through cardiogenic mesoderm, endothelium is known to form from all mesodermal origins[1]. Similarly, this is also shown with hPSC endothelial differentiation[7]. However, endocardial vs. vascular endothelial subtypes are formed only through specification into cardiogenic vs. hemogenic mesoderm at the onset of differentiation. On day 2 when hPSCs have formed mesoderm, endothelial cell differentiation is directed by changing media to Stempro-34 containing VEGF, BMP4, bFGF, ascorbic acid, and monothioglycerol. Cells remain in this media until day 5. Endothelial purity is assayed at day 5 by FACS analysis for KDR+/CD34+ cells, however markers of definitive endothelium including VE-cadherin and CD31 are also evident at this time point (FIG. 4). A major limitation currently is the lack of cell markers that distinguish endocardial vs. hemogenic ECs by FACS. Exemplary methods are provided herein for staining ECs for analysis of KDR and CD34 by FACS analysis. Table 1 outlines primers for quantitative RT-PCR analysis of pan-endothelial markers (e.g. SCL) vs. those that specifically identify endocardial endothelium (e.g. NFATC1) vs. blood forming endothelium (e.g. GATA1, RUNX1, and HAND1).

Findings during mouse development have shown that endocardial endothelium has very limited, transient hematopoietic activity whereas the posterior-streak derived hemogenic endothelium is the primary source for blood formation in development[44]. It has been shown that the hPSC endocardial endothelium exhibits very modest blood forming activity largely giving rise to purely primitive erythroid derivatives while hemogenic endothelium has the capacity for both the erythroid and myeloid lineages[7].

Figures 5A, 5B:
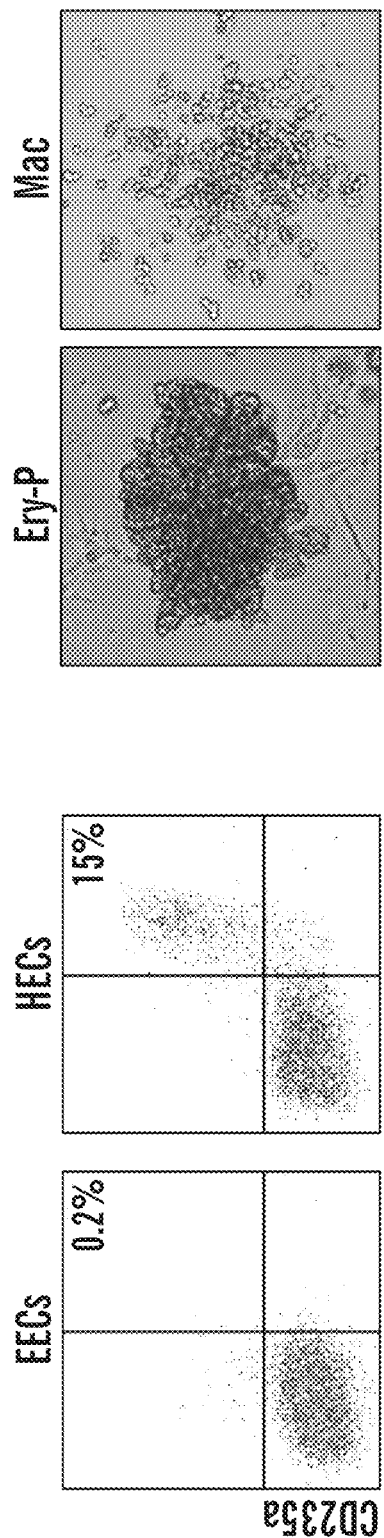
FIGS. 5A-5B Hematopoiesis assays from hESC-ECs.
Figure 6A:
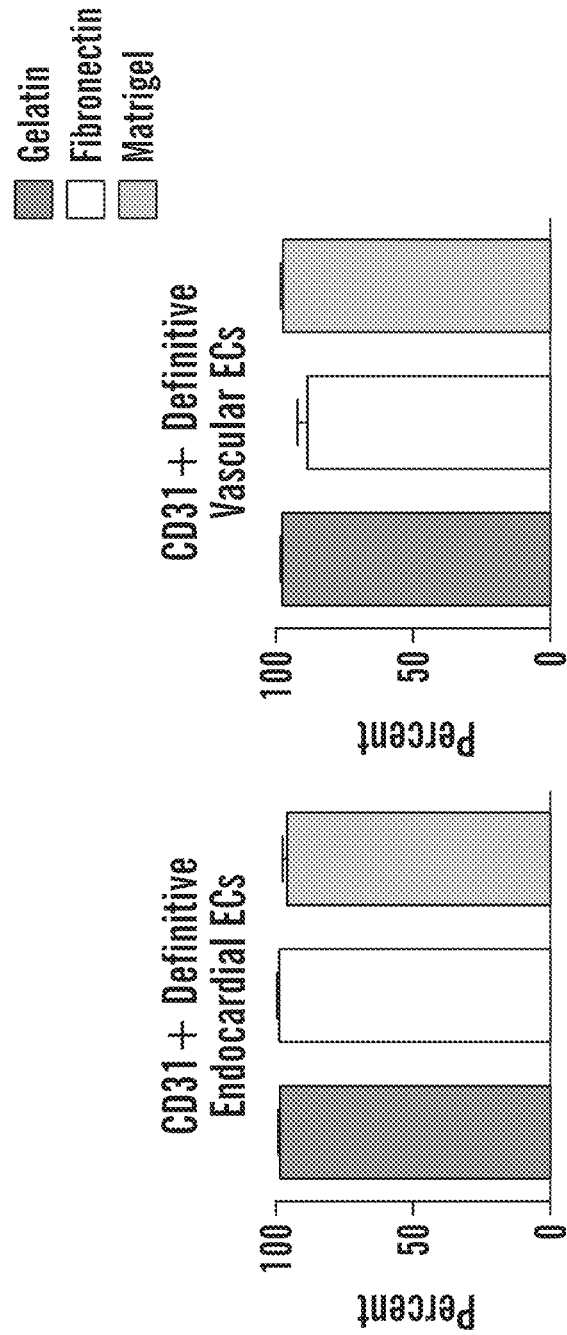

In contrast the hPSC cardiac progenitor cells have no blood forming activity[8]. As described in the section entitled "Flow cytometry analysis of hPSC-derived cardiomyocytes and ECs," phenotyping of day 5 cells is used initially to characterize primitive erythroid cell types based on percent CD43+/CD235a+ cells, which are present only within the HEC population (FIG. 5A)[7]. As a secondary assay, provided herein in the section entitled "Primitive hematopoietic colony forming assays" is a brief description for the blood colony forming assay in methylcellulose as a functional endpoint for assessing day 5 endocardial vs. blood-forming endothelium (FIG. 5B). Methods for differentiation into later stage hematopoietic derivatives have been described elsewhere[7,8,45]. To mature cells into definitive endocardial ECs and vascular ECs, day 5 cells are passaged for expansion in endothelial growth media (EGM) containing VEGF, bFGF, and CHIR-99021 for an additional 5-10 days. A number of matrix substrates were tested to determine their effect on maturation of ECs including MATRIGEL™, fibronectin, and gelatin and found no significant difference (FIG. 6A). It was found that differentiation under these conditions led to near 99% CD31+ ECs for both endocardial and vascular ECs without requiring sorting (FIGS. 6A, 6B).

Previously, marked differences in the functionality of endocardial vs. vascular ECs have been shown in the context of engineered microvascular networks[7]. Given the technically specialized nature of this method[46], a more classic approach is provided for assaying EC functionality on the basis of lumen formation in collagen gels (see section entitled "Collagen-based tubulogenesis assay"). Previous protocols have also provided extensive details for performing immunohistochemistry for endothelial markers as well as a variety of additional functional endpoints for assaying ECs in vitro and in vivo[34,35].

Materials

Exemplary Reagents Used in this Study
1-Thioglycerol (MTG) (Sigma, M6145-25 mL)
1× StemPro-34 SFM (Life Technologies, cat. no. 10639-011)
Activin A (R&D Systems, cat. no. 338-AC)
APC conjugated donkey anti-rabbit IgG antibody (Jackson, cat. no. 711-136-152)
APC conjugated mouse anti human CD43 antibody (BD, cat. no. 560198)
B-27 supplement (Life Technologies, cat. no. 17504-044)
B-27 supplement minus insulin (Life Technologies, cat. no. A18956-01)
bFGF (PeproTech Inc., cat. no. AF-100-18B)
BMP4 (R&D Systems, cat. no. 314-BP)
Bovine serum albumin (BSA) (Sigma, cat. no. A9418-50G)
CHIR-99021 (Chiron) (Cayman Chemical Company, cat. no. 13122)
DMEM (Life Technologies, cat. no. 10313-021)
DMEM/F12 (Life Technologies, cat. no. 11320-033)
DMSO (Sigma, cat. no. D2650)
DNase 1, Bovine pancreas (Calbiochem, cat. no. 260913)
Endothelial Growth Media (EGM) BulletKit (Lonza, cat. no. CC-3124)
Fetal bovine serum (HyClone, at. No. SH30396.03)
FITC mouse anti-human CD31 antibody (BD Pharmingen, cat. no. 555445)
Gelatin solution, 5% (Sigma, cat. no. G1393-100 mL)
Hydrochloric acid, 12 M (Fisher, cat. no. A14451-212)
L-Ascorbic acid 2-phosphate sequimagnesium salt hydrate (Sigma, cat. no. A8960-5G)
L-Glutamine (Life Technologies, cat. no. 25030-081)
MATRIGEL™ (Corning, cat. no. 356231)
Mouse IgG (FITC) isotype Control (abcam, cat. no. ab37356)
Mouse IgG1 isotype Control (eBioscience, cat. no. 14-4714-85)
mTeSR1 Complete Kit (Stem Cell Technologies, cat. no. 05850)
Paraformaldehyde solution, 4% (Affymetric Inc., cat. no. 199943)
PBS (Life Technologies, cat. no. 14190-144)
PE conjugated Anti-human VEGF R2/KDR mouse IgG1 antibody (R&D, cat. no. FAB357P)
PE conjugated goat anti-mouse IgG antibody (Jackson, cat. no. 115-116-146)
PE/Cy7 conjugated mouse IgG1 isotype Control (BioLegend, cat. no. 400125)
PECy7 conjugated mouse anti-human CD235a antibody (BD Pharmingen, cat. no. 563666)
PECy7 mouse IgG1 isotype control (Biolegend, cat. no. 400125)
Penicillin Streptomycin (Life Technologies, cat. no. 15140-122)
PerCP conjugated anti-human CD34 antibody (BD, cat. no. 340430)
PerCP conjugated mouse IgG1 isotype Control (BD Pharmingen, cat. no. 559425)
Rabbit anti-alpha smooth muscle Actin antibody [E184] (Abcam, cat. no. ab32575)
Rabbit IgG isotype Control (abcam, cat. no. ab171870)
RLT lysis buffer (Qiagen, cat. no. 101576)
RPMI Media (Life Technologies, cat. no. 11875-093)

RUES2 cells
Saponin, from Quillaja Bark (Sigma, cat. no. S7900-100G)
Tris Base (Fisher, cat. no. BP152-500)
Troponin T Cardiac Isoform antibody (Thermo Scientific, cat. no. MA5-12960)
Trypsin, 2.5% (Life Technologies, cat. no. 15090-046)
VE-Cadherin antibody (abcam, cat. no. 7047)
VEGF (PeproTech Inc., cat. no. 100-20)
VERSENE™ (Life Technologies, cat. no. 15040-066)
XAV-939 (Tocris Bioscience, cat. no. 3748)
Y-27632 (Tocris Bioscience, cat. no. 1254)
β-Mercaptoethanol (βME) (Life Technologies, cat. no. 21985-023)
CAUTION β-Mercaptoethanol is combustible, corrosive and toxic in case of ingestion and skin absorption; keep it away from sources of ignition, and avoid direct contact with skin.

Exemplary Equipment Used in this Study
100 mM plates (Corning, cat. no. 353003)
24-well plates (Corning, cat. no. 353047)
5 mL polystyrene round-bottom tube (Corning, cat. no. 352054)
CL2 centrifuge (Thermo Scientific, cat. no. 66001 BA)
Conical tubes (15 and 50 mL; Thermo Scientific, cat. nos. 339651 and 339653)
FACS machine (BD; FACSCanto II, 2-laser, 6-color)
FACS acquisition software (BD; FACSDiva)
FACS analysis software (FlowJo; version 9.8.5)
Hemocytometer (Fisher Scientific, cat. no. 0267110)
Humidified tissue culture incubator (37° C., 5% CO2, Heraeus, HERA Cell, cat. no. 51013669)
Inverted contrasting microscope (Leica, DMIL, cat. no. 090-135-001)
Serological pipettes (5, 10, 25, and 50 mL; Costar, cat. nos. 4487, 4488, 4489, and 4490)
Shel Lab H2O bath incubator (Sheldon Manufacturing Inc., cat. no. W14M)
Sterile biological safety cabinets (NUAIRE, Class II Type A2)
Sterile filters (125, 250, 500, and 1000 mL; Thermo Scientific, cat. nos. 565-0020, 568-0020, 569-0020, and 567-0020)
Sterilized Pasteur pipettes (VWR, cat. no. 14672-200)
Reagent reservoir (50 mL; Costar, cat. no. 4870)

Exemplary Reagent Setup
Activin A (10 µg mL-1) In a sterile hood, on ice, add 5 mL of 0.4 mM HCl in 0.1% BSA-PBS to a 50 µg vial of Activin A and dissolve. Divide into aliquots and store at −20° C. for up to 6 months.

BMP4 (10 µg mL-1) In a sterile hood, on ice, add 5 mL of 0.4 mM HCl in 0.1% BSA-PBS to a 50 µg vial of BMP4 and dissolve. Divide aliquots and store at −80° C. for up to 6 months.

bFGF (10 µg mL-1) In a sterile hood, on ice, reconstitute a 1 mg vial of bFGF using 100 mL of 10 mM Tris (pH 7.6) in 0.1% BSA-H2O. Divide into 800-µl and 400-µl aliquots in 1.5 mL tubes and store at −80° C. for up to 1 year.

VEGF (500 µg mL-1) In a sterile hood, on ice, reconstitute 1 vial (50 µg) of VEGF powder in 100 µl of 0.05% BSA-H2O. Divide in 5-µl aliquots and store at −80° C. Single-use only. Use immediately after thawing.

CHIR-99021 (25 mM) In a sterile hood, add 860 µl of DMSO to 10 mg of CHIR-99021. Divide the solution into aliquots and store at −20° C. for up to 1 year.

XAV-939, 10 mM In a sterile hood, add 3.2 mL of room temperature DMSO to one 10 mg vial of XAV-939 and re-suspend. Divide the solution into 100-µl aliquots in 1.5 mL tubes and store at −20° C. for up to 1 month.

Y-27632, 10 mM Re-suspend at a concentration of 20 mM in a sterile hood, on ice, add the appropriate volume of DMSO to the 50 mg vial and dissolve. Divide solution into aliquots in and store them at −20° C. for up to 1 year.

1 M Tris (pH 7.6) (500 mL) In a sterile hood, add 60.57 g of Tris base to 350 mL of Millipore water. QS solution to 500 mL and adjust pH to 7.6±0.1. Solution can be stored at room temperature for up to 1 year.

10 mM Tris (pH 7.6) in 0.1% BSA-H2O (500 mL) In a sterile hood, add 5 mL of 1 M Tris (pH 7.6) solution to 495 mL of 0.1% BSA-H2O solution and sterile filter using a 500 mL sterile filter. Store at 4° C. for up to 1 year.

BSA-H2O, 0.05% (wt/vol) (100 mL) In a sterile hood, add 50 mg of bovine serum albumin to 100 mL of Millipore H2O and filter using a 125 liter sterile filter. Store this solution at 4° C. for up to 1 year.

BSA-PBS, 0.1% (wt/vol) (1000 mL) In a sterile hood, add 1 g of bovine serum albumin to 1000 mL of PBS and filter using a 1 liter sterile filter. Store this solution at 4° C. for up to 1 year.

0.4 mM HCl in 0.1% BSA-PBS (1000 mL) In a sterile hood, add 33.33 µl of 12 M HCl solution to 1000 mL of 0.1% BSA-PBS and mix thoroughly. Store this solution at 4° C. for up to 6 months.

FBS-PBS, 5% (vol/vol) (500 mL) In a sterile hood, mix 25 mL of FBS with 475 mL of PBS. The solution can be stored at 4° C. for up to 6 months.

Gelatin-H2O, 0.1% (vol/vol) (500 mL) In a sterile hood, mix 10 mL of 5% Gelatin solution with 490 mL of Millipore water. Filter using a 500 mL sterile filter. If the 5% stock gelatin solution is congealed, warm in 37° C. water bath until dissolved. The solution can be stored at 4° C. for up to 6 months.

30× MATRIGEL™-DMEM/F12 (20 mL) In a sterile hood, add 10 mL of 4° C. DMEM/F12 to 1 vial (10 mL) of 60× MATRIGEL™ at 4° C. and resuspend. MATRIGEL™ is very sensitive to changes in temperature and may gel if not aliquoted quickly. Aliquot and freeze at −20° C. The solution can be stored at 4° C. for up to 6 months.

Trypsin-VERSENE™ solution, 10% (vol/vol) (10 mL) In a sterile hood, gently mix 1 mL of 2.5% Trypsin at 4° C. with 9 mL of VERSENE™ at 37° C. in a 15 mL conical tube. The inventors do not recommend storing this solution.

Stop solution In a sterile hood, gently mix equal volumes of FBS and DMEM/F12 with 200 Units mL-1 of DNase 1.

0.75% Saponin in FBS-PBS (5%) (wt/vol) (500 mL) In a sterile hood, mix 3.75 g of dry Saponin with 500 mL of 5% FBS-PBS. Saponin is a very dangerous, light chemical that must be weighed in a fume hood. After thoroughly mixing, filter using a 500 mL sterile filter. The solution can be stored at 4° C. for up to 6 months.

mTeSR1 basal media+1× mTeSR1 supplement+1 µg mL-1 penicillin streptomycin (500 mL) In a sterile hood, add 1 5× mTeSR1 supplement vial (100 mL) to 400 mL of mTeSR1 basal media and mix thoroughly. Additionally, mix 5 mL of 10 mg mL-1 pen/strep with 495 mL of mTeSR1 medium. The medium can be stored at 4° C. for up to 4 weeks. If mTeSR1 media is mentioned after this point, it is assumed to have the supplement added.

RPMI+100 ng (or 50 ng) mL-1 Activin A+1× B-27 without insulin+1× MATRIGEL™ In a sterile hood, add appropriate volumes (See "PROCEDURE" section for protocols) of 10 µg mL-1 Activin A, 50× B-27 without insulin, and 30× MATRIGEL™-DMEM/F12 solution to RPMI to achieve your total desired volume (See Table 2 for respective plate format volumes). The inventors do not recommend storing this solution.

RPMI+5 ng (or 40 ng) mL-1 BMP4+1 µM CHIR-99021+1× B-27 without insulin In a sterile hood, add appropriate volumes (See "PROCEDURE" section for protocols) of 10 µg mL-1 BMP4, 25 mM CHIR-99021, and 50× B-27 minus insulin to RPMI to achieve the total desired volume (See Table 2 for respective plate format volumes). The inventors do not recommend storing this solution.

RPMI+1 µM XAV 939+1× B-27 without insulin In a sterile hood, add appropriate volumes (See "PROCEDURE" section for protocols) of 3.3 mM XAV 939 and 50× B-27 minus insulin to RPMI to achieve the total desired volume (See Table 2 for respective plate format volumes). The inventors do not recommend storing this solution.

RPMI+1× B-27 minus (or plus) insulin (510 mL) In a sterile hood, add one vial (10 mL) of 50× B-27 minus (or plus) insulin to 500 mL of RPMI. The inventors do not recommend storing this solution.

StemPro+100 mM MTG+100 mM L-Glutamine+50 mg mL-1 Ascorbic Acid+10 µg mL-1 BMP4+5 µg mL-1 bFGF+300 µg mL-1 VEGF (25 mL) In a sterile hood, add appropriate volumes (See "PROCEDURE" section for protocols) of 1M MTG, 1M L-glutamine, 5 mg mL-1 ascorbic acid, 10 µg mL-1 BMP4, 10 µg mL-1 bFGF, and 500 µg mL-1 VEGF to StemPro media to achieve the total desired volume (See Table 2 for respective plate format volumes). The inventors do not recommend storing this solution.

EBM+EGM Supplements In a sterile hood, thoroughly mix EGM supplements with EBM (500 mL). The media can be stored at 4° C. for up to 2 weeks. If mentioned after this point, EGM refers to EBM with EGM supplements already added.

EGM+20 ng mL-1 VEGF+20 ng mL-1 bFGF+1 µM CHIR-99021 In a sterile hood, add appropriate volumes (See "PROCEDURE" section for protocols) of 100 µg mL-1 VEGF, 10 µg mL-1 bFGF, and 25 mM CHIR-99021 to StemPro media to achieve your total desired volume (See Table 2 for respective plate format volumes). The inventors do not recommend storing this solution.

Exemplary Equipment Setup Used in this Study

MATRIGEL™-coated plates (25 mL) In a sterile hood, gently mix 0.83 mL of MATRIGEL™-DMEM/F12 30× with 24.17 mL of DMEM/F12 in a 50-mL conical tube. Immediately add MATRIGEL™ in DMEM/F12 at a volume of 6 mL per 10-cm plate or 500 µl per well of a 24-well plate. Allow the MATRIGEL™ to set overnight at 4° C. The MATRIGEL™-coated plates can be stored at 4° C. for up to 3 weeks.

Gelatin-H$_2$O-coated plates, 0.1% (vol/vol) In a sterile hood, add 6 mL of Gelatin-H$_2$O solution per 10-cm plate or 500 µl per well of a 24-well plate. Allow the Gelatin-H$_2$O solution to set at room temperature for 10 minutes. Use Gelatin-H$_2$O-coated plates immediately. The inventors do not recommend storing any Gelatin-H$_2$O coated plates for later use.

Procedure

Feeder-Free Culture of hPSCs•TIMING 30 Min (Plus 4 d for Maintenance)

Step 1| Take a MATRIGEL™-coated plate from 4° C. and place it in a biological safety cabinet at room temperature for 15 minutes to warm.

Step 2| Remove hPSCs, such as RUES2s (Rockefeller University), from liquid N$_2$ and thaw.

Step 3| Transfer cells to a 50 mL conical tube containing 5 mL of mTeSR1 media with 1 µg mL-1 penicillin streptomycin.

Step 4| Centrifuge the cell suspension at 200 g for 5 min at room temperature. Aspirate and discard the supernatant with a sterilized Pasteur pipette.

Step 5| Using a 5-mL pipette, gently re-suspend the cell pellet in mTeSR1 medium+10 µM Y27632+1 µg mL-1 penicillin streptomycin. Limit the number of triturations. Count cells. After aspirating the liquid from the warmed MATRIGEL™-coated plate, slowly add cells to media for a plating density of ~1.2×10$^4$ cells cm-2. Put plate into a 37° C., 5% CO$_2$ incubator. Move plate in quick, short, to-and-fro and side-to-side motions to evenly distribute the cells across the surface and leave undisturbed overnight. (Note: Including Y-27632 is very important for high hPSC recovery after freezing and thawing).

Step 6| The next day, aspirate the medium and replace with fresh 37° C. mTeSR1 medium containing 1 µg mL-1 penicillin streptomycin. Repeat this medium replacement daily until the cells are ready for passage (Step 7).

Passaging hPSCs Using VERSENE™•TIMING 20 Min (Plus 4 d for Maintenance)

Step 7| When the cells are 75-85% confluent or if individual colonies is wider than the diameter of the field with 10× magnification, aspirate the old medium and add room temperature PBS. Aspirate the PBS and add 37° C. VERSENE™.

Step 8| Incubate the plate at 37° C., 5% CO2 and wait for 2 min. Monitor the progress of cell detachment by viewing with a microscope. Continue until the cells in the center of colonies begin to round up.

Step 9| Aspirate the VERSENE™. Re-suspend single cells using mTeSR1+10 µM Y27632 by washing plate starting at the bottom and working side-to-side until reaching the top. Continue this process until all of the cells are detached. Be sure to limit the number of triturations. After the cells are removed from the surface of the well, add the contents of the well into a sterile conical tube.

Step 10| Aspirate the liquid from a room temperature MATRIGEL™-coated plate. Add mTeSR1+10 µM Y27632+1 µg mL-1 penicillin streptomycin to the plate. Then slowly add a fraction of the cell suspension from Step 9 to the plate. Place the plate in the incubator. Move the plate in quick, short, to-and-fro and side-to-side motions to evenly distribute the cells across the surface of the plate. Leave the plate undisturbed overnight.

Step 11| The next day, aspirate the medium and replace it with fresh 37° C. mTeSR1+1 µg mL-1 penicillin streptomycin. Repeat this medium replacement daily until the cells are 75-85% confluent or any one individual colony is wider than the diameter of the viewing field in 10× view (the amount of time this takes depends on the split ratio); daily monitoring is necessary. Pluripotent cell culture can be maintained by repeating Steps 7-11 before moving to the next steps for monolayer differentiations of hPSCs.

Monolayer Differentiation Setup of hPSCs•TIMING 20 Minutes

Step 12| For cells prepared for differentiation add appropriate volume of cells from step 9 to a volume of 37° C. mTeSR1+1 µM CHIR-99021+10 µM Y27632 resulting in appropriate concentration of cells to achieve proper seeding density (See FIGS. 4 & 5). Differentiation conditions have been optimized in a 24 well plate but can be expanded to accommodate any format.

Directed Differentiation into Polarized Mesodermal Lineages

Both cardiogenic and hemogenic mesoderm can readily be derived from hPSCs by varying Activin A and BMP4 concentrations on days 0 and 1, respectively. Differentiation into cardiomyocytes (Option 13A) requires a plating density of around $1.6 \times 10^5$ cells cm-2 whereas hemogenic endothelial mesoderm differentiation (Option 13B) is more amenable to variable densities without compromising efficiency.

Step 13| (A) Cardiogenic Mesoderm Differentiation•TIMING 2 Days (i) Aspirate media and wash the wells with an equal volume of PBS. Aspirate PBS and add the appropriate volume to each well (Table 2) of 37° C. RPMI+100 ng mL-1 Activin A+1× B-27 without insulin+1× MATRIGEL™ to each well of the plate. Incubate the plate for 17 hours at 37° C., 5% $CO_2$. This is designated day 0.

(ii) On day 1, aspirate the Activin A-containing media and add the appropriate volume to each well (Table 2) of 37° C. RPMI+5 ng mL-1 BMP4+1 μM CHIR-99021+1× B-27 without insulin to each well of the plate. Place the plate in the incubator.

(iii) Note: To generate endocardial endothelial cells (EECs), leave the media unchanged for 24 hours (until day 2) and then go to Steps 15(i-iv). To generate cardiomyocytes, leave the media unchanged for 48 hours (until day 3) and then go to Steps 14(i-iii).

TABLE 2

Media volumes for cell feeding during differentiation based on plate format

| | Plate Size | | | | |
|---|---|---|---|---|---|
| mL/well added on: | 24 wp | 12 wp | 6 wp | 10 cm | 15 cm |
| Day 0 (Activin A) | 0.5 | 1 | 1.5 | 10 | 30 |
| All other feedings | 1 | 2 | 4 | 20 | 60 |

TABLE 3

Antibody Information

| Antibody | Application | Stage | Vendor (cat#) | Dilution | Conjugate |
|---|---|---|---|---|---|
| cTnT | IHC/FACS | Primary | Thermo | 1:100 | N/A |
| SMA | FACS | Primary | Abcam | 1:50 | N/A |
| KDR | FACS | N/A | R&D | 1:6 | PE |
| CD34 | FACS | N/A | BD | 1:5 | PerCP |
| CD43 | FACS | N/A | BD | 1:5 | APC |
| CD235a | FACS | N/A | BD | 1:37 | PECy-7 |
| CD31 | IHC | Primary | Abcam (28364) | 1:30 | N/A |
| CD31 | FACS | N/A | BD | 1:5 | FITC |
| VE-Cadherin | IHC/FACS | N/A | Abcam (7047) | 1:5 | PE |
| Phalloidin | IHC | N/A | Invitrogen (A12379) | 1:100 | Alexa Fluor 488 |
| Mouse anti-goat | IHC/FACS | Secondary | Jackson | 1:200 | PE |
| Rabbit anti-donkey | IHC/FACS | Secondary | Jackson | 1:500 | APC |
| Goat anti-rabbit | IHC | Secondary | Invitrogen (A11011) | 1:100 | Alexa Fluor 568 |
| Isotypes | | | | | |
| Rabbit IgG | IHC/FACS | N/A | Abcam | 1:100 | N/A |
| Mouse IgG1 | IHC/FACS | N/A | eBioscience | 1:100 | N/A |
| PerCP IgG1 | FACS | N/A | BD | 1:50 | N/A |
| PECy-7 IgG1 | FACS | N/A | Biolegend | 1:50 | N/A |
| FITC IgG | FACS | N/A | Abcam | 1:50 | N/A |

TABLE 4

Volume calculations for collagen gel

| Reagent | Stock Concentration | Final Concentration | Volume |
|---|---|---|---|
| Rat tail Collagen, type I (Life A1048301) | 3 mg/mL | 2 mg/mL | $V_{COLLAGEN} = \frac{2 \times V_{FINAL}}{3}$ |
| 10X M199 (Sigma M0650) | 10X | 1X | $V_{M199} = \frac{V_{Final}}{3}$ |
| 1N NaOH | 1N | — | $V_{NaOH} = 0.025 \times V_{COLLAGEN}$ |
| EGM (Lonza, CC-3124) | — | — | $V_{EGM} = V_{FINAL} - V_{M199} - V_{NaOH} - V_{COLLAGEN}$ |

Troubleshooting (B) Hemogenic Mesoderm Differentiation•TIMING 2 Days (i) Aspirate media and wash the wells with an equal volume of PBS. Aspirate PBS and add the appropriate volume to each well (Table 2) of 37° C. RPMI+50 ng mL-1 Activin A+1× B-27 without insulin+1× MATRIGEL™ to each well of the plate. Incubate the plate for 17 hours at 37° C., 5% $CO_2$. This is designated day 0.

(ii) On day 1, aspirate the Activin A-containing media and add the appropriate volume to each well (Table 2) of 37° C. RPMI+40 ng mL-1 BMP4+1 μM CHIR-99021+1× B-27 without insulin to each well of the plate. Place the plate in the incubator. To generate hemogenic endothelial cells (HECs), leave the media unchanged for 24 hours (until day 2) and then go to Steps 15(i-iv).
Troubleshooting
Directed Differentiation into Cardiomyocytes•TIMING 4 Days Step 14| (i) Starting with day 3 cardiogenic mesoderm (Steps 13A(i-iii)), aspirate the BMP4-containing media and add the appropriate volume (Table 2) of 37° C. RPMI+1 μM XAV 939+1× B-27 without insulin to each well of the plate. Perform this step no later than 48 hours after Step 13A(ii) media addition. Incubate the plate for 48 hours at 37° C., 5% $CO_2$.

(ii) On day 5, aspirate the XAV-containing media and add the appropriate volume to each well (Table 2) of 37° C. RPMI+1× B-27 minus insulin. Incubate the plate for 48 hours at 37° C., 5% $CO_2$.

(iii) On day 7, aspirate the media and add the appropriate volume to each well (Table 2) of 37° C. RPMI+1× B-27 plus insulin. Incubate the plate for 48 hours at 37° C., 5% CO2. Spontaneous beating can be observed beginning around day 7.

(iv) From day 7 on, after aspirating old media, add 37° C. RPMI+1× B-27 plus insulin media to the wells every other day. Cells will differentiate into definitive cardiomyocytes by day 14. Flow cytometry analysis of day 14 hPSC-derived cardiomyocytes is outlined in the section entitled "Flow cytometry analysis of hPSC-derived cardiomyocytes and ECs."

Directed Differentiation of Endothelial Subtypes•TIMING 3 Days

Endocardial endothelium and hemogenic endothelium are generated by directed differentiation into cardiogenic mesoderm (step 13A) or hemogenic mesoderm (step 13B), respectively. Both lineages are differentiated under the same conditions as outlined below starting on day 2.

Step 15| (i) On day 2, aspirate the BMP4-containing media and add the appropriate volume to each well (Table 2) of 37° C. StemPro+100 mM MTG+100 mM L-Glutamine+50 mg mL-1 Ascorbic Acid+10 μg mL-1 BMP4+5 μg mL-1 bFGF+300 μg mL-1 VEGF. Incubate for 72 hours at 37° C., 5% $CO_2$.

Note: After thawing, ascorbic acid and VEGF are one-time use only.

(ii) On day 5 cells can be analyzed by FACS staining for endothelial markers KDR, CD34, CD31, and VE-cadherin. These markers do not distinguish EECs from HECs. However, blood formation potential is a phenotype that distinguishes EECs from HECs. Detailed methods are provided for analyzing blood forming activity by FACS analysis for markers of primitive hematopoiesis including CD43 and CD235a as well as colony forming activity in methylcellulose. See "Flow cytometry analysis of hPSC-derived cardiomyocytes and ECs" for FACS analyzing methods and "Primitive hematopoietic colony forming assays" for the methylcellulose CFU assay.

(iii) On day 5, split cells using 37° C. VERSENE™ and 0.25% trypsin and re-plate with the appropriate volume to each well (Table 2) of 37° C. EGM+20 ng mL-1 VEGF+20 ng mL-1 bFGF+1 μM CHIR-99021 at a density of 9.0×103 cells cm-2 on 0.1% Gelatin-coated plates. Note: Cells are highly sensitive to sheer stress. When re-plating triturate minimally to avoid cell death. (iv) Split cultures when they achieve 80-90% confluence. (v) FACS analysis can be performed to determine purity of CD31+/VE-cadherin+ cells as described in "Flow cytometry analysis of hPSC-derived cardiomyocytes and ECs." Mature ECs will show de novo lumen formation potential as a key phenotype for functional endothelium. A detailed protocol for assaying tubulogenesis in collagen is outlined in "Collagen-based Tubulogenesis Assay."
Troubleshooting
Timing
    Steps 1-5, thawing hPSCs: 30 min
    Step 6, daily maintenance of hPSCs: 4 d
    Steps 7-11, passaging hPSCs: 20 min
    Step 12, daily maintenance of hPSCs: 4 d
    Step 13A (i-iii), cardiogenic mesoderm differentiation: 2 d
    Step 13B (i-iii), hemogenic mesoderm differentiation: 2 d
    Steps 14 (i-iv), directed differentiation into cardiomyocytes: 12 days
    Steps 15 (i-v), directed differentiation into endothelium: 3-12 days
Troubleshooting
    Additional troubleshooting advice is found in Table 5.

TABLE 5

| | Troubleshooting | | |
|---|---|---|---|
| Step(s) | Problem | Possible Reasons | Solution |
| 1-11 | Undifferentiated cells do not have homogenous morphology | Cells are growing too dense or are not being split at a proper ratio | The split ratio is variable, although generally between 1:4 and 1:15 is appropriate when using VERSENE ™ for passaging. Avoid passaging more than once every 3-4 d. Spontaneous differentiation can occur if hPSCs grow too confluent. |
| 12 | Sub-optimal cell seeding | Improper handling of plate during seeding or excessive cell death. Cell death and uneven cell distribution. | Cells are highly sensitive to trituration during passaging. Keep trituration to a minimum. Use Y- 27632 during plating to increase survival. Careful handling of the plate after seeding is necessary for even distribution of cells. |

TABLE 5-continued

Troubleshooting

| Step(s) | Problem | Possible Reasons | Solution |
|---|---|---|---|
| 13-15 | Poor differentiation in all lineages | Quality of undifferentiated cells | If undifferentiated cells are not maintained properly this will cause poor differentiation. Keep large stocks of karyotypically normal cells. We recommend not passaging more than 10 times before thawing a new batch of cells. |
| | | Cytokine and small molecule bioactivity | For cytokines and small molecules, bioactivity is markedly compromised through repeat freeze thaw cycles. Optimally, aliquot cytokines for single use purposes and use immediately after thawing. Use small molecules according to manufacturer instructions. |
| | | Media quality | Media pH will become more basic with repeated opening. Use media within 2 weeks of first use. B27 should aliquoted and frozen for single use. |
| | | Timing of media changes and technique | Cell fate decisions particularly during the early stages of differentiation are highly sensitive to timing. Therefore try to make media changes +/−30 minutes around the time designated in this protocol. As a matter of technique, also try to add media at every change very slowly so as not to disrupt the cell monolayer. |
| 14 (iv) | Low cardiomyocyte purity | Density at the time of Activin A induction | Some cell lines require very high density seeding (e.g. WTC) while others are more flexible and can generate cardiomyocytes in a wide range of densities (e.g. RUES2). Optimal results should be determined empirically. |
| | | Timing of Wnt manipulation | The timing of Wnt inhibition on day 3 can be sensitive. Optimize the timing of XAV-939 addition in step 14(i). |
| 15 (ii) | Low KDR$_+$/CD34$_+$ cell yield at day 5 | Seeding density | EEC formation is more sensitive to high seeding density compared to HECs. Test different seeding densities in step 12. |
| | | VEGF concentration | Cell lines show variable requirements for VEGF during EC induction. Optimize VEGF concentrations in step 15(i, iii). |

TABLE 5-continued

Troubleshooting

| Step(s) | Problem | Possible Reasons | Solution |
|---|---|---|---|
| | | Reagent bioactivity | Some of the reagents should be frozen for long term storage and thawed for one time use only. VEGF aliquots must be stored at −80° C. then thawed for immediate use. Do not re-freeze aliquots or store at 4° C. for future use. Ascorbic acid is also a one-time use reagent. |
| 15 (iii) | Cell death after re-plating EECs | Too much trituration during passaging | EECs are highly sensitive to sheer stress compared to HECs. Pre-treat EECs with fresh Stempro34 media with Y-27632 two hours prior to passaging and use minimal trituration in step 9. |
| 15 (v) | Low CD31+ endothelial cell yield at day 14 | Media is not fresh | The efficiency of generating definitive ECs requires fresh EGM media. It is recommended that EGM is used within 2 weeks after supplements have been added. |

TABLE 6

Endocardial-specific genes for selection of endocardial endothelial cells

| C-EC - RNA | GCNT1 | TRIM6 | EHD2 | USH1C |
|---|---|---|---|---|
| FOXI1 | MSMO1 | PPP4R1L | LIPH | LRRC15 |
| SLAMF7 | TAL1 | ATP8B3 | PDP1 | ARL6 |
| CACNG3 | KLHL24 | NPY1R | TNFRSF10A | PIK3R5 |
| APLN | EGFL7 | ZBTB11 | ST8SIA4 | AHNAK2 |
| MYLKP1 | CCND1 | OLFML3 | WIPI1 | TRPV4 |
| LAPTM5 | HPS3 | PRX | PLK3 | RP11-206M11.7 |
| ITGA10 | MICALL2 | SPN | DRP2 | HSPA4L |
| IPCEF1 | DDB2 | GPR56 | YOD1 | ALMS1-IT1 |
| AQP1 | APLNR | ZBTB7B | KCNA5 | EMX1 |
| GRAP2 | MIAT | YES1 | NHLRC2 | MTUS1 |
| SOX10 | GAD1 | GDF15 | SYN3 | OTOG |
| VAV3 | NDRG1 | ANKRD33 | MMP17 | IFITM1 |
| ATP2A3 | GPR162 | DES | KLF4 | ADRA2A |
| PTGS1 | GOLT1B | TMEM74B | SCGN | CACNA2D3 |
| CDKN1A | GPR97 | ELK4 | DUSP16 | SNAP91 |
| NR2F2 | TPBGL | SLC43A2 | LINC00152 | ADCY2 |
| CREB5 | ELF4 | LGALS1 | CORO2A | AC021860.1 |
| ETV2 | TMF1 | KLF8 | TBC1D26 | RP11-217H19.1 |
| PRKCB | THBD | CR1L | SLC15A3 | ULBP1 |
| NR4A1 | FAM102B | PITPNM2 | SH2D4B | USP31 |
| FMNL1 | FAXDC2 | STK17A | FHAD1 | LINC00458 |
| CBFA2T3 | ANK1 | SEC24D | TMEM173 | RP11-888D10.4 |
| IRAK1 | MECP2 | TNFRSF10D | TMEM108 | LPAR5 |
| DOCK4 | MVP | RP11-281P23.2 | PCDH17 | CLDN11 |
| BTG2 | CYP2S1 | ZIC3 | APBB2 | ALDH1A3 |
| ZAP70 | STARD9 | ABCA9-AS1 | PLCB1 | ARID5A |
| PLCB4 | WWP1 | PROCR | PCDH12 | RNF125 |
| EDA2R | PDGFA | HCLS1 | SLC25A37 | GDPD1 |
| CDH13 | WDR44 | SLC9A3R2 | SLC16A6 | ZSCAN4 |
| FHOD1 | SPAG9 | RGS17 | SCN1B | SGIP1 |
| ADD2 | ADRA2B | CD79B | CCND2 | PAPPA |
| SP6 | KANK2 | ACP5 | CACNA1F | IL21R |
| INSIG1 | CRMP1 | HEY2 | TUBA4A | ISG20 |
| BBC3 | SEMA7A | PLEKHH2 | KLF9 | SPATA18 |
| CNTNAP1 | PLCD1 | MIR4435-1HG | NMU | CDKN2D |
| MAP4K5 | BHLHE40 | SPINT1 | ZNF654 | RGS20 |
| TXNIP | RAB11A | ABCA5 | SCDP1 | VGF |
| GADD45A | L1CAM | FAS | RP11-123M21.2 | PLXNB3 |
| PODXL | RP11-215G15.5 | GRM4 | ZMAT3 | ANKRD33B |
| SLC39A8 | NR1D1 | TM4SF1 | PPP1R14C | PPAPDC1A |
| ESYT1 | PLXDC2 | SDCBP2 | TPPP | GATAD2B |
| IFNGR1 | RAD21L1 | FLT4 | CABYR | PRDM8 |
| EPHA2 | TANC1 | GABARAPL1 | PCLO | ANKRD55 |

TABLE 6-continued

Endocardial-specific genes for selection of endocardial endothelial cells

| | | | | |
|---|---|---|---|---|
| RRM2B | AMN1 | HYPK | RP11-115D19.1 | DNM3 |
| TNIK | ADIRF-AS1 | NFE2L3 | SLC35D3 | CXCL16 |
| SV2A | TUBB2A | FOXJ2 | CST1 | RELL1 |
| PPFIBP1 | CD226 | PCDH10 | SLC16A7 | MXD1 |
| TAF1D | STARD4 | PHLDA1 | NME8 | TBC1D2 |
| GCC2 | HELZ2 | MATN1-AS1 | NGEF | SLC22A18 |
| C18orf54 | ARRDC4 | ASIC4 | CRHR2 | AMZ1 |
| TRIM24 | ATCAY | RHOH | PHLDA2 | CEACAM21 |
| MSI2 | TMCC2 | SIGLEC15 | SESN1 | CST4 |
| ITPR1 | GOLGA3 | ARHGAP9 | STX1A | CTD-2647L4.4 |
| TUBB2B | TRPV2 | SLC17A7 | ICAM5 | CPHL1P |
| NUFIP2 | GAS2L3 | NXPH3 | SH2D2A | GEM |
| MSN | MSNP1 | RAC2 | MID2 | CTCFL |
| ASH2L | MAPKBP1 | UNC13A | LEFTY2 | RP11-32B5.1 |
| ZFP36 | SLC20A1 | PTCHD4 | ASGR2 | ZNF699 |
| GFPT1 | MLXIPL | PEAR1 | PPAPDC1B | SLC6A16 |
| TNFRSF10C | LINC00924 | MAML D1 | CRYBG3 | GYPB |
| PRKAB2 | CTBS | ADRB3 | CCPG1 | SP7 |
| CD34 | EGR3 | ELMO3 | AF127936.7 | PRSS53 |
| TCP11L2 | TKTL1 | RP11-844P9.2 | AF064858.8 | RP11-1217F2.1 |
| CTD-2006H14.2 | RP11-180C16.1 | PDE4C | GRM2 | FGF17 |
| PTPN22 | AC020907.2 | PTGER3 | GYPE | ANKRD44 |
| IL1RL1 | MDM2 | ZNF805 | GPR141 | DKFZP667F0711 |
| RP3-370M22.8 | CACTIN-AS1 | FAM72A | TBX1 | CD163L1 |
| FLVCR2 | MCEE | MAGEA11 | RP11-462G2.1 | AKR1C1 |
| RP11-909N17.3 | VENTX | GABBR2 | RP11-256I9.2 | |

Flow Cytometry Analysis of hPSC-Derived Cardiomyocytes and Endothelial Cells
Exemplary Methods 1. Wash cells with PBS. Aspirate PBS and add 10% Trypsin-VERSENE™ solution (vol/vol) (0.25% Trypsin) and incubate the cells at 37° C.
2. Monitor cells under a microscope until they are single cells—roughly 2-5 minutes.
3. For all cells triturate no more than 3-5 times to re-suspend. To transition the colonies to single cells, keeping cells longer in trypsin solution is better than over triturating the cells. Stop the Trypsin-VERSENE™ reaction by transferring cells from Step 1 into a tube with an equal volume of stop solution (FBS:DMEM 1:1+200 Units mL-1 of DNase1).
4. Centrifuge cells at 300 g for 5 min and aspirate media.

Staining Cardiomyocytes

5. If performing cTnT/SMA staining, cells must be fixed prior to staining. Re-suspend cells from Step 4 in 200 µl of 4% Paraformaldehyde solution and incubate at 4° C. for 10 min. Centrifuge cells at 300 g for 5 min and pipette paraformaldehyde into appropriate waste container and re-suspend cell pellets in 300-500 µl of 5% FBS-PBS solution (vol/vol).

PAUSE POINT Cells can be kept fixed at 4° C. for up to 7 days before staining.

6. Count cells with hemocytometer and transfer 1.0-5.0× 10⁵ cells of each sample to one well of a 96-well round-bottom plate. Centrifuge plate at 1200 rpm for 5 min and decant supernatant.
7. Re-suspend pellet with 50 µl of 0.75% Saponin in FBS-PBS (5%) (wt/vol) with the appropriate dilution of primary antibody according to Table 3. Antibody combinations of cTnT/SMA are recommended for double staining. Incubate at room temperature for at least 30 min.
8. Add 150 µl of 0.75% Saponin in FBS-PBS (5%) (wt/vol) to each well and triturate 5 times. Centrifuge the plate for 5 min and decant supernatant.
9. Repeat Step 11 using 200 µl of 0.75% Saponin in FBS-PBS (5%) (wt/vol).
10. Re-suspend the pellet with 50 µl of FBS-PBS (5%) (vol/vol) with appropriate dilution of secondary antibody according to Table 3. Incubate at room temperature for at least 30 min in darkness.
11. Repeat Steps 8-9 using FBS-PBS (5%) (vol/vol).
12. Add 200 µl of FBS-PBS (5%) (vol/vol) to each well and triturate 5 times. Transfer each sample to a separate 5 mL FACS tube. Add an additional 200 µl of FBS-PBS (5%) (vol/vol) and 100 µl of 4% Paraformaldehyde.

PAUSE POINT Cells can be kept at 4° C. for up to 7 days before flow cytometric analysis.

Staining Endothelial Cells

This protocol is useful for analyzing day 5 ECs or later stage definitive ECs.

13. ECs and hematopoietic derivatives are stained and analyzed live. Do not fix cells at any point in the protocol. Re-suspend cells in 200 µl of DMEM+10% FBS and transfer cells to one well of a 96-well round-bottom plate. Centrifuge plate at 1200 rpm for 5 min and decant supernatant.
14. Re-suspend cells in DMEM containing appropriate dilutions of desired antibody to a total volume of 50 µl (Table 3).
15. Incubate at 4° C. for 30-45 minutes.
16. Add 150 µl of FBS-PBS (5%) (vol/vol) to each well and triturate 5 times. Centrifuge the plate for 5 min and decant supernatant.
17. Repeat Step 16 using 200 µl of FBS-PBS (5%) (vol/vol).
18. Analyze cells immediately by flow cytometry.

Primitive Hematopoietic Colony Forming Assays

1. Harvest and count cells with a hemocytometer. Spin and re-suspend cells at a concentration of 1×10⁶ cells per mL in Iscove's Modified Dulbecco's Medium.
2. Add 300 microliters of cells to 3 mL of methylcellulose media containing recombinant human stem cell factor, GM-CSF, GCSF, IL-3, and erythropoietin). Vortex vigorously to evenly distribute cells.
3. Using a 3 mL syringe and 16 gauge 1.5 inch needle, aliquot 1 mL of methylcellulose media with cells to each of three 35 mm suspension culture dishes. Rotate plates to evenly distribute methylcellulose media.

4. Place 2 plates with methylcellulose media into a 10 cm tissue culture dish with one additional 35 mm dish without a lid containing sterile water, to maintain proper humidity for methylcellulose. Incubate at 37° C. in 5% $CO_2$.

5. After 12-14 days, hematopoietic colonies can be scored visually. As this early stage of hematopoietic differentiation, colonies consist predominantly of primitive erythroid (EryP) and macrophage (Mac) lineages (FIG. 5)

Additional Materials
Iscove's Modified Dulbecco's Medium (Gibco, 12440)
Methylcellulose media with human cytokines (H4034, Stem Cell Technologies)
35 mm suspension culture dishes (Corning 430588)

Collagen-Based Tubulogenesis Assay

1. Harvest day 14 endothelial cells (ECs) with standard enzymatic digestion methods (0.05% Trypsin). Count the cells using a hemocytometer and set aside on ice during collagen preparation.

2. Dilute and neutralize collagen gel to a final concentration of 2 mg/mL
   a. Calculate the volume of reagents needed (Table 4)
   b. Combine 10× M199 media, NaOH, and half of the total EGM. Mix together and combine with collagen. Mix well by pipetting slowly until a homogenous solution is obtained.

Note: Keep collagen on ice while mixing to prevent gelation until ready. Mix slowly and carefully to avoid bubbles.

Note: Monitor the pH of the collagen mixture to ensure it is properly neutralized. If the mixture is too acidic, continue to bring the pH up with NaOH until pH 7.2 is reached. Adjust the volume of EGM used in step 4 as needed to maintain constant final volume.

3. Determine the number of cells required to achieve a final cell density of $2\times10^6$/mL (#cells=$2\times10^6 \times V_{FINAL}$). Resuspend cells in the remaining EGM volume and add to the neutralized collagen mixture. Mix well by pipetting until the cells are evenly distributed.

4. Pipet the collagen+cell mixture into wells of angiogenesis μ-slides (4 mm diameter wells, 10 μL volume/well). Allow the samples to gel at 37° C. for 20 minutes.

5. After gelation, feed with EGM supplemented with 1 μM Chiron-99021, 20 ng/mL bFGF, and 20 ng/mL VEGF and replace with fresh media every day.

6. After 2 days, fix the samples in 3.7% formaldehyde for 10 minutes and wash in PBS.

7. Stain in situ for CD31 and Phalloidin using standard immunohistochemistry methods.
   a. Block fixed samples in PBS with 2% BSA and 0.5% Triton X-100.
   b. Incubate overnight with primary antibody at 4° C.: 1:30 Rb pAb to hCD31.
   c. Wash with PBS 3 times, 15 min each.
   d. Incubate with secondary antibodies for 1 hour at room temperature: 1:100
   Alexa Fluor 488 Phalloidin and 1:100 Alexa Fluor goat anti-rabbit 568.
   e. Image samples using confocal microscopy to obtain three dimensional z-stacks.

Additional Materials
Rat tail Collagen, type I (Life A1048301)
10× M199 (Sigma M0650)
1N NaOH
μ-slide Angiogenesis (Ibidi 81506)

Results

The protocol described herein provides an efficient methodology for generating high purity definitive mesodermal subtypes from hPSCs including cardiomyocytes, endocardial endothelial cells, and vascular endothelial cells. Upon induction of differentiation with Activin A and BMP4, cells show marked morphological changes as they transit from pluripotency to mesoderm (FIG. 8B) with marked differences in gene expression (Tables 1 and 3) consistent with lineage specification into cardiogenic vs. hemogenic mesoderm. Under conditions of Wnt inhibition from cardiogenic mesoderm, differentiation shows time-dependent activation of cardiac transcription factor and myofilament genes by approximately day 5 of differentiation. Beating is observed approximately by day 7-10 with differentiation achieving approximately 90% cTnT+ cells by day 14 (FIG. 3).

Figure 7A:
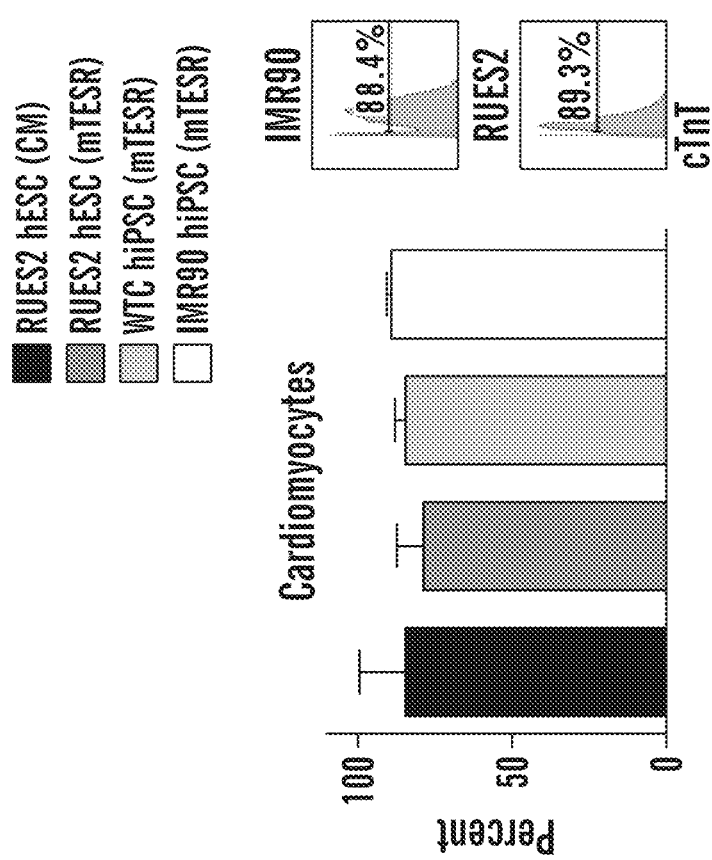
FIGS. 7A-7C Efficiency of differentiation assessed in multiple hPSC lines. The efficiency of differentiation was assessed in RUES2 cell cultured in condition media (CM) and defined media (mTESR), WTC hiPSCs, and IMR90 hiPSCs.
Figure 7B:
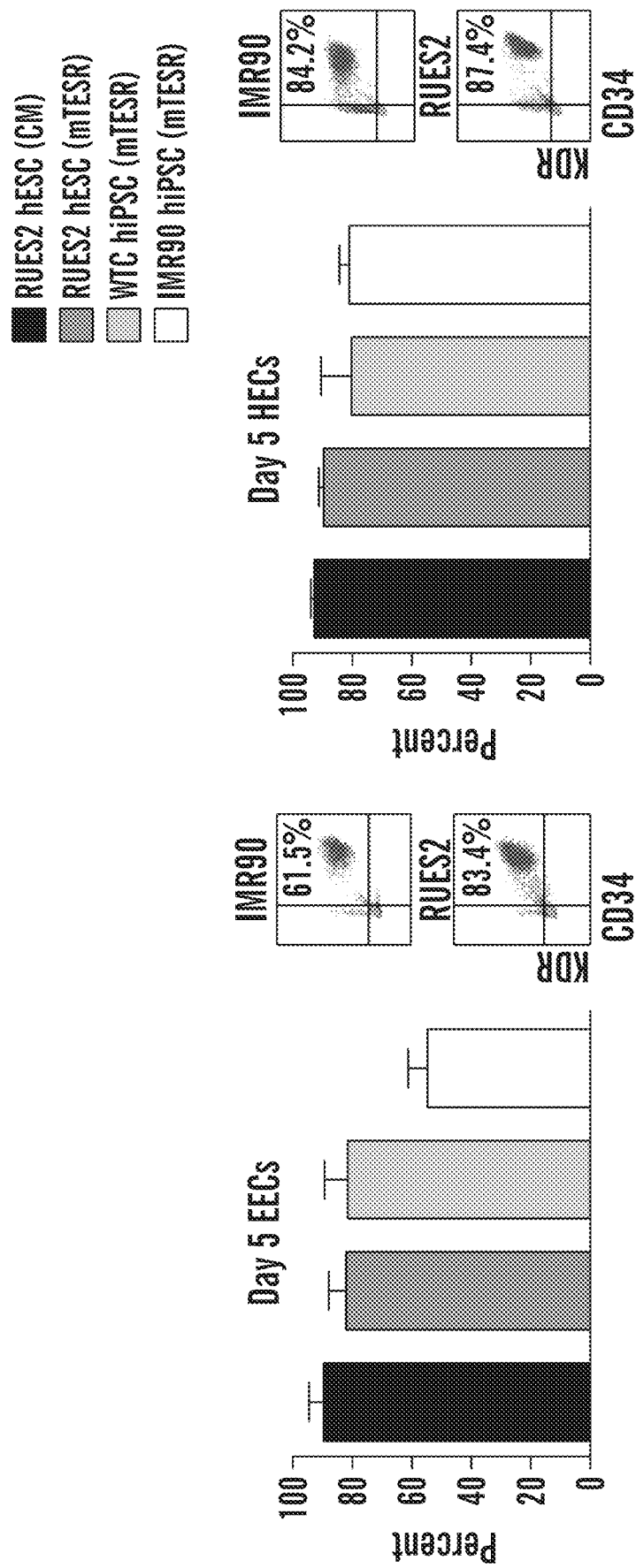
Figure 7C:
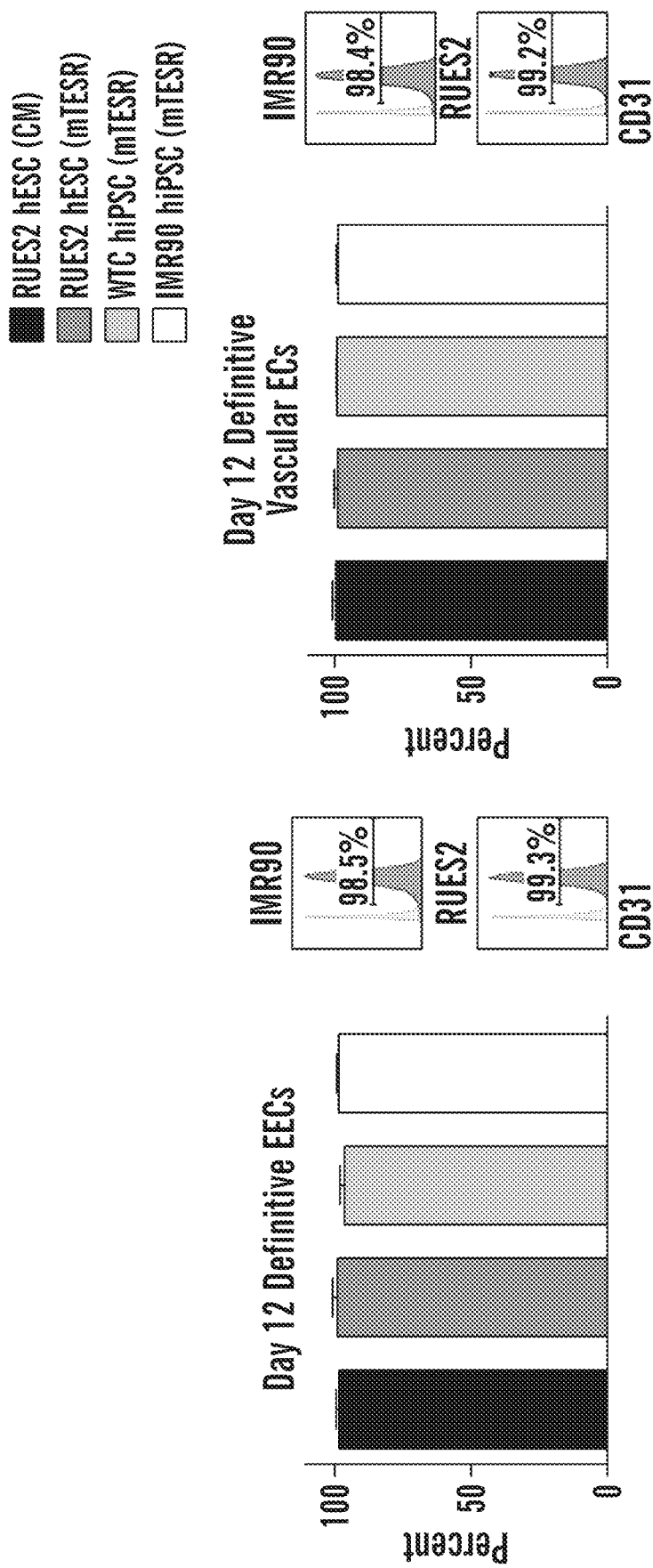

For endothelial differentiation, cells will progress to EECs and HECs by day 5 of differentiation achieving approximately 90% KDR+/CD34+ cells with gene expression patterns that distinguish endocardial vs. hemogenic EC lineages. Evidence of primitive hematopoiesis is seen almost entirely in HECs based on the presence of CD43+/CD235a+ cells (FIG. 5A). Similarly, functional blood forming assays in methylcellulose will likely show very little blood forming potential in EEC cultures, whereas HECs should show robust Ery-P and Mac colony forming units (FIG. 5B). As cells mature into definitive endothelial cells they become greater than 90% CD31+/VE-cadherin+ by day 14 of differentiation and show robust lumen formation in collagen (FIG. 6). This protocol has been found to be versatile with high efficiency differentiation from hESC and hiPSC lines (FIG. 7).

REFERENCES

1 Murry, C. E. & Keller, G. Differentiation of embryonic stem cells to clinically relevant populations: lessons from embryonic development. Cell 132, 661-680, doi:S0092-8674(08)00216-X [pii] 10.1016/j.cell.2008.02.008 (2008).

2 Xu, P. F., Houssin, N., Ferri-Lagneau, K. F., Thisse, B. & Thisse, C. Construction of a vertebrate embryo from two opposing morphogen gradients. Science 344, 87-89, doi: 10.1126/science.1248252 (2014).

3 Kattman, S. J. et al. Stage-specific optimization of activin/nodal and BMP signaling promotes cardiac differentiation of mouse and human pluripotent stem cell lines. Cell Stem Cell 8, 228-240, doi:10.1016/j.stem.2010.12.008 (2011).

4 Nostro, M. C., Cheng, X., Keller, G. M. & Gadue, P. Wnt, activin, and BMP signaling regulate distinct stages in the developmental pathway from embryonic stem cells to blood. Cell Stem Cell 2, 60-71, doi:10.1016/j.stem.2007.10.011 (2008).

5 Sumi, T., Tsuneyoshi, N., Nakatsuji, N. & Suemori, H. Defining early lineage specification of human embryonic stem cells by the orchestrated balance of canonical Wnt/beta-catenin, Activin/Nodal and BMP signaling. Development 135, 2969-2979, doi:10.1242/dev.021121 (2008).

6 Palpant, N. J., Hofsteen, P., Pabon, L., Reinecke, H. & Murry, C. E. Cardiac development in zebrafish and human embryonic stem cells is inhibited by exposure to tobacco cigarettes and e-cigarettes. *PLoS One* 10, e0126259, doi: 10.1371/journal.pone.0126259 (2015).

7 Palpant, N. J. et al. Inhibition of β-catenin signaling respecifies anterior-like endothelium into beating human cardiomyocytes. *Development*, doi:10.1242/dev.117010 (2015).

8 Palpant, N. J. et al. Transmembrane protein 88: a Wnt regulatory protein that specifies cardiomyocyte development. *Development* 140, 3799-3808, doi:10.1242/dev.094789 (2013).

9 Paige, S. L. et al. A temporal chromatin signature in human embryonic stem cells identifies regulators of cardiac development. *Cell* 151, 221-232, doi:S0092-8674(12)01058-6 [pii] 10.1016/j.cell.2012.08.027 (2012).

10 Wamstad, J. A. et al. Dynamic and coordinated epigenetic regulation of developmental transitions in the cardiac lineage. *Cell* 151, 206-220, doi:10.1016/j.cell.2012.07.035 (2012).

11 Willems, E. et al. Small-molecule inhibitors of the Wnt pathway potently promote cardiomyocytes from human embryonic stem cell-derived mesoderm. *Circ Res* 109, 360-364, doi:10.1161/CIRCRESAHA.111.249540 (2011).

12 Dubois, N. C. et al. SIRPA is a specific cell-surface marker for isolating cardiomyocytes derived from human pluripotent stem cells. *Nat Biotechnol* 29, 1011-1018, doi:10.1038/nbt.2005 (2011).

13 White, M. P. et al. Limited gene expression variation in human embryonic stem cell and induced pluripotent stem cell-derived endothelial cells. *Stem Cells* 31, 92-103, doi:10.1002/stem.1267 (2013).

14 Rafii, S. et al. Human ESC-derived hemogenic endothelial cells undergo distinct waves of endothelial to hematopoietic transition. *Blood* 121, 770-780, doi:10.1182/blood-2012-07-444208 (2013).

15 Kennedy, M. et al. T lymphocyte potential marks the emergence of definitive hematopoietic progenitors in human pluripotent stem cell differentiation cultures. *Cell Rep* 2, 1722-1735, doi:10.1016/j.celrep.2012.11.003 (2012).

16 Choi, K. D. et al. Identification of the hemogenic endothelial progenitor and its direct precursor in human pluripotent stem cell differentiation cultures. *Cell Rep* 2, 553-567, doi:10.1016/j.celrep.2012.08.002 (2012).

17 Kennedy, M., D'Souza, S. L., Lynch-Kattman, M., Schwantz, S. & Keller, G. Development of the hemangioblast defines the onset of hematopoiesis in human ES cell differentiation cultures. *Blood* 109, 2679-2687, doi: 10.1182/blood-2006-09-047704 (2007).

18 Ovchinnikov, D. A. et al. Isolation of contractile cardiomyocytes from human pluripotent stem-cell derived cardiomyogenic cultures using a human NCX1-EGFP reporter. *Stem Cells Dev* 24, 11-20, doi:10.1089/scd.2014.0195 (2015).

19 Elliott, D. A. et al. NKX2-5(eGFP/w) hESCs for isolation of human cardiac progenitors and cardiomyocytes. *Nat Methods* 8, 1037-1040, doi:10.1038/nmeth.1740 (2011).

20 Tohyama, S. et al. Distinct metabolic flow enables large-scale purification of mouse and human pluripotent stem cell-derived cardiomyocytes. *Cell Stem Cell* 12, 127-137, doi:10.1016/j.stem.2012.09.013 (2013).

21 Mendjan, S. et al. NANOG and CDX2 Pattern Distinct Subtypes of Human Mesoderm during Exit from Pluripotency. *Cell Stem Cell*, doi:10.1016/j.stem.2014.06.006 (2014).

22 Faial, T. et al. Brachyury and SMAD signalling collaboratively orchestrate distinct mesoderm and endoderm gene regulatory networks in differentiating human embryonic stem cells. *Development* 142, 2121-2135, doi: 10.1242/dev.117838 (2015).

23 Yutzey, K. E. & Bader, D. Diversification of cardiomyogenic cell lineages during early heart development. *Circ Res* 77, 216-219 (1995).

24 Van Handel, B. et al. Scl represses cardiomyogenesis in prospective hemogenic endothelium and endocardium. *Cell* 150, 590-605, doi:S0092-8674(12)00781-7 [pii] 10.1016/j.cell.2012.06.026 (2012).

25 Zhang, J. et al. Extracellular matrix promotes highly efficient cardiac differentiation of human pluripotent stem cells: the matrix sandwich method. *Circ Res* 111, 1125-1136, doi:10.1161/CIRCRESAHA.112.273144 (2012).

26 Lian, X. et al. Robust cardiomyocyte differentiation from human pluripotent stem cells via temporal modulation of canonical Wnt signaling. *Proc Natl Acad Sci USA* 109, E1848-1857, doi:1200250109 [pii] 10.1073/pnas.1200250109 (2012).

27 Paige, S. L. et al. Endogenous Wnt/beta-catenin signaling is required for cardiac differentiation in human embryonic stem cells. *PLoS One* 5, e11134, doi:10.1371/journal.pone.0011134 (2010).

28 Ueno, S. et al. Biphasic role for Wnt/beta-catenin signaling in cardiac specification in zebrafish and embryonic stem cells. *Proc Natl Acad Sci USA* 104, 9685-9690, doi:0702859104 [pii] 10.1073/pnas.0702859104 (2007).

29 Mummery, C. L. et al. Differentiation of human embryonic stem cells and induced pluripotent stem cells to cardiomyocytes: a methods overview. *Circ Res* 111, 344-358, doi:10.1161/CIRCRESAHA.110.227512 (2012).

30 Lian, X., Zhang, J., Zhu, K., Kamp, T. J. & Palecek, S. P. Insulin inhibits cardiac mesoderm, not mesendoderm, formation during cardiac differentiation of human pluripotent stem cells and modulation of canonical Wnt signaling can rescue this inhibition. *Stem Cells* 31, 447-457, doi:10.1002/stem.1289 (2013).

31 Lian, X. et al. Directed cardiomyocyte differentiation from human pluripotent stem cells by modulating Wnt/β-catenin signaling under fully defined conditions. *Nat Protoc* 8, 162-175, doi:10.1038/nprot.2012.150 (2013).

32 Gantz, J. A. et al. Targeted genomic integration of a selectable floxed dual fluorescence reporter in human embryonic stem cells. *PLoS One* 7, e46971, doi:10.1371/journal.pone.0046971 (2012).

33 Nourse, M. B. et al. VEGF induces differentiation of functional endothelium from human embryonic stem cells: implications for tissue engineering. *Arterioscler Thromb Vasc Biol* 30, 80-89, doi:10.1161/ATVBAHA.109.194233 (2010).

34 Orlova, V. V. et al. Generation, expansion and functional analysis of endothelial cells and pericytes derived from human pluripotent stem cells. *Nat Protoc* 9, 1514-1531, doi:10.1038/nprot.2014.102 (2014).

35 Levenberg, S., Ferreira, L. S., Chen-Konak, L., Kraehenbuehl, T. P. & Langer, R. Isolation, differentiation and characterization of vascular cells derived from human embryonic stem cells. *Nat Protoc* 5, 1115-1126, doi: 10.1038/nprot.2010.31 (2010).

36 Misfeldt, A. M. et al. Endocardial cells are a distinct endothelial lineage derived from Flk1+ multipotent cardiovascular progenitors. *Dev Biol* 333, 78-89, doi: 10.1016/j.ydbio.2009.06.033 (2009).

37 Peterkin, T., Gibson, A. & Patient, R. Common genetic control of haemangioblast and cardiac development in zebrafish. *Development* 136, 1465-1474, doi:10.1242/dev.032748 (2009).
38 de la Pompa, J. L. et al. Role of the NF-ATc transcription factor in morphogenesis of cardiac valves and septum. *Nature* 392, 182-186, doi:10.1038/32419 (1998).
39 Ranger, A. M. et al. The transcription factor NF-ATc is essential for cardiac valve formation. *Nature* 392, 186-190, doi:10.1038/32426 (1998).
40 Morikawa, Y. & Cserjesi, P. Extra-embryonic vasculature development is regulated by the transcription factor HAND1. *Development* 131, 2195-2204, doi:10.1242/dev.01091 (2004).
41 Barnes, R. M., Firulli, B. A., Conway, S. J., Vincentz, J. W. & Firulli, A. B. Analysis of the Hand1 cell lineage reveals novel contributions to cardiovascular, neural crest, extra-embryonic, and lateral mesoderm derivatives. *Dev Dyn* 239, 3086-3097, doi:10.1002/dvdy.22428 (2010).

What is claimed is:

1. A method of promoting cardiac wound healing in a subject in need thereof, the method comprising administering human endocardial endothelial cells derived from human pluripotent stem cells to a cardiac wound, wherein the human endocardial endothelial cells are present on, or in a scaffold material, and wherein the wound results from a cardiac injury, a cardiac disease, or a cardiac disorder.

2. The method of claim 1, wherein the pluripotent stem cells are autologous to the subject.

3. The method of claim 2, wherein the pluripotent stem cells are an induced pluripotent stem cells.

4. The method of claim 1, wherein the scaffold material comprises a polymer, copolymer, or a matrix.

5. The method of claim 4, wherein the polymer or matrix comprises collagen, fibrin, or a polysaccharide.

6. The method of claim 1, wherein the human endocardial endothelial cells are administered before or after closure of the wound.

7. The method of claim 1, wherein the human endocardial endothelial cells are applied either alone or with one or more other factors that promote wound healing.

8. The method of claim 1, wherein the one or more other factors that promote wound healing are selected from the group consisting of Fibroblast Growth Factor 10 (FGF10), Platelet-Derived Growth Factor (PDGF), Transforming Growth Factor Beta (TGFβ), Bone Morphogenic Protein 4 (BMP4), Epidermal Growth Factor (EGF/TGFα), and Vascular Endothelium Growth Factor (VEGF).

9. The method of claim 1, wherein the human endocardial endothelial cells are administered in an effective amount of human endocardial cells, wherein the effective amount comprises at least $1\times10^3$, at least $1\times10^4$, at least $1\times10^5$, at least $5\times10^5$, at least $1\times10^6$, at least $2\times10^6$, at least $3\times10^6$, at least $4\times10^6$, at least $5\times10^6$, at least $6\times10^6$, at least $7\times10^6$, at least $8\times10^6$, at least $9\times10^6$, at least $1\times10^7$, at least $1.1\times10^7$, at least $1.2\times10^7$, at least $1.3\times10^7$, at least $1.4\times10^7$, $1.5\times10^7$, at least $1.6\times10^7$, at least $1.7\times10^7$, at least $1.8\times10^7$, at least $1.9\times10^7$, at least $1\times10^8$, at least $2\times10^8$, at least $5\times10^8$, at least $7\times10^8$, at least $1\times10^9$, at least $2\times10^9$, at least $3\times10^9$, at least $4\times10^9$, at least $5\times10^9$ cells.

10. The method of claim 1, wherein the human endocardial endothelial cells are administered at the onset of a symptom or indication of the cardiac injury, the cardiac disease, or the cardiac disorder.

11. The method of claim 1, wherein the cardiac injury, cardiac disease, or cardiac disorder is selected from the group consisting of myocardial infarction, heart failure, cardiomyopathy, congenital heart defect, heart valve disease/dysfunction, endocarditis, rheumatic fever, mitral valve prolapse, infective endocarditis, hypertrophic cardiomyopathy, dilated cardiomyopathy, myocarditis, cardiomegaly, and mitral insufficiency.

12. The method of claim 10, wherein the cardiac injury, cardiac disease, or cardiac disorder is selected from the group consisting of myocardial infarction, heart failure, cardiomyopathy, congenital heart defect, heart valve disease/dysfunction, endocarditis, rheumatic fever, mitral valve prolapse, infective endocarditis, hypertrophic cardiomyopathy, dilated cardiomyopathy, myocarditis, cardiomegaly, and mitral insufficiency.

13. The method of claim 1, wherein the cardiac wound results from a vascular disease-associated cardiac disease, disorder, or injury.

* * * * *